US008962283B2

(12) United States Patent
Cascao-Pereira et al.

(10) Patent No.: US 8,962,283 B2
(45) Date of Patent: *Feb. 24, 2015

(54) TS-23 ALPHA-AMYLASE VARIANTS WITH ALTERED PROPERTIES

(71) Applicant: Danisco US Inc., Palo Alto, CA (US)

(72) Inventors: Luis G. Cascao-Pereira, Redwood City, CA (US); Claudine Chang, Mountain View, CA (US); Clement Choy, Alamo, CA (US); James T. Kellis, Jr., Woodside, CA (US); Brian E. Jones, Leidschendam (NL); Melodie Estabrook, Mountain View, CA (US); Marc Kolkman, Oegstgeest (NL); Chris Leeflang, GA Twisk (NL); Casper Vroemen, Oegstgeest (NL); Walter Weyler, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/899,057

(22) Filed: May 21, 2013

(65) Prior Publication Data

US 2013/0344542 A1 Dec. 26, 2013

Related U.S. Application Data

(60) Continuation of application No. 13/540,064, filed on Jul. 2, 2012, now Pat. No. 8,460,916, which is a division of application No. 12/365,646, filed on Feb. 4, 2009, now Pat. No. 8,236,545.

(60) Provisional application No. 61/026,056, filed on Feb. 4, 2008, provisional application No. 61/059,403, filed on Jun. 6, 2008.

(51) Int. Cl.
| | |
|---|---|
| C12P 21/06 | (2006.01) |
| C12N 9/00 | (2006.01) |
| C12N 9/28 | (2006.01) |
| C12N 1/20 | (2006.01) |
| C12N 15/00 | (2006.01) |
| C11D 3/386 | (2006.01) |
| C07H 21/04 | (2006.01) |
| A21D 8/04 | (2006.01) |
| A23K 1/165 | (2006.01) |
| A23K 1/18 | (2006.01) |
| A23L 1/03 | (2006.01) |

(52) U.S. Cl.
CPC .............. *C12N 9/2417* (2013.01); *A21D 8/042* (2013.01); *A23K 1/1653* (2013.01); *A23K 1/1826* (2013.01); *A23L 1/034* (2013.01)
USPC ............ 435/99; 435/69.1; 435/183; 435/202; 435/252.3; 435/320.1; 510/226; 536/23.2

(58) Field of Classification Search
None
See application file for complete search history.

(56) References Cited

U.S. PATENT DOCUMENTS

| | | | |
|---|---|---|---|
| 3,912,590 | A | 10/1975 | Slott et al. |
| 4,106,991 | A | 8/1978 | Markussen et al. |
| 4,316,956 | A | 2/1982 | Lutzen |
| 4,335,208 | A | 6/1982 | Norman |
| 4,435,307 | A | 3/1984 | Barbesgaard et al. |
| 4,536,182 | A | 8/1985 | Tatin |
| RE32,153 | E | 5/1986 | Tamura et al. |
| 4,587,215 | A | 5/1986 | Hirsh |
| 4,643,736 | A | 2/1987 | Cholley |
| 4,661,452 | A | 4/1987 | Markussen et al. |
| 4,689,297 | A | 8/1987 | Good et al. |
| 4,760,025 | A | 7/1988 | Estell et al. |
| 5,231,017 | A | 7/1993 | Lantero et al. |
| 5,324,649 | A | 6/1994 | Arnold et al. |
| 5,427,936 | A | 6/1995 | Moeller et al. |
| 5,648,263 | A | 7/1997 | Schulein et al. |
| 5,691,178 | A | 11/1997 | Schulein et al. |
| 5,776,757 | A | 7/1998 | Schulein et al. |
| 5,814,501 | A | 9/1998 | Becker et al. |
| 5,827,718 | A | 10/1998 | Ishida et al. |
| 5,942,431 | A | 8/1999 | Yoneda et al. |
| 6,017,867 | A | 1/2000 | Baillely et al. |
| 6,077,316 | A | 6/2000 | Lund et al. |
| 6,093,562 | A | 7/2000 | Bisgard-Frantzen et al. |
| 6,297,038 | B1 | 10/2001 | Bisgard-Frantzen et al. |
| 6,326,443 | B1 | 12/2001 | Monoi et al. |
| 6,403,355 | B1 | 6/2002 | Hagihara et al. |
| 6,528,298 | B1 | 3/2003 | Svendsen et al. |
| 6,562,612 | B2 | 5/2003 | Jones et al. |
| 6,867,031 | B2 | 3/2005 | Bisgård-Frantzen et al. |
| 7,122,334 | B2 | 10/2006 | Schellenberger et al. |
| 7,498,158 | B2 | 3/2009 | Svendsen et al. |
| 7,713,723 | B1 | 5/2010 | Thisted et al. |

(Continued)

FOREIGN PATENT DOCUMENTS

| | | |
|---|---|---|
| AU | 2008325250 | 5/2009 |
| CA | 2202553 | 4/1996 |

(Continued)

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
U.S. Appl. No. 10/630,203, filed Nov. 10, 2005, Thisted et al.
Chen, J.-T., et al., "Structure and expression of an amylopullulanase gene from *Bacillus stearothermophilus* TS-23." *Biotechnol. Appl. Biochem.* 33: 189-199, 2001.
Chica, R.A., et al. "Semi-rational approaches to engineering enzyme activity: combining the benefits of directed evolution and rational design." *Curr. Opin. Biotechnol.* 6(4): 378-384, 2005.

(Continued)

*Primary Examiner* — Christian Fronda
(74) *Attorney, Agent, or Firm* — Danisco US Inc.

(57) ABSTRACT

Described are variants (mutants) of a parent alpha-amylase having alpha-amylase activity and exhibiting altered properties relative to the parent alpha-amylase, and methods of use, thereof.

13 Claims, 11 Drawing Sheets

(56) References Cited

U.S. PATENT DOCUMENTS

| | | | |
|---|---|---|---|
| 8,153,412 | B2 | 4/2012 | Chang et al. |
| 8,507,244 | B2 | 8/2013 | Shaw et al. |
| 8,535,927 | B1 | 9/2013 | Jones et al. |
| 2005/0202535 | A1 | 9/2005 | Collier |
| 2005/0250663 | A1 | 11/2005 | Thisted et al. |
| 2007/0212768 | A1 | 9/2007 | Bessler et al. |
| 2008/0293610 | A1 | 11/2008 | Shaw et al. |
| 2009/0143270 | A1 | 6/2009 | Svendsen et al. |
| 2009/0280527 | A1 | 11/2009 | Bisgard-Frantzen et al. |
| 2010/0048446 | A1 | 2/2010 | Cascao |
| 2010/0099597 | A1 | 4/2010 | Bisgard-Frantzen et al. |
| 2010/0099598 | A1 | 4/2010 | Bisgard-Frantzen et al. |
| 2010/0190681 | A1 | 7/2010 | Thisted et al. |

FOREIGN PATENT DOCUMENTS

| | | |
|---|---|---|
| EP | 0063909 | 11/1982 |
| EP | 0135138 | 3/1985 |
| EP | 0218272 | 4/1987 |
| EP | 0238023 | 9/1987 |
| EP | 0238216 | 9/1987 |
| EP | 0252666 | 1/1988 |
| EP | 0252730 | 1/1988 |
| EP | 0258068 | 3/1988 |
| EP | 0260105 | 3/1988 |
| EP | 0305216 | 3/1989 |
| EP | 0331376 | 9/1989 |
| EP | 0407225 | 1/1991 |
| EP | 1199356 | 4/2002 |
| EP | 1538155 | 6/2005 |
| EP | 0815208 | 8/2006 |
| EP | 1423513 | 11/2009 |
| GB | 1296839 | 11/1972 |
| GB | 1372034 | 10/1974 |
| GB | 1483591 | 8/1977 |
| JP | 64/074992 | 3/1989 |
| WO | WO84/02921 | 8/1984 |
| WO | WO86/01831 | 3/1986 |
| WO | WO89/06270 | 7/1989 |
| WO | WO89/06279 | 7/1989 |
| WO | WO89/09259 | 10/1989 |
| WO | WO91/00353 | 1/1991 |
| WO | WO91/17243 | 11/1991 |
| WO | WO92/00381 | 1/1992 |
| WO | WO92/05249 | 4/1992 |
| WO | WO92/06154 | 4/1992 |
| WO | WO92/06165 | 4/1992 |
| WO | WO92/06221 | 4/1992 |
| WO | WO92/19708 | 11/1992 |
| WO | WO92/19709 | 11/1992 |
| WO | WO92/19729 | 11/1992 |
| WO | WO93/24618 | 12/1993 |
| WO | WO94/01541 | 1/1994 |
| WO | WO94/02597 | 2/1994 |
| WO | WO94/18314 | 8/1994 |
| WO | WO94/25578 | 11/1994 |
| WO | WO94/25583 | 11/1994 |
| WO | WO95/02044 | 1/1995 |
| WO | WO95/14783 | 2/1995 |
| WO | WO95/10602 | 4/1995 |
| WO | WO95/21247 | 8/1995 |
| WO | WO95/22615 | 8/1995 |
| WO | WO 95/22625 | 8/1995 |
| WO | WO95/26397 | 10/1995 |
| WO | WO95/30744 | 11/1995 |
| WO | WO95/35381 | 12/1995 |
| WO | WO96/00292 | 1/1996 |
| WO | WO96/13580 | 5/1996 |
| WO | WO96/23873 | 8/1996 |
| WO | WO96/28567 | 9/1996 |
| WO | WO96/39528 | 12/1996 |
| WO | WO97/00324 | 1/1997 |
| WO | WO97/04079 | 2/1997 |
| WO | WO97/06775 | 2/1997 |
| WO | WO97/07202 | 2/1997 |
| WO | WO97/07205 | 2/1997 |
| WO | WO97/42825 | 11/1997 |
| WO | WO97/43424 | 11/1997 |
| WO | WO98/15257 | 4/1998 |
| WO | WO98/20115 | 5/1998 |
| WO | WO98/20116 | 5/1998 |
| WO | WO98/23732 | 6/1998 |
| WO | WO98/34946 | 8/1998 |
| WO | WO99/19467 | 4/1999 |
| WO | WO99/20770 | 4/1999 |
| WO | WO99/28448 | 6/1999 |
| WO | WO00/04136 | 1/2000 |
| WO | WO00/60060 | 10/2000 |
| WO | WO01/14629 | 3/2001 |
| WO | WO01/34899 | 5/2001 |
| WO | WO02/10355 | 2/2002 |
| WO | WO02/14490 | 2/2002 |
| WO | WO02/092797 | 11/2002 |
| WO | WO2004/091544 | 10/2004 |
| WO | WO2004/113551 | 12/2004 |
| WO | WO2005/056782 | 6/2005 |
| WO | WO2005/056783 | 6/2005 |
| WO | WO2005/111203 | 11/2005 |
| WO | WO2006/002643 | 1/2006 |
| WO | WO2008/153925 | 12/2008 |
| WO | WO2009/061380 | 5/2009 |

OTHER PUBLICATIONS

UniProt Accession No. Q12N92, Shewanella denitrificans (strain OS217 / ATCC BAA-1090/DSM 15013, Alpha amylase, catalytic region, Copeland, A., et al., Aug. 22, 2006.

Accession No. ADW21548, Alpha-amylase for starch hydrolysis, SEQ ID No:18, Viksoe-Nielson, A., et al., Mar. 24, 2005.

UniProt Accession No. Q59222, *Bacillus* sp. TS-23, Lin, L.-L., et al, Nov. 1, 1996.

Gray, G.L., et al. "Structural Genes Encoding the Thermophilic α-amylase of *Bacillus stearothermophilus* and *Bacillus licheniformis*." *Journal of Bacteriology*, 166(2): 635-643, 1986.

Holm, L., et al., "Random Mutagenesis Used to Prove the Structure and Function of *Bacillus Stearothermophilus* Alpha Amylase." *Prot. Eng.* 3(3): 181-191, 1990.

Kim, M.-S., et al., "Changes in Optimum pH and Thermostability of α-Amylase from *Bacillus Licheniformis* by Site-Directed Mutagenesis of His 235 and Asp 328." *Bulletin of the Korean Chemical Society*, 15(10): 832-835, 1994.

Lin, L.-L., et al., "General characteristics of thermostable amylopullulanases and amylases from the alkalophilic *Bacillus* sp. TS-23." *Appl. Microbiol. Biotechnol.* 42: 51-56, 1994.

Lin, L.-L., et al., "Impact of Arg210-Ser211 deletion of thermostability of a truncated *Bacillus* sp. Strain TS-23 α-amylase." *Process Biochemistry* 43: 559-565, 2008.

Lin, L.-L., et al., "Production and properties of a raw-starch-degrading amylase from the thermophilic and alkaliphilic *Bacillus* sp. TS-23," *Biotechnol. Appl. Biochem.* 28: 61-68, 1998.

Nielsen, J.E., et al., "Protein Engineering of bacterial α-amylases." *Biochimica et Biophysica Acta* 1543(2): 253-274, 2000.

Seffernick, J.L., et al., "Melamine Deaminase and Atrazine Chlorohydrolase: 98 Percent Identical but Functionally Different." *J. Bacteriol.* 183(8): 2405-2410, 2001.

Tomazic, S.J., et al., "Why Is One Bacillus α-Amylase More Resistant Against Irreversible Thermoinactivation Than Another ?".*Journal of Biological Chemistry* 263(7): 3092-3096, 1988.

Tsukamoto, A., et al. "Nucleotide sequence of the maltohexaose-producing amylase gene from an alkalophilic *Bacillus* sp. #707 and structural similarity to liquefying type α-amylases." *Biochemical and Biophysical Research Communications* 151(1): 25-31, 1988.

Whisstock, J.C., et al., "Prediction of protein function from protein sequence." *Q. Rev. Biophys.* 36(3): 307-340, 2003.

International Search Report and the Written Opinion of the International Searching Authority for International Application No. PCT/US2008/012410, mailed May 13, 2009.

(56) References Cited

OTHER PUBLICATIONS

International Search Report and the Written Opinion of the International Searching Authority for International Application No. PCT/US2008/012411, mailed Jul. 7, 2009.

International Search Report and the Written Opinion of the International Searching Authority for International Application No. PCT/US2008/012412, mailed Jul. 21, 2009.

International Search Report and the Written Opinion of the International Searching Authority for International Application No. PCT/US2008/012413, mailed Sep. 30, 2009.

U.S. Appl. No. 11/583,334, filed Oct. 19, 2006, Wolfgang et al.

Li, Y., et al., "Effect of introducing proline residues on the stability of *Aspergillus awamori*." *Protein Eng.* 10(10): 1199-1204, 1997.

Lin, L-L., et al., "Production and properties of a raw-starch-degrading amylase from the thermophilic and alkaliphilic *Bacillus* sp. TS-23." *Biotechnol. Appl. Biochem.* 28: 61-68, 1998.

Suzuki, Y., et al., "Amino Acid Residues Stabilizing a *Bacillus* α-Amylase against Irreversible Thermoactivation." *Journal of Biological Chemistry* 264(32): 18933-18938, 1989.

International Search Report and the Written Opinion of the International Searching Authority for International Application No. PCT/US2009/033027 dated Mar. 4, 2010.

International Preliminary Report on Patentability for International Application No. PCT/US2009/033027 dated Aug. 10, 2010.

\* cited by examiner

SEQ ID NO: 1

Sequence of AmyTS23 (full-length molecule, mature chain; 583 amino acids; no signal sequence):

ntapinetmmqyfewdlpndgtlwtkvkneaanlsslgitalwlppaykgtsq
sdvgygvydlydlgefnqkgtirtkygtktqyiqaiqaakaagmqvyadvvfn
hkagadgtefvdavevdpsnrnqetsgtyqiqawtkfdfpgrgntyssfkwrw
yhfdgtdwdesrklnriykfrstgkawdwevdtengnydylmfadldmdhpev
vtelknwgtwyvnttnidgfrldavkhikysffpdwltyvrnqtgknlfavge
fwsydvnklhnyitktngsmslfdaplhnnfytaskssgyfdmryllnntlmk
dqpslavtlvdnhdtqpgqslqswvepwfkplayafiltrqegypcvfygdyy
gipkynipglkskidpllarrdyaygtqrdyidhqdiigwtregidtkpnsg
laalitdgpggskwmyvgkkhagkvfydltgnrsdtvtinadgwgefkvnggs
vsiwvaktsnvtftvnnatttsgqnvyvvanipelgnwntanaikmnpssypt
wkatialpqgkaiefkfikkdqagnviwestsnrtytvpfsstgsytaswnvp

Figure 1

SEQ ID NO: 2

Sequence of AmyTS23t (truncated molecule, mature chain):

ntapinetmmqyfewdlpndgtlwtkvkneaanlsslgitalwlppaykgtsq
sdvgygvydlydlgefnqkgtirtkygtktqyiqaiqaakaagmqvyadvvfn
hkagadgtefvdavevdpsnrnqetsgtyqiqawtkfdfpgrgntyssfkwrw
yhfdgtdwdesrklnriykfrstgkawdwevdtengnydylmfadldmdhpev
vtelknwgtwyvnttnidgfrldavkhikysffpdwltyvrnqtgknlfavge
fwsydvnklhnyitktngsmslfdaplhnnfytaskssgyfdmryllnntlmk
dqpslavtlvdnhdtqpgqslqswvepwfkplayafiltrqegypcvfygdyy
gipkynipglkskidpllarrdyaygtqrdyidhqdiigwtregidtkpnsg
laalitdgpggskwmyvgkkhagkvfydltgnrsdtvtinadgwgefkvnggs
vsiwvak

Figure 2

SEQ ID NO: 3

DNA sequence of optimized AmyTS23 gene:

aatacggcgccgatcaacgaaacgatgatgcagtattttgaatgggatctgccgaatg
atggaacgctgtggacgaaagtcaaaaacgaagcggcgaatcttagcagcctgggaat
cacagcactttggcttccgccggcatataaaggaacgagccaaagcgatgtcggctat
ggcgtctatgatctgtatgacctgggcgaatttaaccaaaaaggcacgatccggacga
atatggcacgaaaacacagtatatccaagcgatccaggcagcaaaagcagcaggcat
gcaagtctatgccgacgtcgtctttaatcataaagcgggagcggatggcacagaattt
gtcgatgccgtcgaagttgatccgagcaacagaaaccaagaaacgagcggcacgtatc
aaatccaagcgtggacgaaatttgattttccgggcagaggcaatacgtatagcagctt
taaatggcgctggtatcattttgacggcacggattgggatgaaagcagaaaactgaac
cggatctataaatttcggagcacgggcaaagcatgggattgggaagtcgatacggaaa
acggcaactatgactatctgatgtttgccgatctggatatggatcatccggaagtcgt
cacggaactgaaaaattggggcacgtggtatgttaatacgacgaacatcgatggcttt
agactggatgccgtcaaacatatcaaatatagcttttttccggactggctgacgtatg
tcagaaaccagacgggcaaaaacctttttgccgtcggcgaattttggagctatgacgt
caacaaacttcataactatatcacgaaaacgaacggcagcatgagccttttttgatgcc
ccgcttcataacaacttttatacggcgagcaaaagctcaggctattttgatatgagat
atctgctgaacaacacgctgatgaaagatcaaccgagcctggcagtcacactggtcga
taccatgatacacaaccgggccaaagccttcaaagctgggtcgaaccgtggttt aaa
ccgctggcgtatgcctttatcctgacgagacaagaagggtatccttgcgtcttttatg
gcgactattatggcatcccgaaatataatatcccgggcctgaaaagcaaaatcgatcc
gctgctgatcgccagacgggattatgcctatggcacacagcgggattatatcgaccat
caggacatcatcggctggacaagagaaggcatcgatacgaaaccgaatagcggactgg
cagcactgattacagatggaccgggcggaagcaaatggatgtatgtcggcaaaaaaca
tgccggcaaagtcttttatgatctgacgggcaacagaagcgatacggtcacgatcaat
gctgatggctggggagaatttaaagtcaatggcggcagcgtttcaatctgggtcgcca
aaacgagcaatgtcacgtttacggtcaacaatgccacgacaacgagcggccaaaatgt
ctatgtcgtcgccaatatcccggaactgggcaattggaatacggcgaacgcaatcaaa
atgaacccgagcagctatccgacatggaaagcgacaatcgctctgccgcaaggaaaag
cgatcgaatttaaatttatcaaaaaagaccaggcgggcaatgttatttgggaaagcac
gagcaatagaacgtatacggtcccgtttagcagcacaggaagctatacagcgagctgg
aatgttccgtga

Figure 3

SEQ ID NO: 4

DNA sequence of optimized AmyTS23t gene:

aatacggcgccgatcaacgaaacgatgatgcagtattttgaatgggatctgccgaatg
atggaacgctgtggacgaaagtcaaaaacgaagcggcgaatcttagcagcctgggaat
cacagcactttggcttccgccggcatataaaggaacgagccaaagcgatgtcggctat
ggcgtctatgatctgtatgacctgggcgaatttaaccaaaaaggcacgatccggacga
aatatggcacgaaaacacagtatatccaagcgatccaggcagcaaaagcagcaggcat
gcaagtctatgccgacgtcgtctttaatcataaagcgggagcggatggcacagaattt
gtcgatgccgtcgaagttgatccgagcaacagaaaccaagaaacgagcggcacgtatc
aaatccaagcgtggacgaaatttgattttccgggcagaggcaatacgtatagcagctt
taaatggcgctggtatcattttgacggcacggattgggatgaaagcagaaaactgaac
cggatctataaatttcggagcacgggcaaagcatgggattgggaagtcgatacggaaa
acggcaactatgactatctgatgtttgccgatctggatatggatcatccggaagtcgt
cacggaactgaaaaattggggcacgtggtatgttaatacgacgaacatcgatggcttt
agactggatgccgtcaaacatatcaaatatagcttttttccggactggctgacgtatg
tcagaaaccagacgggcaaaaaccttttgccgtcggcgaattttggagctatgacgt
caacaaacttcataactatatcacgaaaacgaacggcagcatgagccttttttgatgcc
ccgcttcataacaacttttatacggcgagcaaaagctcaggctattttgatatgagat
atctgctgaacaacacgctgatgaaagatcaaccgagcctggcagtcacactggtcga
taaccatgatacacaaccgggccaaagccttcaaagctgggtcgaaccgtggtttaaa
ccgctggcgtatgcctttatcctgacgagacaagaagggtatccttgcgtcttttatg
gcgactattatggcatcccgaaatataatatcccgggcctgaaaagcaaaatcgatcc
gctgctgatcgccagacgggattatgcctatggcacacagcgggattatatcgaccat
caggacatcatcggctggacaagagaaggcatcgatacgaaaccgaatagcggactgg
cagcactgattacagatggaccgggcggaagcaaatggatgtatgtcggcaaaaaaca
tgccggcaaagtcttttatgatctgacgggcaacagaagcgatacggtcacgatcaat
gctgatggctggggagaatttaaagtcaatggcggcagcgtttcaatctgggtcgcca
aatga

Figure 4

SEQ ID NO: 5
Coding region for the LAT signal peptide
ATGAAACAACAAAAACGGCTTTACGCCCGATTGCTGACGCTGTTATTTGCGCT
CATCTTCTTGCTGCCTCATTCTGCAGCTTCAGCA

SEQ ID NO: 6
Amino acid sequence of the LAT signal peptide
MKQQKRLYARLLTLLFALIFLLPHSAASA

SEQ ID NO: 7
Primer pHPLT-PstI-FW
CTCATTCTGCAGCTTCAGCAAATACGGCG

SEQ ID NO: 8
Primer pHPLT-HpaI-RV
CTCTGTTAACTCATTTGGCGACCCAGATTGAAACG

SEQ ID NO: 9
Primer TS-delRS-FW
CTATAAATTTACGGGCAAAGCATGGGATTGG

SEQ ID NO: 10
Primer TS-delRS-RV
TGCTTTGCCCGTAAATTTATAGATCCGGTTCAG

SEQ ID NO: 11
Primer TS-M201L-FW
CTATGACTATCTGCTGTTTGCCGATCTG

SEQ ID NO: 12
Primer TS-M201L-RV
CAGATCGGCAAACAGCAGATAGTCATAG

SEQ ID NO: 13
Primer TS-delRS/M201L-FW
GCATGGGATTGGGAAGTCGATACGGAAAACGGCAACTATGACTATCTGCTGT
TTGCCG

SEQ ID NO: 14
Primer TS-delRS/M201L-RV
CGTATCGACTTCCCAATCCCATGCTTTGCCCGTAAATTTATAGATCCGGTTC

Figure. 14

SEQUENCE LISTING

```
<160> NUMBER OF SEQ ID NOS: 14

<210> SEQ ID NO 1
<211> LENGTH: 583
<212> TYPE: PRT
<213> ORGANISM: Bacillus sp. TS-23

<400> SEQUENCE: 1

Asn Thr Ala Pro Ile Asn Glu Thr Met Met Gln Tyr Phe Glu Trp Asp
  1               5                  10                  15

Leu Pro Asn Asp Gly Thr Leu Trp Thr Lys Val Lys Asn Glu Ala Ala
             20                  25                  30

Asn Leu Ser Ser Leu Gly Ile Thr Ala Leu Trp Leu Pro Pro Ala Tyr
         35                  40                  45

Lys Gly Thr Ser Gln Ser Asp Val Gly Tyr Gly Val Tyr Asp Leu Tyr
     50                  55                  60

Asp Leu Gly Glu Phe Asn Gln Lys Gly Thr Ile Arg Thr Lys Tyr Gly
 65                  70                  75                  80

Thr Lys Thr Gln Tyr Ile Gln Ala Ile Gln Ala Ala Lys Ala Ala Gly
                 85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300
```

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
            325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
        370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
            405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
            485                 490                 495

Thr Thr Ser Gly Gln Asn Val Tyr Val Val Ala Asn Ile Pro Glu Leu
            500                 505                 510

Gly Asn Trp Asn Thr Ala Asn Ala Ile Lys Met Asn Pro Ser Ser Tyr
            515                 520                 525

Pro Thr Trp Lys Ala Thr Ile Ala Leu Pro Gln Gly Lys Ala Ile Glu
            530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
            565                 570                 575

Thr Ala Ser Trp Asn Val Pro
            580

<210> SEQ ID NO 2
<211> LENGTH: 484
<212> TYPE: PRT
<213> ORGANISM: Bacillus sp. TS-23

<400> SEQUENCE: 2

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
            85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Gly Leu Lys Ser Lys
    370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
                405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
        435                 440                 445

Val Phe Tyr Asp Leu Thr Gly Asn Arg Ser Asp Thr Val Thr Ile Asn
    450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 3
<211> LENGTH: 1752
<212> TYPE: DNA

<213> ORGANISM: Artificial
<220> FEATURE:
<223> OTHER INFORMATION: synthetic optimized AmyTS23 gene

<400> SEQUENCE: 3

```
aatacggcgc cgatcaacga aacgatgatg cagtattttg aatgggatct gccgaatgat      60
ggaacgctgt ggacgaaagt caaaaacgaa gcggcgaatc ttagcagcct gggaatcaca     120
gcactttggc ttccgccggc atataaagga acgagccaaa gcgatgtcgg ctatggcgtc     180
tatgatctgt atgacctggg cgaatttaac caaaaaggca cgatccggac gaaatatggc     240
acgaaaacac agtatatcca agcgatccag gcagcaaaag cagcaggcat gcaagtctat     300
gccgacgtcg tctttaatca taaagcggga gcggatggca cagaatttgt cgatgccgtc     360
gaagttgatc cgagcaacag aaaccaagaa acgagcggca cgtatcaaat ccaagcgtgg     420
acgaaatttg attttccggg cagaggcaat acgtatagca gctttaaatg cgcgctggta     480
cattttgacg gcacggattg ggatgaaagc agaaaactga accggatcta taaatttcgg     540
agcacgggca agcatggga ttgggaagtc gatacgaaaa acggcaacta tgactatctg     600
atgtttgccg atctggatat ggatcatccg gaagtcgtca cggaactgaa aaattggggc     660
acgtggtatg ttaatacgac gaacatcgat ggctttagac tggatgccgt caaacatatc     720
aaatatagct tttttccgga ctggctgacg tatgtcagaa accagacggg caaaaacctt     780
tttgccgtcg cgaattttg gagctatgac gtcaacaaac ttcataacta tatcacgaaa     840
acgaacggca gcatgagcct ttttgatgcc ccgcttcata caacttttta tacggcgagc     900
aaaagctcag gctattttga tatgagatat ctgctgaaca cacgctgat gaaagatcaa     960
ccgagcctgg cagtcacact ggtcgataac catgatacac aaccgggcca agccttcaa    1020
agctgggtca accgtggtt taaaccgctg gcgtatgcct ttatcctgac gagacaagaa    1080
gggtatcctt gcgtctttta tggcgactat tatggcatcc gaaatataa tatcccgggc    1140
ctgaaaagca aaatcgatcc gctgctgatc gccagacggg attatgccta tgcacacag    1200
cgggattata tcgaccatca ggacatcatc ggctggacaa gagaaggcat cgatacgaaa    1260
ccgaatagcg gactggcagc actgattaca gatggaccgg gcggaagcaa atggatgtat    1320
gtcggcaaaa acatgccgg caaagtcttt tatgatctga cgggcaacag aagcgatacg    1380
gtcacgatca atgctgatgg ctggggagaa tttaaagtca atggcggcag cgtttcaatc    1440
tgggtcgcca aaacgagcaa tgtcacgttt acggtcaaca atgccacgac aacgagcggc    1500
caaaatgtct atgtcgtcgc caatatcccg gaactgggca attggaatac ggcgaacgca    1560
atcaaaatga acccgagcag ctatccgaca tggaaagcga caatcgctct gccgcaagga    1620
aaagcgatcg aatttaaatt tatcaaaaaa gaccaggcgg gcaatgttat ttgggaaagc    1680
acgagcaata gaacgtatac ggtcccgttt agcagcacag gaagctatac agcgagctgg    1740
aatgttccgt ga                                                       1752
```

<210> SEQ ID NO 4
<211> LENGTH: 1455
<212> TYPE: DNA
<213> ORGANISM: Artificial
<220> FEATURE:
<223> OTHER INFORMATION: synthetic optimized AmyTS23 gene

<400> SEQUENCE: 4

```
aatacggcgc cgatcaacga aacgatgatg cagtattttg aatgggatct gccgaatgat      60
ggaacgctgt ggacgaaagt caaaaacgaa gcggcgaatc ttagcagcct gggaatcaca     120
```

```
gcactttggc ttccgccggc atataaagga acgagccaaa gcgatgtcgg ctatggcgtc    180
tatgatctgt atgacctggg cgaatttaac caaaaaggca cgatccggac gaaatatggc    240
acgaaaacac agtatatcca agcgatccag gcagcaaaag cagcaggcat gcaagtctat    300
gccgacgtcg tctttaatca taaagcggga gcggatggca cagaatttgt cgatgccgtc    360
gaagttgatc cgagcaacag aaaccaagaa acgagcggca cgtatcaaat ccaagcgtgg    420
acgaaatttg attttccggg cagaggcaat acgtatagca gctttaaatg cgctggtat    480 cattttgacg gcacggattg ggatgaaagc agaaaactga accggatcta taaatttcgg    540
agcacgggca agcatgggat tgggaagtc gatacgaaaa acggcaacta tgactatctg    600
atgtttgccg atctggatat ggatcatccg gaagtcgtca cggaactgaa aaattggggc    660
acgtggtatg ttaatacgac gaacatcgat ggctttagac tggatgccgt caaacatatc    720
aaatatagct ttttccgga ctggctgacg tatgtcagaa accagacggg caaaaacctt    780
tttgccgtcg gcgaattttg gagctatgac gtcaacaaac ttcataacta tatcacgaaa    840
acgaacggca gcatgagcct ttttgatgcc ccgcttcata caacttttta tacggcgagc    900
aaaagctcag gctattttga tatgagatat ctgctgaaca cacgctgat gaaagatcaa    960 ccgagcctgg cagtcacact ggtcgataac catgatacac aaccgggcca agccttcaa   1020 agctgggtcg aaccgtggtt taaaccgctg gcgtatgcct ttatcctgac gagacaagaa   1080
gggtatcctt gcgtcttta tggcgactat tatggcatcc cgaaatataa tatcccggc   1140 ctgaaaagca aaatcgatcc gctgctgatc gccagacggg attatgccta tggcacacag   1200
cgggattata tcgaccatca ggacatcatc ggctggacaa gagaaggcat cgatacgaaa   1260
ccgaatagcg gactggcagc actgattaca gatggaccgg gcggaagcaa atggatgtat   1320
gtcggcaaaa acatgccgg caaagtcttt tatgatctga cgggcaacag aagcgatacg   1380
gtcacgatca atgctgatgg ctggggagaa tttaaagtca atggcggcag cgtttcaatc   1440
tgggtcgcca aatga                                                   1455

<210> SEQ ID NO 5
<211> LENGTH: 87
<212> TYPE: DNA
<213> ORGANISM: Bacillus lichenformis

<400> SEQUENCE: 5
atgaaacaac aaaaacggct ttacgcccga ttgctgacgc tgttatttgc gctcatcttc     60
ttgctgcctc attctgcagc ttcagca                                        87

<210> SEQ ID NO 6
<211> LENGTH: 29
<212> TYPE: PRT
<213> ORGANISM: Bacillus lichenformis

<400> SEQUENCE: 6

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala
            20                  25

<210> SEQ ID NO 7
<211> LENGTH: 29
<212> TYPE: DNA
<213> ORGANISM: Artificial
<220> FEATURE:
```

-continued

<223> OTHER INFORMATION: synthetic primer

<400> SEQUENCE: 7
ctcattctgc agcttcagca aatacggcg                                29

<210> SEQ ID NO 8
<211> LENGTH: 35
<212> TYPE: DNA
<213> ORGANISM: Artificial
<220> FEATURE:
<223> OTHER INFORMATION: synthetic primer

<400> SEQUENCE: 8
ctctgttaac tcatttggcg acccagattg aaacg                         35

<210> SEQ ID NO 9
<211> LENGTH: 31
<212> TYPE: DNA
<213> ORGANISM: Artificial
<220> FEATURE:
<223> OTHER INFORMATION: synthetic primer

<400> SEQUENCE: 9
ctataaattt acgggcaaag catgggattg g                             31

<210> SEQ ID NO 10
<211> LENGTH: 33
<212> TYPE: DNA
<213> ORGANISM: Artificial
<220> FEATURE:
<223> OTHER INFORMATION: synthetic primer

<400> SEQUENCE: 10
tgctttgccc gtaaatttat agatccggtt cag                           33

<210> SEQ ID NO 11
<211> LENGTH: 28
<212> TYPE: DNA
<213> ORGANISM: Artificial
<220> FEATURE:
<223> OTHER INFORMATION: synthetic primer

<400> SEQUENCE: 11
ctatgactat ctgctgtttg ccgatctg                                 28

<210> SEQ ID NO 12
<211> LENGTH: 28
<212> TYPE: DNA
<213> ORGANISM: Artificial
<220> FEATURE:
<223> OTHER INFORMATION: synthetic primer

<400> SEQUENCE: 12
cagatcggca aacagcagat agtcatag                                 28

<210> SEQ ID NO 13
<211> LENGTH: 58
<212> TYPE: DNA
<213> ORGANISM: Artificial
<220> FEATURE:
<223> OTHER INFORMATION: synthetic primer

<400> SEQUENCE: 13
gcatgggatt gggaagtcga tacggaaaac ggcaactatg actatctgct gtttgccg    58

```
<210> SEQ ID NO 14
<211> LENGTH: 52
<212> TYPE: DNA
<213> ORGANISM: Artificial
<220> FEATURE:
<223> OTHER INFORMATION: synthetic primer

<400> SEQUENCE: 14
cgtatcgact tcccaatccc atgctttgcc cgtaaattta tagatccggt tc          52
```

TS-23 ALPHA-AMYLASE VARIANTS WITH ALTERED PROPERTIES

PRIORITY

The present application is a continuation of U.S. patent application Ser. No. 13/540,064, filed Jul. 2, 2012, now U.S. Pat. No. 8,460,916, which is a divisional of U.S. patent application Ser. No. 12/365,646, filed Feb. 4, 2009, now U.S. Pat. No. 8,236,545, which claims priority to U.S. Provisional Patent Application Ser. Nos. 61/026,056, filed on Feb. 4, 2008, and 61/059,403, filed on Jun. 6, 2008, which are hereby incorporated by reference in their entireties.

SEQUENCE LISTING

The sequence listing submitted via EFS, in compliance with 37 C.F.R. §1.52(e), is incorporated herein by reference. The sequence listing text file submitted via EFS contains the file 31066-D1-C1-US-seqlist.txt" created on May 16, 2013, which is 15,844 bytes in size.

TECHNICAL FIELD

Described are compositions and methods relating to variants of TS-23 alpha-amylase (α-amylase), which variants have altered biochemical properties and advantageous performance characteristics with respect to the parent amylase. The variants are suitable for use in, e.g., starch conversion, ethanol production, laundry and dishwashing, hard surface cleaning, textile desizing, and/or sweetener production.

BACKGROUND

Starch is of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units. Its MW may be as high as 100 million.

Sugars from starch, in the form of concentrated dextrose syrups, are currently produced by an enzyme catalyzed process involving: (1) liquefaction (or thinning) of solid starch with an α-amylase into dextrins having an average degree of polymerization of about 7-10; and (2) saccharification of the resulting liquefied starch (i.e. starch hydrolysate) with amyloglucosidase (also called glucoamylase or GA). The resulting syrup has a high glucose content. Much of the glucose syrup, which is commercially produced, is subsequently enzymatically isomerized to a dextrose/fructose mixture known as isosyrup.

Alpha (α)-Amylases (α-1,4-glucan-4-glucanohydrolases, E.C. 3.2.1.1) are a group of enzymes that hydrolyze starch, glycogen, and related polysaccharides by cleaving internal α-1,4-glucosidic bonds at random. This enzyme class has a number of important commercial applications in, for example, in the initial stages (liquefaction) of starch processing, in textile desizing, in deinking of recycled paper, in starch modification in the paper and pulp industry, in wet corn milling, in alcohol production, in sweetener (e.g., sugar) manufacture, in the beverage industry, in brewing, in oilfields, in animal feed, and as cleaning agents in detergent matrices. For example, such enzymes can be used to remove starchy stains during dishwashing and laundry washing.

α-amylases are isolated from a wide variety of bacterial, fungal, plant and animal sources. Industrially, many important α-amylases are those isolated from Bacilli. One characterized α-amylase is that of an alkaliphilic Bacillus sp. strain TS-23 which produces at least five kinds of enzymes exhibiting starch hydrolyzing activity. (Lin et al., 1998, Production and properties of a raw-starch-degrading amylase from the thermophilic and alkaliphilic Bacillus sp. TS-23, Biotechnol. Appl. Biochem. 28:61-68). The α-amylase of Bacillus sp. no. TS-23 has a pH optimum of 9 although it is stable over a broad pH range (i.e., pH 4.7 to 10.8). Its temperature optimum is 45° C., although the enzyme has activity at lower temperatures, e.g., 15-20° C.

There remains a need for variant α-amylases that posses altered biochemical characteristics and offer improved performance in the industrial applications.

SUMMARY

Described are variants (mutants) of a TS-23 α-amylase that exhibit altered properties which are advantageous in connection with various industrial processes such as processing of starch (e.g., starch liquefaction, saccharification, and the like), textile (e.g., desizing), and as additives to detergents (e.g., for cleaning starch-based stains).

The alterations include but are not limited to alterations in specific activity, substrate specificity, substrate binding, the substrate cleavage pattern, thermal stability, stability towards oxidation, $Ca^{2+}$ dependency, the pH/activity profile, the pH/stability profile, and other properties of interest. An exemplary altered pH/stability profile is increased stability at low pH (e.g., pH<6 and even pH<5) and/or increased stability at high pH, (e.g. pH>9).

In one aspect, a variant of a parent AmyTS23 α-amylase is provided that has an amino acid sequence which has at least about 80%, 81%, 82%, 83%, 84%, 85%, 86%, 87%, 88%, 89%, 90%, 91%, 92%, 93%, 94%, 95%, 96%, 97%, 98%, or even 99% identity to the parent α-amylase and comprises at least two of the following: (a) truncation of the C-terminus, (b) substitution of amino acid 201, or (c) deletion of residues R180 and S181 and wherein the variant has α-amylase activity (using SEQ ID NO:1 for numbering). In some embodiments, the parent α-amylase is SEQ ID NO: 1. In some embodiments, the parent α-amylase has a specified homology to SEQ ID NO: 1

Another aspect contemplates a manual or automatic dishwashing composition comprising a Bacillus sp. no. TS-23 α-amylase, or variant thereof. The composition may further comprise one or more of a surfactant, detergent builder, a complexing agent, a polymer, a bleaching system, a stabilizer, a foam booster, a suds suppressor, an anti-corrosion agent, a soil-suspending agent, an anti-soil redeposit ion agent, a dye, a bactericide, a hydrotope, a tarnish inhibitor, and a perfume. The dishwashing compositions can be a composition used for manual or automatic dishwashing.

A related aspect contemplates a laundry detergent additive comprising a Bacillus sp. no. TS-23 α-amylase, or variant thereof. As above, the composition may further comprise one or more of a surfactant, detergent builder, a complexing agent, a polymer, a bleaching system, a stabilizer, a foam booster, a suds suppressor, an anti-corrosion agent, a soil-suspending agent, an anti-soil redeposition agent, a dye, a bactericide, a hydrotope, a tarnish inhibitor, and a perfume. The composition may also comprise one or more of a surfactant, detergent builder, a complexing agent, a polymer, a bleaching system, a stabilizer, a foam booster, a suds suppressor, an anti-corrosion agent, a soil-suspending agent, an anti-soil redeposition agent, a dye, a bactericide, a hydrotope, an optical brightener, a fabric conditioner, and a perfume.

A further aspect relates to a nucleic acid encoding the described variants and to vectors comprising such nucleic acids. Also contemplated are cells in which such nucleic acids are inserted, for example via a vector, phage, or virus. The isolated host cell can be a microorganism for example such as a bacterium or fungus. The bacterium can be a Gram positive bacterium selected from the group consisting of *Bacillus subtilis, B. licheniformis, B. lentus, B. brevis, G. stearothermophilus* (previously called *B. stearothermophilus*), *B. alkalophilus, B. amyloliquefaciens, B. coagulans, B. circulans, B. lautus, B. thuringiensis, Streptomyces lividans* or *S. murinus*; or a Gram negative bacterium, wherein said Gram negative bacterium is *Escherichia coli* or a *Pseudomonas* species.

Other aspects relate to a method for preparing the variant polypeptides, and to the use of the variant polypeptides, alone or in combination with other enzymes, including α-amylolytic enzymes, in various industrial processes, such as starch liquefaction. Some aspects contemplate the use of the variant polypeptides for laundry washing and/or dishwashing. Also contemplated are methods of cleaning textiles and or other hard surfaces using the variant polypeptides. Another aspect contemplates the use of the α-amylase described herein or any of the α-amylase variants in a textile desizing composition, e.g., wherein the composition is an aqueous solution. Also contemplated are methods of desizing textiles using said compositions.

The variant polypeptides can optionally be in the form of a non-dusting granulate, microgranulate, stabilized liquid, or protected enzyme. Another aspect contemplates that the detergent additive or detergent composition further comprise an enzyme selected from the group consisting of: a cellulase, a protease, an acyltransferase, an aminopeptidase, an amylase, a carbohydrase, a carboxypeptidase, a catalase, a chitinase, a cutinase, a cyclodextrin glycotransferase, a deoxyribonuclease, an esterase, an α-galactosidase, a β-galactosidase, a glucoamylase, α-glucosidase, a β-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, a xylanase, a pullulanase, an isoamylase, a carrageenase, or any combination of the enzymes. Other amylases contemplated for use in the composition include two or more other α-amylases, a β-amylase, an isoamylase, or a glucoamylase.

Some aspects contemplate a composition for starch processing comprising a *Bacillus* sp. no. TS-23 α-amylase, or variant thereof, in an aqueous solution. Also contemplated is a method of using such a composition to process starch. The method and composition may further comprise a glucoamylase, an isoamylase, a pullulanase, phytase or a combination thereof. Yet another aspect contemplates a biofilm degrading (e.g., hydrolyzing) composition comprising a *Bacillus* sp. no. TS-23 α-amylase or variant thereof in a solution or gel, and optionally further comprising a cellulase, a hemicellulase, a xylanase, a lipase, a protease, a pectinase, an antimicrobial agent, or any combination thereof. Also contemplated are methods of hydrolyzing biofilms using said compositions.

Another aspect contemplated is a composition for saccharifying starch comprising a *Bacillus* sp. no. TS-23 α-amylase or variant thereof in a solution. Therefore, also contemplated is a method of saccharifying starch comprising administering the composition containing the amylases described herein for a period sufficient to saccharify said starch.

Another aspect contemplated is a composition for liquefying starch comprising a *Bacillus* sp. no. TS-23 α-amylase or variant thereof in a solution. Also contemplated is a method of liquefying a starch comprising administering the composition for a period sufficient to liquefy said starch.

Some particular aspects of the compositions and method are described below.

In one aspect, a variant of a parent AmyTS23 alpha-amylase is provided, wherein the variant has an amino acid sequence which has at least 80% identity to the parent alpha-amylase and comprises at least two of the following:
 (a) a truncation of the C-terminus,
 (b) a substitution of residue 201, or
 (c) a deletion of residues R180 and S181,
wherein said amino acid residues refer to the amino acid sequence of SEQ ID NO:1. In some embodiments, the variant has alpha-amylase activity.

In some embodiments, the variant has at least 90% identity to the parent alpha-amylase. In some embodiments, the variant has at least 95% identity to the parent alpha-amylase. In particular embodiments, the parent alpha-amylase has the amino acid sequence of SEQ ID NO: 1.

In some embodiments, the variant further comprises a substitution at one or more residues selected from the group consisting of residue 87, residue 225, residue 272, and residue 282.

In another aspect, a variant of a parent AmyTS23 alpha-amylase is provided, wherein the variant has an amino acid sequence which has at least 85% identity to the parent alpha-amylase and comprises a truncation of the C-terminus. In some embodiments, the variant has the amino acid sequence of SEQ ID NO: 2. The variant may have increased cleaning activity against starch stains in cold water compared to the parent amylase.

In some embodiments, the variant further comprises a deletion of the residues at position R180 and S181, wherein the amino acid residue positions refer to the amino acid sequence of SEQ ID NO:1. The variant may have increased detergent stability compared to the parent amylase.

In some embodiments, the variant further comprising a substitution of the residue at position 201, wherein the amino acid residue position refers to the amino acid sequence of SEQ ID NO:1. The variant may have increased oxidative stability compared to the parent amylase. The variant may have the substitution M201L.

Any of the may further comprised a substitution at one or more residues selected from the group consisting of residue 87, residue 225, residue 272, and residue 282, wherein the amino acid residue position refers to the amino acid sequence of SEQ ID NO:1.

In a related aspect, a nucleic acid encoding a variant described herein, is provided. In some embodiments, an expression vector comprising this nucleic acid under control of a suitable promoter is provided. In some embodiments, a host cell comprising the expression vector is provided.

In a related aspect, a manual or automatic dishwashing composition comprising a variant described herein and one or more of: a surfactant, detergent builder, a complexing agent, a polymer, a bleaching system, a stabilizer, a foam booster, a suds suppressor, an anti-corrosion agent, a soil-suspending agent, an anti-soil redeposition agent, a dye, a bactericide, a hydrotope, a tarnish inhibitor, and a perfume is provided.

In a related aspect, a laundry detergent additive comprising a variant as described herein and one or more of: a surfactant, detergent builder, a complexing agent, a polymer, a bleaching system, a stabilizer, a foam booster, a suds suppressor, an anti-corrosion agent, a soil-suspending agent, an anti-soil redeposition agent, a dye, a bactericide, a hydrotope, an optical brightener, a fabric conditioner, and a perfume, is provided.

In another aspect, a method for removing starch from a textile is provided, comprising incubating the textile in the presence of a variant of a parent AmyTS23 alpha-amylase, wherein the variant has an amino acid sequence which has at least 80% identity to the parent alpha-amylase and comprises at least two of the following:
(a) a truncation of the C-terminus,
(b) a substitution of residue 201, or
(c) a deletion of residues R180 and S181,
wherein said amino acid residues refer to the amino acid sequence of SEQ ID NO:1, and
wherein said incubating removes the starch from the textile.

In a related aspect, a method for processing starch is provided, comprising incubating the textile in the presence of a variant of a parent AmyTS23 alpha-amylase, wherein the variant has an amino acid sequence which has at least 80% identity to the parent alpha-amylase and comprises at least two of the following:
(a) a truncation of the C-terminus,
(b) a substitution of residue 201, or
(c) a deletion of residues R180 and S181,
wherein said amino acid residues refer to the amino acid sequence of SEQ ID NO:1, and
wherein said incubating hydrolyzes said starch.

These and other aspect and embodiments of the present compositions and method will apparent in view of the disclosure and drawings.

BRIEF DESCRIPTION OF THE DRAWINGS

FIG. 1 shows the amino acid sequence of the parent AmyTS23 amylase (full-length, mature; SEQ ID NO: 1).

FIG. 2 shows the amino acid sequence of the AmyTS23t truncated polypeptide (mature; SEQ ID NO: 2). Bold and underlined text indicates amino acids residues R180, S181 and M201.

FIG. 3 shows the DNA sequence of the optimized amyTS23 gene (SEQ ID NO: 3).

FIG. 4 shows the DNA sequence of the optimized amyTS23t gene (SEQ ID NO: 4).

FIG. 14 shows additional amino acid and nucleotide sequences referred to in the disclosure.

DETAILED DESCRIPTION

Figure 5:
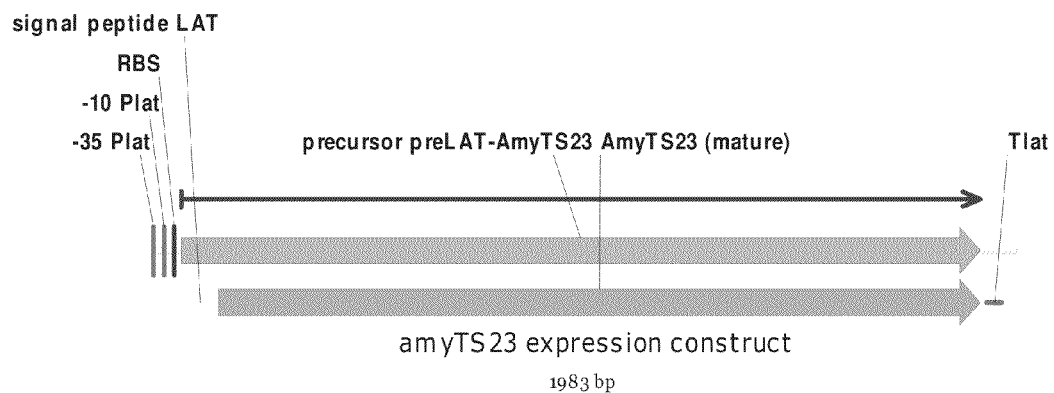
FIG. 5 shows an expression cassette for AmyTS23 and AmyTS23t.

Described are compositions and methods involving *Bacillus* sp. no. TS-23 α-amylase and variants thereof. Variants of TS-23 have altered biochemical characteristics and demonstrate high performance in, e.g., laundry and dishwashing applications. These and other features of the variants, as well as applications for using the variants, will be described in detail.

1. Abbreviations and Definitions

The following abbreviations and definitions apply. The singular forms "a", "an", and "the" include plural referents unless the context clearly dictates otherwise. Thus, for example, reference to "an enzyme" includes a plurality of such enzymes and reference to "the formulation" includes reference to one or more formulations and equivalents thereof known to those skilled in the art, and so forth.

Unless defined otherwise herein, all technical and scientific terms used herein have the same meaning as commonly understood by one of ordinary skill in the art. Singleton, et al., DICTIONARY OF MICROBIOLOGY AND MOLECULAR BIOLOGY, 2D ED., John Wiley and Sons, New York (1994) and Hale & Markham, THE HARPER COLLINS DICTIONARY OF BIOLOGY, Harper Perennial, NY (1991) provide one of skill with general dictionaries of many of the terms used herein.

Some aspects of the compositions and methods rely on routine techniques and methods used in the field of genetic engineering and molecular biology. The following resources include descriptions of general methodology useful in accordance with the present compositions and methods: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). These general references provide definitions and methods known to those in the art. However, it is not intended that the present compositions and methods be limited to any particular techniques, protocols, and reagents described, as these may vary. Although any methods and materials similar or equivalent to those described herein can be used in the practice or testing of the present compositions and methods, the preferred methods and materials are described.

When describing proteins and genes that encode them, the name of the gene is generally italicized and not capitalized, while the name of the protein is generally not italicized and the first letter is capitalized.

All patents and publications referred to herein, including all sequences disclosed within such patents and publications, are expressly incorporated by reference.

1.1 Definitions

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, brans, cassaya, millet, potato, sweet potato, and tapioca.

As used herein, an "amylase" is an enzyme capable of catalyzing the degradation of starch. Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the starch molecule from the non-reducing end of the substrate. β-amylases, α-glucosidases (EC 3.2.1.20; α-D-glucoside glucohydrolase), glucoamylases (EC 3.2.1.3; α-D-(1→4)-glucan glucohydrolase), and product-specific amylases can produce malto-oligosaccharides of a specific length from starch. As used herein, amylases include any/all amylases, including glucoamylases, α-amylases, β-amylases and wild-type α-amylases, such as those of *Bacillus* sp., e.g., *B. licheniformis* and *B. subtilis*.

As used herein, "*Bacillus* sp. strain TS-23 α-amylase," and similar phrases, refer to an α-amylase derived from *Bacillus* sp. strain TS-23. The gene encoding the α-amylase can be the wild-type gene or a codon optimized polynucleotide that encodes the α-amylase. The mature α-amylase of *Bacillus* sp. strain TS-23 is (amino to carboxy orientation) (SEQ ID NO: 1; FIG. 1):

```
ntapinetmm qyfewdlpnd gtlwtkvkne aanlsslgit      50
alwlppaykg tsqsdvgygv ydlydlgefn qkgtirtkyg tktgyiqaiq     100
aakaagmqvy advvfnhkag adgtefvdav evdpsnrnqe tsgtyqiqaw     150
tkfdfpgrgn tyssfkwrwy hfdgtdwdes rklnriykfr stgkawdwev     200
dtengnydyl mfadldmdhp evvtelknwg twyvnttnid gfrldavkhi     250
kysffpdwlt yvrnqtgknl favgefwsyd vnklhnyitk tngsmslfda     300
plhnnfytas kssgyfdmry llnntlmkdq pslavtlvdn hdtqpgqslq     350
swvepwfkpl ayafiltrqe gypcvfygdy ygipkynipg lkskidplli     400
arrdyaygtq rdyidhqdii gwtregidtk pnsglaalit dgpggskwmy     450
vgkkhagkvf ydltgnrsdt vtinadgwge fkvnggsvsi wvaktsnvtf     500
tvnnatttsg qnvyvvanip elgnwntana ikmnpssypt wkatialpqg     550
kaiefkfikk dqagnviwes tsnrtytvpf sstgsytasw nvp            583
```

As used herein, "*Bacillus* sp. strain TS-23 α-amylase variants," and similar phrases, refer to variants/mutants of the wild-type *Bacillus* sp. strain TS-23 α-amylase, which includes an amino acid substitution, insertion, and/or deletion with respect to the parent (wild-type; reference) amino acid sequence of *Bacillus* sp. strain TS-23 amylase. The term "variant" is used interchangeably with the term "mutant". The variant *Bacillus* sp. strain TS-23 α-amylase may include mutations in the signal sequence with respect to parent signal sequence. In addition, the variant *Bacillus* sp. strain TS-23 α-amylase can be in the form of a fusion protein containing a heterologous α-amylase signal sequence, such as from *B. licheniformis* (LAT).

As used herein, the phrases "parent *Bacillus* sp. strain TS-23 α-amylase," "wild-type *Bacillus* sp. strain TS-23 α-amylase," "reference *Bacillus* sp. strain TS-23 α-amylase," and similar phrases, refer to the polypeptide of *Bacillus* sp. strain TS-23. The term may be abbreviated "parent enzyme," "wild-type enzyme," "parent polypeptide," reference polypeptide," or the like, for convenience. The parent *Bacillus* sp. strain TS-23 α-amylase may include mutations in the signal sequence of the parent polypeptide. In addition, the parent *Bacillus* sp. strain TS-23 α-amylase can be in the form of a fusion protein containing a heterologous α-amylase signal sequence, such as from *B. licheniformis* (LAT).

A "parent nucleic acid/polynucleotide," "wild-type nucleic acid/polynucleotide," or "reference nucleic acid/polynucleotide," refers to a nucleic acid sequence encoding a parent polypeptide, and a nucleic acid complementary thereto.

A "variant nucleic acid/polynucleotide" refers to a nucleic acid sequence encoding a variant polypeptide or a nucleic acid complementary thereto, or a polynucleotide sequence having at least one base substitution, insertion, or deletion with respect to a parent polynucleotide sequence or a nucleic acid complementary thereto. Where specified such nucleic acids may include those having a specified degree of homology to a reference sequence, or that are capable of hybridizing to a reference sequence, for example, under stringent conditions [e.g., 50° C. and 0.2×SSC (1×SSC=0.15 M NaCl, 0.015 M $Na_3$ citrate, pH 7.0)] or highly stringent conditions [e.g., 65° C. and 0.1×SSC (1×SSC=0.15 M NaCl, 0.015 M $Na_3$ citrate, pH 7.0)]. A variant nucleic acid may be optimized to reflect preferred codon usage for a specified host organisms, such as the methylotrophic yeasts (e.g., *Pichia, Hansenula*, etc) or filamentous fungi (e.g., *Trichoderma* (e.g., *T. reesei*), etc) or other expression hosts (e.g., *Bacillus, Streptomyces*, and the like).

The term "recombinant," when used in reference to a subject cell, nucleic acid, protein or vector, indicates that the subject has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "recovered," "isolated," and "separated," refer to a compound, protein, cell, nucleic acid or amino acid that is removed from at least one component with which it is naturally associated and found in nature.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

The terms "thermostable" and "thermostability" refers to the ability of the enzyme to retain activity after exposure to an elevated temperature. The thermostability of an enzyme, such as an α-amylase enzymes, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range" refers to the range of pH values under which an enzyme exhibits catalytic activity.

As used herein, the terms "pH stable" and "pH stability" relate to the ability of an enzyme to retain activity over a wide range of pH values for a predetermined period of time (e.g., 15 min., 30 min., 1 hour, and the like).

As used herein, the term "amino acid sequence" is synonymous with the terms "polypeptide," "protein," and "peptide," and are used interchangeably. Where such amino acid sequence exhibit activity, they may be referred to as an "enzyme." The conventional one-letter or three-letter code for amino acid residues are used herein.

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence.

Unless otherwise indicated, nucleic acids are written left to right in 5' to 3' orientation; amino acid sequences are written left to right in amino to carboxy orientation, respectively.

By "homologue" shall mean an entity having a certain degree of identity with the subject amino acid sequences and the subject nucleotide sequences. A homologous sequence is taken to include an amino acid sequence that is at least 75%, 80%, 81%, 82%, 83%, 84%, 85%, 86%, 87%, 88%, 89%, 90%, 91%, 92%, 93%, 94%, 95%, 96%, 97%, 98%, or even 99% identical to the subject sequence, using conventional sequence alignment tools (e.g., Clustal, BLAST, and the like). Typically, homologues will include the same active site residues as the subject amino acid sequence, unless otherwise specified.

As used herein, "hybridization" refers to the process by which one strand of nucleic acid base pairs with a complementary strand, as occurs during blot hybridization techniques and PCR techniques.

As used herein, a "synthetic" molecule is produced by in vitro chemical or enzymatic synthesis rather than by an organism.

As used herein, the terms "transformed," "stably transformed," and "transgenic," used with reference to a cell means that the cell has a non-native (e.g., heterologous) nucleic acid sequence integrated into its genome or carried as an episomal plasmid that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct including a polynucleotide encoding a polypeptide of interest (e.g., a variant α-amylase) has been introduced. Exemplary host strains are bacterial cells. The term "host cell" includes protoplasts created from cells, such as those of a *Bacillus* sp.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on the nucleic acid sequence of a gene. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

"Culturing" refers to growing a population of microbial cells under suitable conditions in a liquid or solid medium. Culturing includes fermentative bioconversion of a starch substrate containing granular starch to an end-product (typically in a vessel or reactor).

"Fermentation" is the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

A "gene" refers to a DNA segment that is involved in producing a polypeptide, and includes coding regions, regions preceding and following the coding regions, and, intervening sequences (introns) between individual coding segments (exons).

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter. An exemplary promoter is the *Bacillus licheniformis* α-amylase (AmyL) promoter.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

The term, "under transcriptional control" means that transcription of a polynucleotide sequence, usually a DNA sequence, depends on its being operably linked to an element which contributes to the initiation of, or promotes transcription.

The term "under translational control" means that translation of a polynucleotide sequence, usually an RNA sequence, into a polypeptides depends on its being operably linked to an element which contributes to the initiation of, or promotes translation.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, "biologically active" refer to a sequence having a specified biological activity, such an enzymatic activity. In the case of the present amylases, the activity is α-amylase activity.

"Water hardness" is a measure of the minerals (e.g., calcium and magnesium) present in water.

"Saccharification" refers to the enzymatic conversion of starch to glucose.

"Gelatinization" refers to solubilization of a starch molecule by cooking to form a viscous suspension.

"Liquefaction" refers to the stage in starch conversion in which gelatinized starch is hydrolyzed to give low molecular weight soluble dextrins.

The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

With respect to starch conversion, the terms "end-product" or "desired end-product" refer to specified carbon-source-derived molecules, which are enzymatically converted from a starch substrate.

As used herein, the term "dry solids content (ds)" refers to the total solids in a slurry, expressed in % dry weight.

The term "slurry" refers to an aqueous mixture containing insoluble solids.

The term "residual starch" refers to the remaining starch (soluble or insoluble) in a composition after fermentation or enzymatic hydrolysis of a starch containing substrate.

As used herein "a recycling step" refers to the recycling of mash components, which may include residual starch, enzymes and/or microorganisms to ferment substrates comprising starch.

The term "mash" refers to an aqueous mixture including a fermentable carbon source (e.g., carbohydrate), which may be used to produce a fermented product, such as an alcohol. The terms "beer" and "mash" may be used interchangeability.

The term "stillage" refers to a mixture of non-fermented solids and water, which represents the residue following removal of alcohol from a fermented mash.

The terms "distillers dried grain (DDG)" and "distillers dried grain with solubles (DDGS)" refer to a useful by-product of grain fermentation.

As used herein "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein the term "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. A preferred yeast includes strains of *Sacchromyces*, particularly, *S. cerevisiae*.

With respect to amylase enzymes and their substrates, the term "contacting" refers to the placing of the enzyme in sufficiently close proximity to the substrate to enable the enzyme to convert the substrate to an end-product. Contacting may include mixing.

The term "derived from" means "originated from," "based on," "obtained from," or "obtainable from," or "isolated from," depending on context.

The term "enzymatic conversion" generally refers to the modification of a substrate (e.g., starch) by enzyme action (e.g., amylase).

As used herein the term "specific activity" refers to the number of moles of substrate converted to product by an enzyme preparation per unit time under specific conditions. Specific activity is expressed as units (U)/mg of protein.

The term "yield" refers to the amount of end-product produced by a process, e.g., expressed in concentration, volume, amount, or a percentage of staring material.

"ATCC" refers to American Type Culture Collection located at Manassas, Va. 20108 (ATCC).

"NRRL" refers to the Agricultural Research Service Culture Collection, National Center for Agricultural Utilization Research (and previously known as USDA Northern Regional Research Laboratory), Peoria, Ill.

Numeric ranges are inclusive of the numbers defining the range.

Generally, headings are descriptive and are not intended as limitations.

1.2 Abbreviations

The following abbreviations apply unless indicated otherwise:

AE alcohol ethoxylate
AEO alcohol ethoxylate
AEOS alcohol ethoxysulfate
AES alcohol ethoxysulfate
AFAU acid fungal α-amylase units
AGU glucoamylase activity unit
AOS α-olefinsulfonate
AS alcohol sulfate
BAA *Bacillus amyloliquefaciens* α-amylase
BLA *Bacillus licheniformis* (or LAT)
BSA bovine serum albumin
cDNA complementary DNA
CMC carboxymethylcellulose
DNA deoxyribonucleic acid
DP3 degree of polymerization with three subunits
DPn degree of polymerization with n subunits
DTMPA diethyltriaminepentaacetic acid
EC enzyme commission for enzyme classification
EDTA ethylenediaminetetraacetic acid
EO ethylene oxide
F&HC fabric and household care
FAU fungal amylase unit
GA glucoamylase
gpg grains per gallon
HFCS high fructose corn syrup
HFSS high fructose starch based syrup
IPTG isopropyl β-D-1-thiogalactopyranoside
LAS linear alkylbenezenesulfonate
LOM Launder-O-meter
LU Liquiphon unit
MW molecular weight
MWU modified Wohlgemuth unit
NOBS nonanoyloxybenzenesulfonate
NTA nitrilotriacetic acid
PCR polymerase chain reaction
PEG polyethyleneglycol
PVA poly(vinyl alcohol)
PVP poly(vinylpyrrolidone)
RNA ribonucleic acid
SAS secondary alkane sulfonates
TAED tetraacetylethylenediamine
TCA trichloroacetic acid
TSB tryptic soy broth
UFC ultrafiltration concentrate
w/v weight/volume
w/w weight/weight
wt wild-type 1.3 Nomenclature In the present description and claims, the conventional one-letter and three-letter codes for amino acid residues are used. For ease of reference, α-amylase variants of the present compositions and methods are described by use of the following nomenclature:

Original amino acid(s): position(s): substituted amino acid(s)

According to this nomenclature, for instance the substitution of serine by an alanine in position 242 is shown as:
Ser242Ala or S242A a deletion of alanine in position 30 is shown as:
Ala30* or A30* or AA30 and insertion of an additional amino acid residue, such as lysine, is shown as:
Ala30AlaLys or A30AK A deletion of a consecutive stretch of amino acid residues, such as amino acid residues 30-33, is indicated as (30-33)* or Δ(A30-N33) or Δ30-33. A deletion of two consecutive amino acids, such as amino acid residues R180-S181, is indicated as ΔRS or Δ180-181.

Where a specific α-amylase contains a "deletion" in comparison with other α-amylases and an insertion is made in such a position this is indicated as:

*36Asp or *36D for insertion of an aspartic acid in position 36.

Multiple mutations are separated by plus signs, i.e.:

Ala30Asp+Glu34Ser or A30N+E34S representing mutations in positions 30 and 34 substituting alanine and glutamic acid for asparagine and serine, respectively.

When one or more alternative amino acid residues may be inserted in a given position it is indicated as A30N,E or A30N or A30E Furthermore, when a position suitable for modification is identified herein without any specific modification being suggested, it is to be understood that any amino acid residue may be substituted for the amino acid residue present in the position. Thus, for instance, when a modification of an alanine in position 30 is mentioned, but not specified, it is to be understood that the alanine may be deleted or substituted for any other amino acid, i.e., any one of:

R, N, D, A, C, Q, E, G, H, I, L, K, M, F, P, S, T, W, Y, V.

Further, "A30X" means any one of the following substitutions:

A30R, A30N, A30D, A30C, A30Q, A30E, A30G, A30H, A30I, A30L, A30K, A30M, A30F, A30P, A30S, A30T, A30W, A30Y, or A30 V;

or in short: A30R,N,D,C,Q,E,G,H,I,L,K,M,F,P,S,T,W,Y,V.

If the parent enzyme—used for the numbering—already has the amino acid residue in question suggested for substitution in that position the following nomenclature is used:

"X30N" or "X30N,V"

in the case where for instance one of N or V is present in the wildtype. Thus, it means that other corresponding parent enzymes are substituted to an "Asn" or "Val" in position 30.

1.4 Characteristics of Amino Acid Residues

Charged amino acids:

Asp, Glu, Arg, Lys, His

Negatively charged amino acids (with the most negative residue first):

Asp, Glu

Positively charged amino acids (with the most positive residue first):

Arg, Lys, His

Neutral amino acids:

Gly, Ala, Val, Leu, lie, Phe, Tyr, Trp, Met, Cys, Asn, Gln, Ser, Thr, Pro

Hydrophobic amino acid residues (with the most hydrophobic residue listed last):

Gly, Ala, Val, Pro, Met, Leu, lie, Tyr, Phe, Trp,

Hydrophilic amino acids (with the most hydrophilic residue listed last):

Thr, Ser, Cys, Gln, Asn 1.5 Homology (Identity)

A polynucleotide or a polypeptide having a certain percent (e.g., 80%, 81%, 82%, 83%, 84%, 85%, 86%, 87%, 88%, 89%, 90%, 91%, 92%, 93%, 94%, 95%, 96%, 97%, 98%, or even 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY (F. M. Ausubel et al. (eds) 1987, Supplement 30, section 7.7.18). Preferred programs include the Vector NTI Advance™ 9.0 (Invitrogen Corp. Carlsbad, Calif.), GCG Pileup program, FASTA (Pearson et al. (1988) *Proc. Natl. Acad. Sci. USA* 85:2444-2448), and BLAST (BLAST Manual, Altschul et al., Natl Cent. Biotechnol. Inf., Natl Lib. Med. (NCIB NLM NIH), Bethesda, Md., and Altschul et al., (1997) *NAR* 25:3389-3402). Another preferred alignment program is ALIGN Plus (Scientific and Educational Software, PA), preferably using default parameters. Another sequence software program that finds use is the TFASTA Data Searching Program available in the Sequence Software Package Version 6.0 (Genetics Computer Group, University of Wisconsin, Madison, Wis.).

The homology may be determined as the degree of identity between the two sequences indicating a derivation of the first sequence from the second. The homology may suitably be determined by means of computer programs known in the art such as GAP provided in the GCG program package (described above). Thus, GAP GCG v8 may be used with the default scoring matrix for identity and the following default parameters: gap creation penalty of 5.0 and gap extension penalty of 0.3, respectively for nucleic acidic sequence comparison, and gap creation penalty of 3.0 and gap extension penalty of 0.1, respectively, for protein sequence comparison. GAP uses the method of Needleman and Wunsch, (1970), J. Mol. Biol. 48:443-453, to make alignments and to calculate the identity.

A structural alignment between AmyTS23 (SEQ ID NO: 1) and, e.g., another α-amylase may be used to identify equivalent/corresponding positions in other α-amylases having a high degree of homology, e.g., about 80%, 81%, 82%, 83%, 84%, 85%, 86%, 87%, 88%, 89%, 90%, 91%, 92%, 93%, 94%, 95%, 96%, 97%, 98%, or even 99%, with AmyTS23. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber, T; Torda, A E, PROTEIN SCIENCE Vol. 7, No. 1 pp. 142-149 (1998).

1.6 Hybridisation

The oligonucleotide probe used in the characterization of AmyTS23, above, may suitably be prepared on the basis of the full or partial nucleotide or amino acid sequence of the α-amylase in question.

Suitable conditions for testing hybridization involve presoaking in 5×SSC and prehybridizing for 1 hour at 40° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at 40° C., followed by three times washing of the filter in 2×SSC, 0.2% SDS at 40° C. for 30 minutes (low stringency), preferred at 50° C. (medium stringency), more preferably at 65° C. (high stringency), even more preferably at 75° C. (very high stringency). More details about the hybridization method can be found in Sambrook et al., Molecular Cloning: A Laboratory Manual, 2nd Ed., Cold Spring Harbor, 1989.

In the present context, "derived from" is intended not only to indicate an α-amylase produced or producible by a strain of the organism in question, but also an α-amylase encoded by a DNA sequence isolated from such strain and produced in a host organism transformed with said DNA sequence. Finally, the term is intended to indicate an α-amylase, which is encoded by a DNA sequence of synthetic and/or cDNA origin and which has the identifying characteristics of the α-amylase in question. The term is also intended to indicate that the parent α-amylase may be a variant of a naturally occurring α-amylase, i.e., a variant, which is the result of a modification (insertion, substitution, deletion) of one or more amino acid residues of the naturally occurring α-amylase.

One skilled in the art will recognize that sequences encompassed by the present compositions and methods are also defined by the ability to hybridize under stringent hybridization conditions with the exemplified amyTS23 sequence (e.g., SEQ ID NO:4 shown in FIG. 4). A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art (See, e.g., Sambrook (1989) supra, particularly chapters 9 and 11). In some embodiments, stringent conditions correspond to a Tm of 65° C. and 0.1× SSC, 0.1% SDS.

1.7 Parent α-amylases

According to the present disclosure any AmyTS23 α-amylase, as defined above, may be used as the parent (i.e., backbone) α-amylase. In a preferred embodiment the parent α-amylase is derived from *Bacillus* sp. strain TS-23, e.g., one of those referred to above, such as the TS-23 α-amylase having the amino acid sequence shown in SEQ ID NO: 1 (FIG. 1).

1.8 Altered Properties

The following section describes the relationship between mutations, which are present in the variant amylases described herein, and desirable alterations in properties (relative to those of a parent TS-23 α-amylase), which may result therefrom. The variants encompassed by the present compositions and methods are described in detail throughout the specification, and merely summarized in the following paragraphs.

As described, above, as aspect of the compositions and methods relate to α-amylases derived or derivable from *Bacillus* sp strain TS-23 α-amylase, including variants/mutants having altered properties with respect to parent amylases. Parent amylases are the above-mentioned parent TS-23 α-amylase and hybrid or chimeric amylases that include at least a portion of a TS-23 α-amylase, such as amino acid sequences of the mature polypeptide.

While the *Bacillus* sp strain TS-23 α-amylase (SEQ ID NO: 1) is used as a starting point for discussing variant amylases, it will be appreciated that other *Bacillus* α-amylases having a high degree of homology to the *Bacillus* sp strain TS-23 α-amylase may serve as a parental amylase without defeating the scope of the compositions and methods. This is particularly true of other naturally-occurring *Bacillus* α-amylases that include only minor sequence different in comparison to *Bacillus* sp strain TS-23 α-amylase, not including the substitutions, deletions, or insertions, that are the subject of the present disclosure.

In the first aspect of the presence compositions and methods, a variant of a parent *Bacillus* sp. strain α-amylase is provided, wherein the variant comprises at least two of the following alterations:

(a) truncation of the C-terminus,
(b) substitution of amino acid 201 (i.e., M201), using SEQ ID NO:1 for numbering, or
(c) deletion of at least two residues selected from the group consisting of R180, S181, T182 and G183. Note that the numbering of the amino acid residues refers to SEQ ID NO:1. In some embodiments, the alterations include (a) and (b). In other embodiments, the alterations include (a) and (c). In some embodiments, the variant may further include a substitution at one or more residues selected from the group consisting of residue 87, residue 225, residue 272, and residue 282 The variant amylase preferably has α-amylase activity. Excluding the particular alterations specified, other remaining amino acid sequences of the variant amylase may have at least 85% amino acid sequence identity to the amino acid sequence of SEQ ID NO: 1.

In a related aspect, a variant of a parent AmyTS23 α-amylase is provided, wherein the variant has an amino acid sequence which has at least 85% identity to the parent α-amylase and comprises a truncation of the C-terminus. The variant may the amino acid sequence of SEQ ID NO: 2. The variant may have increased cleaning activity against starch stains in cold water compared to the parent amylase.

In some embodiments, the variant comprising a truncation of the C-terminus may further include a deletion of the residues at position R180 and S181 (referring to the amino acid sequence of SEQ ID NO:1). The resulting variant may have increased detergent stability compared to the parent amylase.

In some embodiments, the variant comprising a truncation of the C-terminus may further include a substitution of the residue at position 201 (again, referring to the amino acid sequence of SEQ ID NO:1). The resulting variant may have increased oxidative stability compared to the parent amylase.

In some embodiments, any of the aforementioned variants may further include a substitution at one or more residues selected from the group consisting of residue 87, residue 225, residue 272, and residue 282.

1.8.1 Stability

In the context of the variants described herein, mutations (including amino acid substitutions and deletion) of importance with respect to achieving altered stability (i.e., higher or lower), in particular improved stability, at especially high temperatures (i.e., 70-120° C.) and/or extreme pH (i.e., low or high pH, i.e., pH 4-6 or pH 8-11, respectively), in particular at free (i.e., unbound, therefore in solution) calcium concentrations below 60 ppm, include any of the mutations listed in the "Altered Properties" section. The stability may be determined as described in the "Methods" section below.

1.8.2 $Ca^{2+}$ Stability

Altered $Ca^{2+}$ stability means the stability of the enzyme under $Ca^{2+}$ depletion has been improved, i.e., higher or lower stability. In the context of the presently described variants, mutations (including amino acid substitutions and deletions) of importance with respect to achieving altered $Ca^{2+}$ stability, in particular improved $Ca^{2+}$ stability, i.e., higher or lower stability, at especially high pH (i.e., pH 8-10.5) include any of the mutations listed in the in "Altered Properties" section.

1.8.3 Specific Activity

In a further aspect, important mutations (including amino acid substitutions and deletions) with respect to obtaining variants exhibiting altered specific activity, in particular increased or decreased specific activity, especially at temperatures from 10-60° C., preferably 20-50° C., especially 30-40° C., include any of the mutations listed in the in "Altered properties" section. The specific activity may be determined as described in the "Methods" section below.

1.8.4 Oxidation Stability

The described variants may have altered oxidation stability, in particular higher oxidation stability, in comparison to the parent α-amylase. Increased oxidation stability is advantageous in, e.g., detergent compositions and decreased oxidation stability may be advantageous in composition for starch liquefaction. Oxidation stability may be determined as described in the "Methods" section below.

1.8.5 Altered pH Profile

Important positions and mutations with respect to obtaining variants with altered pH profile, in particular improved activity at especially high pH (i.e., pH 8-10.5) or low pH (i.e., pH 4-6) include mutations of amino residues located close to the active site residues.

Preferred specific mutations/substitutions are the ones listed above in the section "Altered Properties" for the positions in question. Suitable assays are described in the "Methods" section below.

1.8.6 Wash Performance

Important positions and mutations with respect to obtaining variants with improved wash performance at especially high pH (i.e., pH 8.5-11) include the specific mutations/substitutions listed above in the section "Altered Properties" for the positions in question. The wash performance may be tested as described below in the "Methods" section.

2. Methods for Preparing α-amylase Variants

Thus, one aspect provides for *Bacillus* sp. strain TS-23 α-amylase sequence in creating recombinant forms that include other previously determined amino acid substitutions, deletions, transversions, insertions, and combinations thereof to produce variants of the *Bacillus* sp. strain TS-23 α-amylase. These variants can have additional production enhancement, increased pH stability, increased temperature stability, reduced requirements for $Ca^{2+}$, increased specific activity, increased dishwashing or washing performance, increased solubility, increased storage stability, or combinations thereof. Methods of recombinantly generating the variants could be performed using the provided sequences and vectors, or using other modalities known in the art.

Several methods for introducing mutations into genes are known in the art. After a brief discussion of the cloning of α-amylase-encoding DNA sequences, methods for generating mutations at specific sites within the α-amylase-encoding sequence will be discussed.

2.1 Cloning a DNA Sequence Encoding an α-amylase

DNA sequences encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labeled oligonucleotide probes may be synthesized and used to identify α-amylase-encoding clones from a genomic library prepared from the organism in question. Alternatively, a labeled oligonucleotide probe containing sequences homologous to a known α-amylase gene could be used as a probe to identify α-amylase-encoding clones, using hybridization and washing conditions of lower stringency.

Yet another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoamidite method described by S. L. Beaucage and M. H. Caruthers (1981) or the method described by Matthes et al. (1984). In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

2.2 Site-directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into α-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Alternative methods for providing variants include gene shuffling, e.g., as described in WO 95/22625 (from Affymax Technologies N.V.) or in WO 96/00343 (from Novo Nordisk A/S), or other corresponding techniques resulting in a hybrid enzyme comprising the mutation(s), e.g., substitution(s) and/or deletion(s), in question.

2.3 Expression of α-amylase Variants

A DNA sequence encoding an α-amylase variant produced by methods described above, or by any alternative methods known in the art, can be use to express a variant amylase (i.e., an enzyme), using an expression vector, which typically includes control sequences encoding a promoter, operator, ribosome binding site, translation initiation signal, and, optionally, a repressor gene or various activator genes.

A recombinant expression vector carrying DNA sequences encoding an α-amylase variant may be any vector, which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the DNA sequence encoding an α-amylase variant of the present compositions and methods, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Geobacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector may also comprise a suitable transcription terminator and, in eukaryotes, polyadenylation sequences operably connected to the DNA sequence encoding the α-amylase variant of the present compositions and methods. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g., as described in WO 91/17243.

While intracellular expression may be advantageous in some respects, e.g., when using certain bacteria as host cells, it is generally preferred that the expression is extracellular. In general, the *Bacillus* α-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct encoding an α-amylase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

The cell, either comprising a DNA construct or an expression vector, is advantageously used as a host cell in the recombinant production of an α-amylase variant. The cell may be transformed with the DNA construct of the present compositions and methods encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells. The cell may be a cell of a higher organism such as a mammal or an insect, but is preferably a microbial cell, e.g., a bacterial or a fungal (including yeast) cell.

Examples of suitable bacteria are Gram-positive bacteria such as *Bacillus subtilis, Bacillus licheniformis, Bacillus lentus, Bacillus brevis, Geobacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram-negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

In a yet further aspect, a method of producing an α-amylase variant is provided, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the α-amylase variant. Suitable media are available from commercial suppliers or may be prepared according to published recipes (e.g., as described in catalogues of the American Type Culture Collection).

The α-amylase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

3. Industrial Applications

The α-amylase variants presented herein possess valuable properties allowing for a variety of industrial applications. In particular, the enzyme variants are applicable as a component in washing, dishwashing, and hard surface cleaning detergent compositions.

One or more of the variants with altered properties may be used for starch processes, in particular starch conversion, especially liquefaction of starch (see, e.g., U.S. Pat. No. 3,912,590, EP patent application nos. 252 730 and 63 909, WO 99/19467, and WO 96/28567 all references hereby incorporated by reference). Also contemplated are compositions for starch conversion purposes, which may beside the variant of the present compositions and methods also comprise a glucoamylase, pullulanase, and other α-amylases.

Further, one or more of the variants are also particularly useful in the production of sweeteners and ethanol (see, e.g., U.S. Pat. No. 5,231,017, hereby incorporated by reference), such as fuel, drinking and industrial ethanol, from starch or whole grains.

The variants herein may also be useful for desizing of textiles, fabrics and garments (see, e.g., WO 95/21247, U.S. Pat. No. 4,643,736, EP 119,920, hereby incorporated by reference), beer making or brewing, in pulp and paper production.

3.1 Starch Conversion

Conventional starch-conversion processes, such as liquefaction and saccharification processes are described, e.g., in U.S. Pat. No. 3,912,590 and EP patent publications Nos. 252,730 and 63,909, hereby incorporated by reference.

In an embodiment the starch conversion process degrading starch to lower molecular weight carbohydrate components such as sugars or fat replacers includes a debranching step.

3.2 Starch to Sugar Conversion

In the case of converting starch into a sugar the starch is depolymerized. Such a depolymerization process may consists of a pre-treatment step and two or three consecutive process steps, such as a liquefaction process, a saccharification process and (depending on the desired end product), an optional isomerization process.

3.3 Pre-Treatment of Native Starch

Native starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation.

3.4 Liquefaction

During the liquefaction step, the long chained starch is degraded into branched and linear shorter units (maltodextrins) by an α-amylase. The liquefaction process is typically carried out at 105-110° C. for 5 to 10 minutes followed by 1-2 hours at 95° C. at a between 5.5 and 6.2. In order to ensure optimal enzyme stability under these conditions, 1 mM of calcium is added (40 ppm free calcium ions). After this treatment the liquefied starch will have a "dextrose equivalent" (DE) of 10-15.

3.5 Saccharification

After the liquefaction process the maltodextrins are converted into dextrose by addition of a glucoamylase (e.g., OPTIDEX® L-400) and a debranching enzyme, such as an isoamylase (U.S. Pat. No. 4,335,208) or a pullulanase. Before this step the pH is reduced to a value below 4.5, while maintaining the high temperature (above 95° C.) to inactivate the liquefying α-amylase, thereby reducing the formation of short oligosaccharides called "panose precursors," which cannot be hydrolyzed properly by the debranching enzyme.

The temperature is lowered to 60° C., and glucoamylase and debranching enzyme are added. The saccharification process proceeds for 24-72 hours.

Normally, when denaturing the α-amylase after the liquefaction step about 0.2-0.5% of the saccharification product is the branched trisaccharide Glc pα1-6Glc pα1-4Glc (panose), which cannot be degraded by a pullulanase. If active amylase from the liquefaction step is present during saccharification (i.e., no denaturing), this level can be as high as 1-2%, which is highly undesirable as it lowers the saccharification yield significantly.

3.6 Isomerization

When the desired final sugar product is, e.g., high fructose syrup the dextrose syrup may be converted into fructose. After the saccharification process the pH is increased to a value in the range of 6-8, preferably pH 7.5, and the calcium is removed by ion exchange. The dextrose syrup is then converted into high fructose syrup using, e.g., an immobilized glucose isomerase (such as GENSWEET® IGI-HF).

3.7 Ethanol Production

In general alcohol production (ethanol) from whole grain can be separated into 4 main steps:

Milling
Liquefaction
Saccharification
Fermentation

3.7.1 Milling

The grain is milled in order to open up the structure and allow for further processing. Two processes used are wet or dry milling. In dry milling the whole kernel is milled and used in the remaining part of the process. Wet milling gives a very good separation of germ and meal (starch granules and protein) and is with a few exceptions applied at locations where there is a parallel production of syrups.

3.7.2 Liquefaction

In the liquefaction process the starch granules are solubilized by hydrolysis to maltodextrins mostly of a DP higher than 4. The hydrolysis may be carried out by acid treatment or enzymatically by α-amylase. Acid hydrolysis is used on a limited basis. The raw material can be milled whole grain or a side stream from starch processing.

Enzymatic liquefaction is typically carried out as a three-step hot slurry process. The slurry is heated to between 60-95° C., preferably 80-85° C., and the enzyme(s) is (are) added. Then the slurry is jet-cooked at between 95-140° C., preferably 105-125° C., cooled to 60-95° C. and more enzyme(s) is (are) added to obtain the final hydrolysis. The liquefaction process is carried out at pH 4.5-6.5, typically at a pH between 5 and 6. Milled and liquefied grain is also known as mash.

3.7.3 Saccharification

To produce low molecular sugars $DP_{1-3}$ that can be metabolized by yeast, the maltodextrin from the liquefaction must be further hydrolyzed. The hydrolysis is typically done enzymatically by glucoamylases, alternatively α-glucosidases or acid α-amylases can be used. A full saccharification step may last up to 72 hours, however, it is common only to do a pre-saccharification of typically 40-90 minutes and then complete saccharification during fermentation (SSF). Saccharification is typically carried out at temperatures from 30-65° C., typically around 60° C., and at pH 4.5.

3.7.4 Fermentation

Yeast typically from *Saccharomyces* spp. is added to the mash and the fermentation is ongoing for 24-96 hours, such as typically 35-60 hours. The temperature is between 26-34° C., typically at about 32° C., and the pH is from pH 3-6, preferably around pH 4-5.

Note that the most widely used process is a simultaneous saccharification and fermentation (SSF) process where there is no holding stage for the saccharification, meaning that yeast and enzyme is added together. When doing SSF it is common to introduce a pre-saccharification step at a temperature above 50° C., just prior to the fermentation.

3.8 Distillation

Following the fermentation the mash is distilled to extract the ethanol. The ethanol obtained according to the process, may be used as, e.g., fuel ethanol; drinking ethanol, i.e., potable neutral spirits; or industrial ethanol.

3.9 By-Products

Left over from the fermentation is the grain, which is typically used for animal feed either in liquid form or dried.

Further details on how to carry out liquefaction, saccharification, fermentation, distillation, and recovery of ethanol are well known to the skilled person.

According to the process, the saccharification and fermentation may be carried out simultaneously or separately.

3.10 Pulp and Paper Production

The present α-amylases may also be used in the production of lignocellulosic materials, such as pulp, paper and cardboard, from starch reinforced waste paper and cardboard, especially where repulping occurs at pH above 7 and where amylases facilitate the disintegration of the waste material through degradation of the reinforcing starch. The α-amylases are especially useful in a process for producing a papermaking pulp from starch-coated printed-paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

The α-amylases may also be very useful in modifying starch where enzymatically modified starch is used in papermaking together with alkaline fillers such as calcium carbonate, kaolin and clays. With the α-amylases of the present compositions and methods it becomes possible to modify the starch in the presence of the filler thus allowing for a simpler integrated process.

3.11 Desizing of Textiles, Fabrics and Garments

The present α-amylases may also be very useful in textile, fabric or garment desizing. In the textile processing industry, α-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch breakdown is preferred because it does not involve any harmful effect on the fiber material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional α-amylases are not very compatible with high pH levels and bleaching agents. The non-enzymatic breakdown of the starch size does lead to some fiber damage because of the rather aggressive chemicals used. Accordingly, it would be desirable to use the α-amylases of the present compositions and methods as they have an improved performance in alkaline solutions. The α-amylases may be used alone or in combination with a cellulase when desizing cellulose-containing fabric or textile.

Desizing and bleaching processes are well known in the art. For instance, such processes are described in WO 95/21247, U.S. Pat. No. 4,643,736, EP 119,920 hereby incorporated by reference.

Commercially available products for desizing include OPTISIZE® FLEX from Genencor.

Also contemplated are compositions and methods of treating fabrics (e.g., to desize a textile) using one or more *Bacillus* sp. strain TS-23 α-amylases or variants thereof. The enzyme can be used in any fabric-treating method known in the art, see, e.g., U.S. Pat. No. 6,077,316. For example, in one aspect, the feel and appearance of a fabric is improved by a method comprising contacting the fabric with a *Bacillus* sp. strain TS-23 α-amylase or variant thereof in a solution. In one aspect, the fabric is treated with the solution under pressure.

In one aspect, the enzymes are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. Also provided is a method of desizing comprising enzymatic hydrolysis of the size by the action of a *Bacillus* sp. strain TS-23 α-amylase or variant thereof.

The enzymes can be used alone or with other desizing chemical reagents and/or desizing enzymes to desize fabrics, including cotton-containing fabrics, as detergent additives, e.g., in aqueous compositions. A *Bacillus* sp. strain TS-23 α-amylase or variant thereof can also be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The enzymes can be used in methods of finishing denim garments (e.g., a "bio-stoning process"), enzymatic desizing and providing softness to fabrics, and/or finishing process. Dosage of the amylase varies depending on the process type. Smaller dosages would require more time than larger dosages of the same enzyme. However, there is no upper limit on the amount of a desizing amylase present other than that dictated by the physical constraints of the solution. Thus, the limit of the enzyme may be the amount capable of solubilization in the solution. Typically, desizing enzymes, such as α-amylases, are incorporated in to the treating composition in an amount from about 0.00001% to about 2% of enzyme protein by weight of the fabric; or from about 0.0001% to about 1% of enzyme protein by weight of the fabric; or from about 0.001% to about 0.5% of enzyme protein by weight of the fabric; and in another example would be from about 0.01% to about 0.2% of enzyme protein by weight of the fabric.

3.12 Beer Making

The variant α-amylases provided for herein may also be very useful in a beer-making process; the α-amylases will typically be added during the mashing process.

3.13 Detergent Compositions

The variant α-amylases described herein may be added to and thus become a component of a detergent composition.

The detergent composition provided for herein may for example be formulated as a hand or machine laundry detergent composition including a laundry additive composition suitable for pretreatment of stained fabrics and a rinse added fabric softener composition or be formulated as a detergent composition for use in general household hard surface cleaning operations, or be formulated for hand or machine dishwashing operations.

In a specific aspect, there is provided for herein a detergent additive comprising a variant enzyme described herein. The detergent additive as well as the detergent composition may comprise one or more other enzymes such as a protease, a lipase, a peroxidase, another amylolytic enzyme, e.g., another α-amylase, glucoamylase, maltogenic amylase, CGTase and/or a cellulose, mannanase (such as MANNASTAR™ from Danisco U.S.A., Inc., Genencor Division), pectinase, pectin lyase, cutinase, and/or laccase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease or a chymotrypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases also include but are not limited to the variants described in WO98/23732, WO99/20770, WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Exemplary commercially available protease enzymes include ALCALASE®, SAVINASE®, PRIMASE®, DURALASE®, ESPERASE®, and KANNASE® (from Novozymes A/S), MAXATASE®, MAXACAL, MAXAPEM®, PROPERASE®, PURAFECT®, PURAFECT OXP®, FN2®, FN3® and FN4® (Genencor).

Lipases: Suitable lipases include those of bacterial or fungal origin. Chemically modified or protein engineered mutants are included. Examples of useful lipases include but are not limited to lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al. (1993), Biochemica et Biophysica Acta, 1131, 253-360), *B. stearothermophilus* (JP 64/744992) or *B. pumilus* (WO 91/16422). Additional exemplary lipase variants contemplated for use in the formulations include those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Commercially available lipase enzymes include LIPOLASE™ and LIPOLASE ULTRA™ (Novozymes A/S).

Polyesterases: suitable polyesterases can be included in composition. Suitable polyesterases include for example those described in WO 01/34899 and WO 01/14629.

Amylases: One or more additional amylases (in addition to the variant amylase(s) described herein) may also be included. Suitable amylases (α and/or β) include those of bacterial or fungal origin. Chemically modified or protein engineered mutants are included. Amylases include, for example, α-amylases obtained from *Bacillus*, e.g., a special strain of *B. licheniformis*, described in more detail in GB 1,296,839. Examples of useful α-amylases are the variants described in WO 94/18314, WO 96/39528, WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available α-amylases are DURAMYL™, LIQUEZYME™ TERMAMYL™, NATALASE™, STAINZYME™ PLUS, STAINZYME™ ULTRA, FUNGAMYL™ and BAN™ (Novozymes A/S), RAPIDASE™ and PURASTAR™ (from Genencor).

Cellulases: Cellulases may be added to the compositions. Suitable cellulases include those of bacterial or fungal origin. Chemically modified or protein engineered mutants are included. Suitable cellulases include but are not limited to cellulases from the genera *Bacillus, Pseudomonas, Trichoderma, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Exemplary *Trichoderma reesei* cellulases are disclosed in U.S. Pat. Nos. 4,689,297, 5,814, 501, 5,324,649, WO 92/06221 and WO 92/06165. Exemplary *Bacillus* cellulases are disclosed in U.S. Pat. No. 6,562,612.

Commercially available cellulases include CELLUZYME®, and CAREZYME® (Novozymes A/S), CLAZINASE®, and PURADAX HA® (Genencor International Inc.), and KAC-500(B)® (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME® (Novozymes A/S).

The detergent enzyme(s) may be included in a detergent composition by adding separate additives containing one or more enzymes, or by adding a combined additive comprising all of these enzymes. A detergent additive of the present compositions and methods, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Generally, the detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels contained for example about 30% water or less.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system that may comprise a $H_2O_2$ source, such as perborate or percarbonate, which may be combined with a peracid-forming bleach activator (e.g., tetraacetylethylenediamine or nonanoyloxybenzenesulfonate). Alternatively, the bleaching system may comprise peroxyacids (e.g. the amide, imide, or sulfone type peroxyacids). The bleaching system can also be an enzymatic bleaching system. See for example WO 05/056782.

The enzyme(s) of the detergent composition of the present compositions and methods may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil re-deposition agents, dyes, bactericides, optical brighteners, hydrotropes, tarnish inhibitors, or perfumes.

It is at present contemplated that in the detergent compositions, in particular a *Bacillus* sp. strain TS-23 α-amylase or variant thereof, may be added in an amount corresponding to about 0.01 to about 100 mg of enzyme protein per liter of wash liquor, for example about 0.05 to about 5.0 mg of enzyme protein per liter of wash liquor, or about 0.1 to about 1.0 mg of enzyme protein per liter of wash liquor.

One or more of the variant enzymes described herein may additionally be incorporated in the detergent formulations disclosed in WO 97/07202, which is hereby incorporated as reference.

4. Compositions and Use

One or more of the variant enzymes described herein may also be used in methods for using an α-amylase variant in detergents, in particular laundry detergent compositions and dishwashing detergent compositions, hard surface cleaning compositions, and in composition for desizing of textiles, fabrics or garments, for production of pulp and paper, beer making, ethanol production, and starch conversion processes as described above.

4.1 Laundry Detergent Compositions and Use

According to the embodiment, one or more *Bacillus* sp. strain TS-23 α-amylases or variants thereof, may typically be a component of a laundry detergent composition. As such, it may be included in the detergent composition in the form of a non-dusting granulate, a stabilized liquid, or a protected enzyme. The dry formulations may be in the form of a granulate or microgranulate. Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in for example EP Appln. No. 238,216. Polyols have long been recognized as stabilizers of proteins as well as improving solubility of proteins. See, e.g., J. K. Kaushik et al., "Why is trehalose an exceptional protein stabilizer? An analysis of the thermal stability of proteins in the presence of the compatible osmolyte trehalose," *J. Biol. Chem.* 278: 26458-65 (2003) and the references cited therein; and Monica Conti et al., "Capillary isoelectric focusing: the problem of protein solubility," *J. Chromatography* 757: 237-245 (1997).

The composition may comprise a *Bacillus* sp. strain TS-23 α-amylase or variants thereof as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase, as well as other enzymes discussed below. The additional enzyme(s) may be producible by means of a microorganism belonging to the genera *Aspergillus*, *Trichoderma*, *Humicola* (e.g., *H. insolens*), and *Fusarium*. Exemplary members of the *Aspergillus* genus include *Aspergillus aculeatus*, *Aspergillus awamori*, *Aspergillus niger*, or *Aspergillus oryzae*. Exemplary members of the genus *Fusarium* include *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundinis*, *Fusarium oxysporum*, *Fusarium reticulatum*, *Fusarium roseum*, *Fusarium sambucinum*, *Fusarium sarcochroum*, *Fusarium sulphureum*, *Fusarium torulosum*, *Fusarium trichothecioides*, and *Fusarium venenatum*.

The detergent composition may be in any useful form, e.g., powders, granules, pastes, or liquids. A liquid detergent may be aqueous, typically containing up to about 70% of water, and 0% to about 30% of organic solvent. It can also be a in the form of a compact gel type containing only about 30% water. Enzymes may be used in any detergent composition compatible with the stability of the enzyme. Enzymes can be protected against generally deleterious components by known forms of encapsulation as for example by granulation or sequestration in hydro gels. Enzymes and specifically α-amylases are not limited to laundry and dishwashing applications, but can also be used in surface cleaners, ethanol production from starch or biomass.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as lipase, cutinase, protease, cellulase, peroxidase, and/or laccase in any combination. See supra.

The detergent may optionally contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may optionally comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may optionally contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxy acids of e.g. the amide, imide, or sulfone type. The bleaching system can also be an enzymatic bleaching system, where a perhydrolase activates peroxide, as described in for example WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) is usually neutral or alkaline, e.g., pH about 7.0 to about 11.0.

Particular forms of detergent compositions comprising a *Bacillus* sp. strain TS-23 α-amylase or variant thereof, can be formulated to include:

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," Nature 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

A *Bacillus* sp. strain TS-23 α-amylase. or variant thereof, may be incorporated in concentrations conventionally employed in detergents. It is at present contemplated that, in the detergent composition, a *Bacillus* sp. strain TS-23 α-amylase or variant thereof, may be added in an amount corresponding to 0.00001-1.0 mg (calculated as pure enzyme protein) of enzyme per liter of wash liquor.

In another embodiment, a 2,6-β-D-fructan hydrolase can be incorporated in detergent compositions and used for removal/cleaning of biofilm present on household and/or industrial textile/laundry.

The detergent composition may for example be formulated as a hand or machine laundry detergent composition, including a laundry additive composition suitable for pre-treatment of stained fabrics and a rinse added fabric softener composition, or be formulated as a detergent composition for use in general household hard surface cleaning operations, or be formulated for manual or machine laundry operations.

In a specific aspect, the detergent composition can further comprise 2,6-β-D-fructan hydrolase, one or more α-amylases in addition to the *Bacillus* sp. strain TS-23 α-amylase or variant thereof, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof.

In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

4.2 Dishwash Detergent Compositions

The present α-amylases may also be used in dishwash detergent compositions, including the following:

| 1) POWDER AUTOMATIC DISHWASHING COMPOSITION | |
| --- | --- |
| Nonionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetraacetyl ethylene diamine (TAED) | 1-4% |
| Sodium sulphate | 5-33% |
| Enzymes | 0.0001-0.1% |

| 2) POWDER AUTOMATIC DISHWASHING COMPOSITION | |
| --- | --- |
| Nonionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dihydrate | 9-30% |
| Nitrilotrisodium acetate (NTA) | 0-20% |
| Sodium perborate monohydrate | 5-10% |
| Tetraacetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10% |

| 3) POWDER AUTOMATIC DISHWASHING COMPOSITION | |
| --- | --- |
| Nonionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetraacetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

| 4) POWDER AUTOMATIC DISHWASHING COMPOSITION | |
| --- | --- |
| Nonionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetraacetyl ethylene diamine (TAED) Polymer | 0-3% |
| | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

| 5) POWDER AUTOMATIC DISHWASHING COMPOSITION | |
| --- | --- |
| Nonionic surfactant | 1-7% |
| Sodium disilicate | 18-30% |
| Trisodium citrate | 10-24% |
| Sodium carbonate | 12-20% |
| Monopersulphate (2 KHSO$_5$•KHSO$_4$•K$_2$SO$_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

| 6) POWDER AND LIQUID DISHWASHING COMPOSITION WITH CLEANING SURFACTANT SYSTEM | |
| --- | --- |
| Nonionic surfactant | 0-1.5% |
| Octadecyl dimethylamine N-oxide dihydrate | 0-5% |
| 80:20 wt. C18/C16 blend of octadecyl dimethylamine N-oxide dihydrate and hexadecyldimethyl amine N-oxide dihydrate | 0-4% |
| 70:30 wt. C18/C16 blend of octadecyl bis (hydroxyethyl)amine N-oxide anhydrous and hexadecyl bis (hydroxyethyl)amine N-oxide anhydrous | 0-5% |
| C$_{13}$-C$_{15}$ alkyl ethoxysulfate with an average degree of ethoxylation of 3 | 0-10% |
| C$_{12}$-C$_{15}$ alkyl ethoxysulfate with an average degree of ethoxylation of 3 | 0-5% |
| C$_{13}$-C$_{15}$ ethoxylated alcohol with an average degree of ethoxylation of 12 | 0-5% |

| | |
|---|---|
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Citric acid | 0-29% |
| Sodium carbonate | 0-20% |
| Sodium perborate monohydrate | 0-11.5% |
| Tetraacetyl ethylene diamine (TAED) | 0-4% |
| Maleic acid/acrylic acid copolymer | 0-7.5% |
| Sodium sulphate | 0-12.5% |
| Enzymes | 0.0001-0.1% |
| 7) NON-AQUEOUS LIQUID AUTOMATIC DISHWASHING COMPOSITION | |
| Liquid nonionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycolethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |
| 8) NON-AQUEOUS LIQUID DISHWASHING COMPOSITION | |
| Liquid nonionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |
| 9) THIXOTROPIC LIQUID AUTOMATIC DISHWASHING COMPOSITION | |
| $C_{12}$-$C_{14}$ fatty acid | 0-0.5% |
| Block co-polymer surfactant | 1.5-15.0% |
| Sodium citrate | 0-12% |
| Sodium tripolyphosphate | 0-15% |
| Sodium carbonate | 0-8% |
| Aluminium tristearate | 0-0.1% |
| Sodium cumene sulphonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulphonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |
| 10) LIQUID AUTOMATIC DISHWASHING COMPOSITION | |
| Alcohol ethoxylate | 0-20% |
| Fatty acid ester sulphonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dihydrate | 18-33% |
| Sodium stearate | 0-2.5% |
| Sodium perborate monohydrate | 0-13% |
| Tetraacetyl ethylene diamine (TAED) | 0-8% |
| Maleic acid/acrylic acid copolymer | 4-8% |
| Enzymes | 0.0001-0.1% |

| | |
|---|---|
| 11) LIQUID AUTOMATIC DISHWASHING COMPOSITION CONTAINING PROTECTED BLEACH PARTICLES | |
| Sodium silicate | 5-10% |
| Tetrapotassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

11) Automatic dishwashing compositions as described in 1), 2), 3), 4), 6) and 10), wherein perborate is replaced by percarbonate.
12) Automatic dishwashing compositions as described in 1)-6) which additionally contain a manganese catalyst. The manganese catalyst may, e.g., be one of the compounds described in "Efficient manganese catalysts for low-temperature bleaching", Nature 369, 1994, pp. 637-639.

4.3. Biofilm Removal Compositions and Use

The composition may comprise a *Bacillus* sp. strain TS-23 α-amylase or variant thereof, as the major enzymatic component, e.g., a mono-component composition for use in removing biofilms. Alternatively, the composition may comprise multiple enzymatic activities, such as multiple amylases, or a cocktail of enzymes including any combination of the following: aminopeptidase, amylase β-, or α-, or gluco-amylase), carbohydrase, carboxypeptidase, catalase, cellulase, chitinase, cutinase, cyclodextrin glycosyltransferase, deoxyribonuclease, esterase, α-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, and/or xylanase, or any combination thereof for removing biofilms. The additional enzyme(s) may be producible by means of a microorganism belonging to the genera *Aspergillus*, *Trichoderma*, *Humicola* (e.g., *H. insolens*), and *Fusarium*. Exemplary members from the *Aspergillus* genus include *Aspergillus aculeatus*, *A. awamori*, *A. niger*, and *A. oryzae*. Exemplary members of the *Fusarium* genus include *F. bactridioides*, *F. cerealis*, *F. crookwellense*, *F. culmorum*, *F. graminearum*, *F. graminum*, *F. heterosporum*, *F. negundinis*, *F. oxysporum*, *F. reticulatum*, *F. roseum*, *F. sambucinum*, *F. sarcochroum*, *F. sulphureum*, *F. torulosum*, *F. trichothecioides*, and *F. venenatum*.

The *Bacillus* sp. strain TS-23 α-amylase or variant thereof, comprising compositions may be prepared in accordance with methods known in the art and may be in the form of a liquid or a dry composition. For instance, the *Bacillus* sp. strain TS-23 α-amylase or variant thereof, containing composition may be in the form of a granulate or a microgranulate. The polypeptide to be included in the composition may be stabilized in accordance with methods known in the art.

Examples are given below of exemplary uses of the polypeptide compositions. The dosage of the *Bacillus* sp. strain TS-23 α-amylase or variant thereof, containing composition and other conditions under which the composition is used may be determined using methods known in the art.

The *Bacillus* sp. strain TS-23 α-amylases or variants thereof, are further contemplated for use in a composition along with a 2,6-β-D-fructan hydrolase or variant thereof.

Another aspect contemplates compositions and methods for disintegrating and/or removing biofilms. The term "disintegration" as used herein is to be understood as hydrolysis of polysaccharides in a biofilm matrix connecting and binding together individual microbial cells in the biofilm, whereby the microbial cells can be released and removed from the biofilm. The biofilm is typically present at a surface and the disintegration of the biofilm can be achieved by bringing the surface in contact, e.g., by immersing, covering or splashing the surface with an aqueous medium comprising a *Bacillus* sp. strain TS-23 α-amylase or variant thereof, or one or more other enzymes responsible for breaking down biofilms, such as but not limited to 2,6-β-D-fructan hydrolase. The composition can be used to hydrolyse slime, e.g., in white waters in the pulping and paper industry.

The *Bacillus* sp. strain TS-23 α-amylases or variants thereof, may be present in the amount of 0.0001 to 10000 mg/L; 0.001-1000 mg/L; 0.01-100 mg/L; or 0.1-10 mg/L. Additional enzymes and enzyme variants may be present in similar amounts or less.

The process may suitably be performed at temperatures from about ambient temperature to about 70° C. Exemplary temperature ranges include from about 30° C. to about 60° C., e.g., about 40° C. to about 50° C.

A suitable pH for the hydrolyzing biofilms lies within from about 3.5 to about 8.5. Exemplary pH ranges include from about 5.5 to about 8, e.g. from about 6.5 to about 7.5. The contact time or reaction time for the enzyme to effectively removing a biofilm may vary considerably, depending on the biofilm properties and the frequency of which a surface is treated with the enzyme alone or in combination with other biofilm degrading enzymes, such as 2,6-β-D-fructan hydrolase. Exemplary reaction time can include within about 0.25 to about 25 hours, and from about 1 to about 10 hours, e.g. about 2 hours.

Additional biofilm degrading enzymes that can be combined with the *Bacillus* sp. strain TS-23 α-amylase or variants thereof, and 2,6-β-D-fructan hydrolases include but are not limited to cellulases, hemicellulases, xylanases, other amylases including other α-amylases, lipases, proteases, and/or pectinases.

The *Bacillus* sp. strain TS-23 α-amylase or variants thereof, can further be combined with antimicrobial agents such as enzymatic or non-enzymatic biocides. An enzymatic biocide may, e.g., be a composition comprising an oxidoreductase, e.g. a laccase or a peroxidase, especially haloperoxidase, and optionally an enhancing agent, such as an alkyl syringate, as described for example in International PCT applications WO 97/42825 and DK 97/1273.

The surface from which a biofilm for example can be removed and/or cleaned off is a hard surface, which by definition relates to any surface that is essentially non-permeable to microorganisms. Examples of surfaces are surfaces made from metal, e.g. stainless steel alloys, plastics/synthetic polymers, rubber, board, glass, wood, paper, textile, concrete, rock, marble, gypsum and ceramic materials which optionally may be coated, e.g. with paint, enamel, polymers and the like. Accordingly, the surface may be a member of a system holding, transporting, processing, or in contact with aqueous solutions such as water supply systems, food processing systems, cooling systems, chemical processing systems or pharmaceutical processing systems. The compositions and methods of using the compositions for removing biofilm in the wood processing industry, such as the pulp and/or paper industry. Accordingly, the enzyme and compositions containing the enzyme are useful in a conventional cleaning-in-place (C-I-P) system. The surface may a member of a system unit such as pipes, tanks, pumps, membranes, filters, heat exchangers, centrifuges, evaporators, mixers, spray towers, valves and reactors. The surface may also be or be a part of utensils used in the medical science and industry such as contaminated endoscopes, prosthetic devices or medical implants.

The compositions for biofilm removal is also contemplated for preventing so-called bio-corrosion occurring when a metal surface, e.g. a pipeline, is attacked by a microbial biofilm, that is by disintegrating the biofilm thereby preventing the microbial cells of the biofilm from creating a biofilm environment, which corrodes the metal surface to which it is attached.

Another application for anti-biofilm compositions is for oral care. The surface may however also be of biological origin, such as mucous membranes, skin, teeth, hair, nails etc.

Teeth with dental plaque, e.g., by incorporating the enzymes into toothpaste, and contaminated contact lenses are encompassed as surfaces. Accordingly, a *Bacillus* sp. strain TS-23 α-amylase or variants thereof, can be used for compositions and processes for making a medicament for disintegration of plaque present on a human or animal tooth. A further use is disintegration of biofilm from mucous membranes, such as biofilm in lungs in patients suffering from cystic fibrosis.

Accordingly, in a still further aspect relates to an oral care composition comprising a recombinant enzyme, such as a purified enzyme that is essentially free of any active contaminants. An oral care composition may suitably comprise an amount of a recombinant enzyme.

Other biofilm degrading enzymes for use in oral care compositions include but are not limited to 2,6-β-D-fructan hydrolase activity in the oral care composition. Contemplated enzyme activities include activities from the group of enzymes comprising dextranase; mutanases; oxidases, such as glucose oxidase, L-amino acid oxidase, peroxidases, such as e.g. the *Coprinus* sp. peroxidases described in WO 95/10602, or lactoperoxidase, haloperoxidases, especially haloperoxidase derivable from *Curvularia* sp., in particular *C. verruculosa* and *C. inaequalis*; laccases; proteases such as papain, acidic protease (e.g. the acidic proteases described in WO 95/02044, endoglucosidases, lipases, amylases, including amyloglucosidases, such as AMG (Novo Nordisk A/S); anti-microbial enzymes, and mixtures thereof.

The oral care composition may have any suitable physical form (i.e. powder, paste, gel, liquid, ointment, tablet etc.). An "oral care composition" includes a composition, which can be used for maintaining or improving the oral hygiene in the mouth of humans and animals, by preventing dental caries, preventing the formation of dental plaque and tartar, removing dental plaque and tartar, preventing and/or treating dental diseases etc. At least in the context oral care compositions do also encompass products for cleaning dentures, artificial teeth and the like. Examples of such oral care compositions includes toothpaste, dental cream, gel or tooth powder, odontic mouth washes, pre- or post brushing rinse formulations, chewing gum, lozenges, and candy. Toothpastes and tooth gels typically include abrasive polishing materials, foaming agents, flavoring agents, humectants, binders, thickeners, sweetening agents, whitening/bleaching/stain removing agents, water, and optionally additional enzymes and enzyme combinations.

Mouthwashes, including plaque-removing liquids, typically comprise a water/alcohol solution, flavor, humectant, sweetener, foaming agent, colorant, and optionally additional enzymes or enzyme combinations.

Abrasive polishing material might also be incorporated into the oral care composition such as a dentifrice.

Accordingly, abrasive polishing material can include alumina and hydrates thereof, such as a alumina trihydrate; magnesium trisilicate; magnesium carbonate; kaolin; aluminosilicates, such as calcined aluminum silicate and aluminum silicate; calcium carbonate; zirconium silicate; and also powdered plastics, such as polyvinyl chloride; polyamides; polymethyl methacrylate; polystyrene; phenol-formaldehyde resins; melamine-formaldehyde resins; urea-formaldehyde resins; epoxy resins; powdered polyethylene; silica xerogels; hydrogels and aerogels and the like. Also suitable as abrasive agents are calcium pyrophosphate; water-insoluble alkali metaphosphates; dicalcium phosphate and/or its dihydrate, dicalcium orthophosphate; tricalcium phosphate; particulate hydroxyapatite and the like. It is also possible to employ mixtures of these substances.

Dependent on the oral care composition, the abrasive product may be present in from about 0% to about 70% by weight, or from about 1% to about 70%. For toothpastes, the abrasive material content typically lies in the range of from 10% to 70% by weight of the final toothpaste.

Humectants are employed to prevent loss of water from e.g. tooth pastes. Suitable humectants for use in oral care compositions include the following compounds and mixtures thereof: glycerol; polyol; sorbitol; polyethylene glycols (PEG); propylene glycol; 1,3-propanediol; 1,4-butanediol; hydrogenated partially hydrolyzed polysaccharides and the like. Humectants are in general present in from 0% to about 80%, or from about 5% to about 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilizing a dentifrice product. Thickeners may be present in toothpaste creams and gels in an amount of from about 0.1% to about 20% by weight, and binders to the extent of from about 0.01 to about 10% by weight of the final product.

As foaming agent soap, anionic, cationic, non-ionic, amphoteric and/or zwitterionic surfactants can be used. These may be present at levels of from 0% to about 15%, from about 0.1% to about 13%, or from about 0.25% to about 10% by weight of the final product.

Surfactants are only suitable to the extent that they do not exert an inactivation effect on the *Bacillus* sp. strain TS-23 α-amylase or variants thereof. Surfactants include fatty alcohol sulfates, salts of sulfonated mono-glycerides or fatty acids having 10 to 20 carbon atoms, fatty acid-albumen condensation products, salts of fatty acids amides and taurines and/or salts of fatty acid esters of isethionic acid.

Suitable sweeteners include saccharin for use in the formulations.

Flavors, such as spearmint, are usually present in low amounts, such as from about 0.01% to about 5% by weight, especially from about 0.1% to about 5%. Whitening/bleaching agents include $H_2O_2$ and may be added in amounts less that about 5%, or from about 0.25% to about 4%, calculated by the weight of the final product. The whitening/bleaching agents may be an enzyme, such as an oxidoreductase. Examples of suitable teeth bleaching enzymes, such as those described in WO 97/06775.

Water is usually added in an amount giving e.g. toothpaste a flowable form.

Further water-soluble anti-bacterial agents, such as chlorohexidine digluconate, hexetidine, alexidine, Triclosan®, quaternary ammonium anti-bacterial compounds and water-soluble sources of certain metal ions such as zinc, copper, silver and stannous (e.g., zinc, copper and stannous chloride, and silver nitrate) may also be included.

Also contemplated is the addition of compounds that can be used as fluoride source, dyes/colorants, preservatives, vitamins, pH-adjusting agents, anti-caries agents, desensitizing agents, etc.

Biofilm degrading enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids, which form the structural components of bacterial cell walls and membranes.

Dextranase and other carbohydrases, such as the 2,6-β-D-fructan hydrolase, break down the organic skeletal structure produced by bacteria that forms a matrix for bacterial adhesion. Proteases and amylases, not only prevent plaque formation, but also prevent the development of calculus by breaking-up the carbohydrate-protein complex that binds calcium, preventing mineralization.

A toothpaste may typically comprise the following ingredients (in weight % of the final toothpaste composition): abrasive material to about 70%; humectant: 0% to about 80%; thickener: about 0.1% to about 20%; binder: about 0.01% to about 10%; sweetener: about 0.1% to about 5%; foaming agent: 0% to about 15%; whitener: 0% to about 5%; and enzymes: about 0.0001% to about 20%.

In a specific embodiment, a toothpaste has a pH in the range from about 6.0 to about 8.0, and comprises: a) about 10% to about 70% abrasive material; b) 0% to about 80% humectant; c) 0.1% to about 20% thickener; d) 0.01% to about 10% binder; e) about 0.1% to about 5% sweetener; f) 0% to about 15% foaming agent; g) 0% to about 5% whitener; i) about 0.0001% to about 20% enzymes.

Said enzymes referred to under i) include a *Bacillus* sp. strain TS-23 α-amylase or variants thereof, alone, or in combination with other biofilm degrading enzymes, such as 2,6-β-D-fructan hydrolase, and optionally other types of enzymes mentioned above known to be used in toothpastes and the like.

A mouth wash may typically comprise the following ingredients (in weight % of the final mouth wash composition): 0% to about 20% humectant; 0% to about 2% surfactant; 0% to about 5% enzymes; 0% to about 20% ethanol; 0% to about 2% other ingredients (e.g. flavor, sweetener active ingredients such as fluorides). The composition can also contain from about 0% to about 70% water.

The mouth wash composition may be buffered with an appropriate buffer e.g. sodium citrate or phosphate in the pH-range of about 6.0 to about 7.5. The mouth wash may be in non-diluted form (i.e. must be diluted before use).

The oral care compositions may be produced using any conventional method known to the art of oral care.

4.4 Starch Processing Compositions and Use

In another aspect, compositions with a disclosed *Bacillus* sp. strain TS-23 α-amylase or variants thereof, can be utilized for starch liquefaction or saccharification.

One aspect contemplates compositions and uses of compositions to produce sweeteners from starch. A "traditional" process for conversion of starch to fructose syrups normally consists of three consecutive enzymatic processes, viz. a liquefaction process followed by a saccharification process, and an isomerization process. During the liquefaction process, starch is degraded to dextrins by a *Bacillus* sp. strain TS-23 α-amylase or variants thereof, at pH values between about 5.5 and about 6.2 and at temperatures of about 95° C. to about 160° C. for a period of approximately 2 hours. In order to ensure optimal enzyme stability under these conditions, 1 mM of calcium is added (40 ppm free calcium ions). Starch processing is useful for producing alcohol (e.g., cereal liquefaction for fuel and potable alcohol, alcohol brewing), starch liquefaction for sweetener production, cane sugar processing, and other food related starch processing goals. Other conditions can be used for different *Bacillus* sp. strain TS-23 α-amylases or variants thereof.

After the liquefaction process, the dextrins are converted into dextrose by addition of a glucoamylase (e.g. AMG™) and a debranching enzyme, such as an isoamylase or a pullulanase (e.g., PROMOZYME®). Before this step, the pH is reduced to a value below about 4.5, maintaining the high temperature (above 95° C.), and the liquefying *Bacillus* sp. strain TS-23 α-amylase or variant thereof, activity is denatured. The temperature is lowered to 60° C., and a glucoamylase and a debranching enzyme can be added. The saccharification process proceeds typically for about 24 to about 72 hours.

After the saccharification process, the pH is increased to a value in the range of about 6.0 to about 8.0, e.g., pH 7.5, and the calcium is removed by ion exchange. The dextrose syrup is then converted into high fructose syrup using, e.g., an immobilized glucose isomerase (such as Sweetzyme®).

At least one enzymatic improvement of this process can be performed. Reduction of the calcium dependency of the liquefying *Bacillus* sp. strain TS-23 α-amylase or variant thereof. Addition of free calcium is required to ensure adequately high stability of the *Bacillus* sp. strain TS-23 α-amylase or variant thereof, but free calcium strongly inhibits the activity of the glucose isomerase and needs to be removed, by means of an expensive unit operation, to an extent that reduces the level of free calcium to below 3-5 ppm. Cost savings can be obtained if such an operation could be avoided, and the liquefaction process could be performed without addition of free calcium ions.

For example, a less calcium-dependent enzyme, which is stable and highly active at low concentrations of free calcium (<40 ppm) can be utilized in the composition and procedures. Such a *Bacillus* sp. strain TS-23 α-amylase or variant thereof should have a pH optimum at a pH in the range of about 4.5 to about 6.5, or in the range of about 4.5 to about 5.5.

A *Bacillus* sp. strain TS-23 α-amylase or variant thereof can be used in laboratory and in industrial settings to hydrolyze starch or any maltodextrine-comprising compound for a variety of purposes. These *Bacillus* sp. strain TS-23 α-amylases or variants thereof can be used alone to provide specific hydrolysis or can be combined with other amylases to provide a "cocktail" with a broad spectrum of activity. Exemplary uses include the removal or partial or complete hydrolysis of starch or any maltodextrine-comprising compound from biological, food, animal feed, pharmaceutical, or industrial samples.

Another aspect contemplates compositions and methods of using the compositions in a fermentation process, wherein a starch substrate is liquefied and/or saccharified in the presence of the *Bacillus* sp. strain TS-23 α-amylase or variant thereof to produce glucose and/or maltose suitable for conversion into a fermentation product by a fermenting organism, such as a yeast. Such fermentation processes include a process for producing ethanol for fuel or drinking ethanol (potable alcohol), a process for producing a beverage, a process for producing desired organic compounds (e.g., such as citric acid, itaconic acid, lactic acid, gluconic acid, sodium gluconate, calcium gluconate, potassium gluconate, glucono delta lactone, or sodium erythorbate), ketones, amino acids (such as glutamic acid, sodium monoglutaminate), but also more complex compounds (e.g., antibiotics, such as penicillin, tetracyclin), enzymes, vitamins (e.g., riboflavin, vitamin $B_{12}$, β-carotene), and hormones, which are difficult to produce synthetically.

The starch to be processed may be a highly refined starch quality, such as at least 90%, at least 95%, at least 97%, or at least 99.5% pure. Alternatively, the starch can be a more crude starch containing material comprising milled whole grain including non-starch fractions such as germ residues and fibers. The raw material, such as whole grain, is milled in order to open up the structure and allowing for further processing. Two milling processes can be used: wet and dry milling. Also, corn grits such as milled corn grits may be applied.

Dry milled grain will, in addition to starch, comprise significant amounts of non-starch carbohydrate compounds. When such a heterogeneous material is processed by jet cooking *Bacillus* sp. strain TS-23 often only a partial gelatinization of the starch is achieved. As the *Bacillus* sp. strain TS-23 α-amylase or variant thereof has a high activity towards ungelatinized starch, the enzyme(s) may be advantageously applied in a process comprising liquefaction and/or saccharification jet cooked dry milled starch.

Furthermore, due to the superior hydrolysis activity of the *Bacillus* sp. strain TS-23 α-amylases or variants thereof, the need for glucoamylase during the saccharification step is greatly reduced. This allows saccharification to be performed at very low levels of glucoamylase activity. Glucoamylase activity is either absent, or if present, then present in an amount of no more than or even less than 0.5 AGU/g DS, or no more than or even less than 0.4 AGU/g DS, or no more than or even less than about 0.3 AGU/g DS, or less than 0.1 AGU, such as no more than or even less than about 0.05 AGU/g DS of starch substrate. "DS" is the unit of enzyme added per gram of dry solid substrate. Expressed in mg enzyme protein, the enzyme having glucoamylase activity is either absent or present in an in an amount of no more than or even less than about 0.5 mg EP/g DS, or no more than or even less than about 0.4 mg EP/g DS, or no more than or even less than about 0.3 mg EP/g DS, or no more than or even less than about 0.1 mg EP/g DS (e.g., no more than or even less than about 0.05 mg EP/g DS or no more than or even less than 0.02 mg EP/g DS of starch substrate). The glucoamylase may be derived from a strain within *Aspergillus* sp., *Talaromyces* sp., *Pachykytospora* sp., or *Trametes* sp., with exemplary examples being *Aspergillus niger, Talaromyces emersonii, Trametes cingulata,* or *Pachykytospora papyracea.*

The process may comprise a) contacting a starch substrate with a *Bacillus* sp. strain TS-23 α-amylase or variant thereof comprising a catalytic module having α-amylase activity and a carbohydrate-binding module, e.g., the polypeptide of the first aspect; b) incubating said starch substrate with said enzyme for a time and at a temperature sufficient to achieve conversion of at least 90%, at least 91%, at least 92%, at least 93%, at least 94%, at least 95%, at least 96%, at least 97%, at least 98%, at least 99%, or even at least 99.5% w/w of said starch substrate into fermentable sugars; c) fermenting to produce a fermentation product; and d) optionally recovering the fermentation product. During the process steps b) and/or c), an enzyme having glucoamylase activity is either absent or present in an amount from 0.001 to 2.0 AGU/g DS, from 0.01 to 1.5 AGU/g DS, from 0.05 to 1.0 AGU/g DS, from 0.01 to 0.5 AGU/g DS. The enzyme having glucoamylase activity can either absent or present in an amount of no more than or even less than 0.5 AGU/g DS, or no more than or even less than 0.4 AGU/g DS, or no more than or even less than 0.3 AGU/g DS, or no more than or even less than 0.1 AGU/g DS (e.g., no more than or even less than 0.05 AGU/g DS of starch substrate). Expressed in mg enzyme protein, the enzyme having glucoamylase activity is either absent or present in an in an amount of no more than or even less than 0.5 mg EP/g DS, or no more than or even less than 0.4 mg EP/g DS, or no more than or even less than 0.3 mg EP/g DS, or no more than or even less than 0.1 mg EP/g DS (e.g., no more than or even less than 0.05 mg EP/g DS or no more than or even less than 0.02 mg EP/g DS of starch substrate). In the process steps a), b), c), and/or d) may be performed separately or simultaneously.

In another aspect the process may comprise: a) contacting a starch substrate with a yeast cell transformed to express a *Bacillus* sp. strain TS-23 α-amylase or variant thereof comprising a catalytic module having α-amylase activity and a carbohydrate-binding module; b) incubating said starch substrate with said yeast for a time and at a temperature sufficient to achieve conversion of at least 90% w/w of said starch substrate into fermentable sugars; c) fermenting to produce ethanol; d) optionally recovering ethanol. The steps a), b), and c) may performed separately or simultaneously.

In yet another aspect, the process comprising hydrolysis of a slurry of gelatinized or granular starch, in particular hydrolysis of granular starch into a soluble starch hydrolysate at a temperature below the initial gelatinization temperature of said granular starch. In addition to being contacted with a polypeptide comprising a catalytic module having α-amylase activity and a carbohydrate-binding module. The starch can be contacted with any one or more of the following a fungal α-amylase (EC 3.2.1.1) and one or more of the following: a β-amylase (EC 3.2.1.2), and a glucoamylase (EC 3.2.1.3). In a further aspect, another amylolytic enzyme or a debranching enzyme, such as an isoamylase (EC 3.2.1.68), or a pullulanases (EC 3.2.1.41) may be added to the *Bacillus* sp. strain TS-23 α-amylase or variant thereof.

In an embodiment, the process is conducted at a temperature below the initial gelatinization temperature. Such processes are oftentimes conducted at least at 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or at least 60° C. The pH at which the process is conducted may in be in the range of about 3.0 to about 7.0, or from about 3.5 to about 6.0, or from about 4.0 to about 5.0. One aspect contemplates a process comprising fermentation, e.g. with a yeast to produce ethanol, e.g., at a temperature around 32° C., such as from 30° C. to 35° C.

In another aspect, the process comprises simultaneous saccharification and fermentation, e.g., with a yeast to produce ethanol, or another suitable fermentation organism to produce a desired organic compound, such as at a temperature from 30° C. to 35° C., e.g., at around 32° C.

In the above fermentation processes, the ethanol content reaches at least about 7%, at least about 8%, at least about 9%, at least about 10%, at least about 11%, at least about 12%, at least about 13%, at least about 14%, at least about 15% such as at least about 16% ethanol.

The starch slurry to be used in any of the above aspects may have about 20% to about 55% dry solids granular starch, about 25% to about 40% dry solids granular starch, or from about 30% to about 35% dry solids granular starch. After being contacted with a *Bacillus* sp. strain TS-23 α-amylase or variant thereof, the enzyme converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another embodiment, a *Bacillus* sp. strain TS-23 α-amylase or variant thereof comprises a catalytic module having α-amylase activity and a carbohydrate-binding module, e.g., the polypeptide of the first aspect, is used in a process for liquefaction, saccharification of a gelatinized starch, e.g., but not limited to gelatinization by jet cooking. The process may comprise fermentation to produce a fermentation product, e.g., ethanol. Such a process for producing ethanol from starch-containing material by fermentation comprises: (i) liquefying said starch-containing material with a polypeptide comprising a catalytic module having α-amylase activity and a carbohydrate-binding module, e.g., the polypeptide of the first aspect; (ii) saccharifying the liquefied mash obtained; and (iii) fermenting the material obtained in step (ii) in the presence of a fermenting organism. Optionally the process further comprises recovery of the ethanol. The saccharification and fermentation processes may be carried out as a simultaneous saccharification and fermentation process (SSF process). During the fermentation, the ethanol content reaches at least about 7%, at least about 8%, at least about 9%, at least about 10% such as at least about 11%, at least about 12%, at least about 13%, at least about 14%, at least 15% such as at least 16% ethanol.

The starch to be processed in the processes of the above aspects may in particular be obtained from tubers, roots, stems, legumes, cereals or whole grain. More specifically, the granular starch may be obtained from corns, cobs, wheat, barley, rye, milo, sago, cassava, tapioca, sorghum, rice, peas, bean, banana, or potatoes. Also contemplated are both waxy and non-waxy types of corn and barley.

The composition described above may be used for liquefying and/or saccharifying a gelatinized or a granular starch, and a partly gelatinized starch. A partly gelatinized starch is a starch that to some extent is gelatinized, i.e., wherein part of the starch has irreversibly swelled and gelatinized and part of the starch is still present in a granular state.

The composition described above may comprise an acid α-amylase variant present in an amount of 0.01 to 10.0 AFAU/g DS, or 0.1 to 5.0 AFAU/g DS, or 0.5 to 3.0 AFAU/AGU, or 0.3 to 2.0 AFAU/g DS. The composition may be applied in any of the starch processes described above.

As used herein, the term "liquefaction" or "liquefy" means a process by which starch is converted to shorter chain and less viscous dextrins. Generally, this process involves gelatinization of starch simultaneously with or followed by the addition of a *Bacillus* sp. strain TS-23 α-amylase or variant thereof. Additional liquefaction inducing enzymes may also be added.

As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from 200-300° F., e.g., 220-235° F. Subsequent to application to a heat exchange or jet temperature, the slurry is held for a period of 3-10 minutes at that temperature. This step of holding the slurry at 200-300° F. is primary liquefaction.

As used herein, the term "secondary liquefaction" refers the liquefaction step subsequent to primary liquefaction (heating to 200-300° F.), when the slurry is allowed to cool to atmospheric temperature. This cooling step can be 30 minutes to 180 minutes (3 hours), e.g. 90 minutes to 120 minutes (2 hours).

As used herein, the term "minutes of secondary liquefaction" refers to the time that has elapsed from the start of secondary liquefaction, to the time that the DE is measured.

Another aspect contemplates the additional use of a β-amylase in the composition comprising *Bacillus* sp. strain TS-23 α-amylase or variant thereof. β-amylases (EC 3.2.1.2) are exo-acting maltogenic amylases, which catalyze the hydrolysis of 1,4-α-glucosidic linkages in to amylose, amylopectin, and related glucose polymers, thereby releasing maltose.

β-amylases have been isolated from various plants and microorganisms (W. M. Fogarty and C. T. Kelly, PROGRESS IN INDUSTRIAL MICROBIOLOGY, vol. 15, pp. 112-115, 1979). These β-amylases are characterized by having optimum temperatures in the range from 40° C. to 65° C., and optimum pH in the range from about 4.5 to about 7.0. Contemplated β-amylases include, but are not limited to, β-amylases from barley SPEZYME® BBA 1500, SPEZYME® DBA, OPTIMALT® ME, OPTIMALT® BBA (Genencor International Inc.) and NOVOZYM™ WBA (Novozymes A/S).

Another enzyme contemplated for use in the composition is a glucoamylase (EC 3.2.1.3). Glucoamylases are derived from a microorganism or a plant. Exemplary glucoamylases are of fungal or bacterial origin. Exemplary bacterial glucoamylases are *Aspergillus* glucoamylases, in particular *A. niger* G1 or G2 glucoamylase (Boel et al., *EMBO J.* 3(5): 1097-1102 (1984), or variants thereof, such as disclosed in WO 92/00381; and WO 00/04136; the *A. awamori* glucoamylase (WO 84/02921); *A. oryzae* (*Agric. Biol. Chem.*, 55(4): 941-949 (1991)), or variants or fragments thereof.

Other contemplated *Aspergillus* glucoamylase variants include variants to enhance the thermal stability: G137A and G139A (Chen et al., *Prot. Eng.* 9: 499-505 (1996)); D257E and D293E/Q (Chen et al., *Prot. Eng.* 8: 575-582 (1995)); N182 (Chen et al., *Biochem. J.* 301: 275-281 (1994)); disulfide bonds, A246C (Fierobe et al., *Biochemistry*, 35: 8698-8704 (1996)); and introduction of Pro residues in positions A435 and S436 (Li et al., *Protein Eng.* 10: 1199-1204 (1997)). Other contemplated glucoamylases include and *Talaromyces* glucoamylases, in particular derived from *Talaromyces emersonii* (WO 99/28448), *Talaromyces leycettanus* (U.S. Pat. No. RE 32,153), *Talaromyces duponti*, *Talaromyces thermophilus* (U.S. Pat. No. 4,587,215). Bacterial glucoamylases contemplated include glucoamylases from the genus *Clostridium*, in particular *C. thermoamylolyticum* (EP 135138) and *C. thermohydrosulfuricum* (WO 86/01831). Exemplary glucoamylases include the glucoamylases derived from *Aspergillus oryzae*. Also contemplated are the commercial glucoamylases such as AMG 200L; AMG 300 L; SAN™ SUPER and AMG™ E (Novozymes); OPTIDEX®300 (from Genencor International, Inc.); AMIGASE® and AMIGASE® PLUS (DSM); G-ZYME® G900 (Enzyme Bio-Systems); G-ZYME® G990 ZR (*A. niger* glucoamylase and low protease content).

Glucoamylases may be added in an amount of 0.02-2.0 AGU/g DS, or 0.1-1.0 AGU/g DS, such as 0.2 AGU/g DS.

Additional enzymes and enzyme variants are also contemplated for inclusion in the composition. One or more α-amylases can be used in addition to a *Bacillus* sp. strain TS-23 α-amylase or variant thereof, or can further include other enzymes discussed herein.

Another enzyme that can optionally be added is a debranching enzyme, such as an isoamylase (EC 3.2.1.68) or a pullulanase (EC 3.2.1.41). Isoamylase hydrolyses α-1,6-D-glucosidic branch linkages in amylopectin and β-limit dextrins and can be distinguished from pullulanases by the inability of isoamylase to attack pullulan, and by the limited action on α-limit dextrins. Debranching enzymes may be added in effective amounts well known to the person skilled in the art.

The exact composition of the products of the process depends on the combination of enzymes applied as well as the type of granular starch processed. For example, the soluble hydrolysate can be maltose with a purity of at least about 85%, at least about 90%, at least about 95.0%, at least about 95.5%, at least about 96.0%, at least about 96.5%, at least about 97.0%, at least about 97.5%, at least about 98.0%, at least about 98.5, at least about 99.0% or at least about 99.5%. Alternatively, the soluble starch hydrolysate can be glucose or the starch hydrolysate has a DX (glucose percent of total solubilized dry solids) of at least 94.5%, at least 95.0%, at least 95.5%, at least 96.0%, at least 96.5%, at least 97.0%, at least 97.5%, at least 98.0%, at least 98.5, at least 99.0% or at least 99.5%. The process can include a product which is a specialty syrup, such as a specialty syrup containing a mixture of glucose, maltose, DP3 and DPn for use in the manufacture of ice creams, cakes, candies, canned fruit.

Two milling processes are: wet and dry milling. In dry milling, the whole kernel is milled and used. Wet milling gives a good separation of germ and meal (starch granules and protein), and is with a few exceptions, applied at locations where the starch hydrolysate is used in production of syrups. Both dry and wet milling are well known in the art of starch processing and are equally contemplated for use with the compositions and methods disclosed. The process may be conducted in an ultrafiltration system where the retentate is held under recirculation in presence of enzymes, raw starch and water and where the permeate is the soluble starch hydrolysate. Equally contemplated is the process conducted in a continuous membrane reactor with ultrafiltration membranes and where the retentate is held under recirculation in presence of enzymes, raw starch and water, and where the permeate is the soluble starch hydrolysate. Also contemplated is the process conducted in a continuous membrane reactor with microfiltration membranes and where the retentate is held under recirculation in presence of enzymes, raw starch and water, and where the permeate is the soluble starch hydrolysate.

In one regard, the soluble starch hydrolysate of the process is subjected to conversion into high fructose starch-based syrup (HFSS), such as high fructose corn syrup (HFCS). This conversion can be achieved using a glucose isomerase, and by an immobilized glucose isomerase supported on a solid support. Contemplated isomerases include the commercial products Sweetzyme®, IT (Novozymes A/S); G-ZYME® IMGI, and G-ZYME® G993, KETOMAX™, G-ZYME® G993 (Rhodia); G-ZYME® G993 liquid, GENSWEET® IGI (Genencor International, Inc.).

In another aspect, the soluble starch hydrolysate produced by these methods can be used in the production of fuel or potable ethanol. In the process of the third aspect the fermentation may be carried out simultaneously or separately/sequential to the hydrolysis of the granular starch slurry. When the fermentation is performed simultaneous to the hydrolysis, the temperature is between 30° C. and 35° C., or between 31° C. and 34° C. The process may be conducted in an ultrafiltration system where the retentate is held under recirculation in presence of enzymes, raw starch, yeast, yeast nutrients and water and where the permeate is an ethanol containing liquid. Equally contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process may also be used for production of a fermentation product comprising fermenting the treated starch into a fermentation product, such as citric acid, monosodium glutamate, gluconic acid, sodium gluconate, calcium gluconate, potassium gluconate, glucono delta lactone, or sodium erythorbate.

The amylolytic activity of a *Bacillus* sp. strain TS-23 α-amylase or variant thereof may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch, the blue color gets weaker and gradually turns into a reddish-brown, which is compared to a colored glass standard.

5. METHODS 5.1 Filter Screening Assays

The assays discussed below may be used in the screening of AmyTS23 α-amylase variants having altered stability at high or low pH and/or under $Ca^{2+}$ depleted conditions compared to the parent α-amylase enzyme.

5.2 High pH Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with 10 micro g/ml kanamycin at 37° C. for at least 21 hours. The cellulose acetate layer is located on the TY agar plate.

Each filter sandwich is specifically marked with a needle after plating, but before incubation in order to be able to localize positive variants on the filter and the nitrocellulose filter with bound variants is transferred to a container with glycin-NaOH buffer, pH 8.6-10.6 and incubated at room temperature (can be altered from 10-60° C.) for 15 min. The cellulose acetate filters with colonies are stored on the TY-plates at room temperature until use. After incubation, residual activity is detected on plates containing 1% agarose, 0.2% starch in glycin-NaOH buffer, pH 8.6-10.6. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

5.3 Low Calcium Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dassel, Germany) on TY agar plates with a relevant antibiotic, e.g., kanamycin or chloramphenicol, at 37° C. for at least 21 hours. The cellulose-acetate layer is located on the TY agar plate.

Each filter sandwich is specifically marked with a needle after plating, but before incubation in order to be able to localize positive variants on the filter and the nitrocellulose filter with bound variants is transferred to a container with carbonate/bicarbonate buffer pH 8.5-10 and with different EDTA concentrations (0.001 mM-100 mM). The filters are incubated at room temperature for 1 hour. The cellulose acetate filters with colonies are stored on the TY-plates at room temperature until use. After incubation, residual activity is detected on plates containing 1% agarose, 0.2% starch in carbonate/bicarbonate buffer pH 8.5-10. The assay plates with nitrocellulose filters are marked the same way as the filter sandwich and incubated for 2 hours at room temperature. After removal of the filters the assay plates are stained with 10% Lugol solution. Starch degrading variants are detected as white spots on dark blue background and then identified on the storage plates. Positive variants are rescreened twice under the same conditions as the first screen.

5.4 Low pH Filter Assay

*Bacillus* libraries are plated on a sandwich of cellulose acetate (OE 67, Schleicher & Schuell, Dassel, Germany)—and nitrocellulose filters (Protran-Ba 85, Schleicher & Schuell, Dasseli Germany) on TY agar plates with 10 micro g/ml chloramphenicol at 37° C. for at least 21 hours. The cellulose acetate layer is located on the TY agar plate.

Each filter sandwich is specifically marked with a needle after plating, but before incubation in order to be able to localize positive variants on the filter, and the nitrocellulose filter with bound variants is transferred to a container with citrate buffer, pH 4.5 and incubated at 80° C. for 20 minutes (when screening for variants in the wild type backbone) or 85° C. for 60 minutes (when screening for variants of the parent α-amylase). The cellulose acetate filters with colonies are stored on the TY-plates at room temperature until use. After incubation, residual activity is detected on assay plates containing 1% agarose, 0.2% starch in citrate buffer, pH 6.0. The assay plates with nitrocellulose filters are marked the same way as the filter sandwich and incubated for 2 hours at 50° C. After removal of the filters the assay plates are stained with 10% Lugol solution. Starch degrading variants are detected as white spots on dark blue background and then identified on the storage plates. Positive variants are re-screened twice under the same conditions as the first screen.

5.5 Secondary Screening

Positive transformants after rescreening are picked from the storage plate and tested in a secondary plate assay. Positive transformants are grown for 22 hours at 37° C. in 5 ml LB+chloramphenicol. The *Bacillus* culture of each positive transformant and as a control a clone expressing the corresponding backbone are incubated in citrate buffer, pH 4.5 at 90° C. and samples are taken at 0, 10, 20, 30, 40, 60 and 80 minutes. A 3 micro liter sample is spotted on an assay plate. The assay plate is stained with 10% Lugol solution. Improved variants are seen as variants with higher residual activity (detected as halos on the assay plate) than the backbone. The improved variants are determined by nucleotide sequencing.

5.6 Stability Assay of Unpurified Variants

The stability of the variants may be assayed as follows: *Bacillus* cultures expressing the variants to be analyzed are grown for 21 hours at 37° C. in 10 ml LB+chloramphenicol. 800 micro liter culture is mixed with 200 μL citrate buffer, pH 4.5. A number of 70 μL aliquots corresponding to the number of sample time points are made in PCR tubes and incubated at 70° C. or 90° C. for various time points (typically 5, 10, 15, 20, 25 and 30 minutes) in a PCR machine. The 0 min sample is not incubated at high temperature. Activity in the sample is measured by transferring 20 μL to 200 μL of the α-amylase PNP-$G_7$ substrate MPR3 ((Boehringer Mannheim Cat. no. 1660730) as described below under "Assays for Alpha-amylase Activity". Results are plotted as percentage activity (relative to the 0 time point) versus time, or stated as percentage residual activity after incubation for a certain period of time.

5.7 Fermentation and Purification of α-amylase Variants

A *B. subtilis* strain harboring the relevant expression plasmid may be fermented and purified as follows: The strain is streaked on a LB-agar plate with 10 μg/ml kanamycin from −80° C. stock, and grown overnight at 37° C. The colonies are transferred to 100 ml PS-1 media supplemented with 10 micro g/ml chloramphenicol in a 500 ml shaking flask.

| Composition of PS-1 medium | |
|---|---|
| Pearl sugar | 100 g/l |
| Soy Bean Meal | 40 g/l |
| $Na_2HPO_4$, $12H_2O$ | 10 g/l |
| Pluronic ™ PE 6100 | 0.1 g/l |
| $CaCO_3$ | 5 g/l |

The culture is shaken at 37° C. at 270 rpm for 5 days.

Cells and cell debris are removed from the fermentation broth by centrifugation at 4500 rpm in 20-25 minutes. Afterwards the supernatant is filtered to obtain a completely clear solution. The filtrate is concentrated and washed on a UF-filter (10000 cut off membrane) and the buffer is changed to 20 mM Acetate pH 5.5. The UF-filtrate is applied on a S-sepharose F.F. and elution is carried out by step elution with 0.2M NaCl in the same buffer. The eluate is dialysed against 10 mM Tris, pH 9.0 and applied on a Q-sepharose F.F. and eluted with a linear gradient from 0-0.3 M NaCl over 6 column volumes. The fractions that contain the activity (measured by the Phadebas assay) are pooled, pH was adjusted to pH 7.5 and remaining color was removed by a treatment with 0.5% W/vol. active charcoal in 5 minutes.

5.8 Specific Activity Determination

The specific activity is determined using the PHADE-BAS® assay (Pharmacia) as activity/mg enzyme. The manufacturer's instructions are followed (see also below under "Assay for Alpha-amylase Activity").

5.9 Determination of Isoelectric Point

The pI is determined by isoelectric focusing (ex: Pharmacia, Ampholine, pH 3.5-9.3).

5.10 Accelerated Stability Assay

In 50 ml Propylene tubes, 10 ml of detergent of interest was added. Appropriate dilution was made to both AmyTS23t and AmyTS23tΔRS so that 180 ppm of each was measured with a pipette into separate tubes containing the detergent. The detergent with each mutant enzyme was vortex for 30 sec and then placed on a RotaMix (ATR RKVS Model) for 10 minutes. 100 µliters of the detergent with the mutant enzyme were measured with a pipette and diluted 1:651. The initial activity of the mutants was assayed using Blocked P-Nitro-Phenyl-Maltoheptaose (Blocked PBNPG7) substrate on a Konelab, Model 20XT. The detergent samples were then incubated in a constant temperature incubator set at 37° C. Samples were removed at 1, 2, 4, 7 and 17 days and the enzyme activity assayed.

5.11 Assays for α-amylase Activity 5.11.1 Phadebas Assay

A-amylase activity is determined by a method employing PHADEBAS® tablets as substrate. Phadebas tablets (PHADEBAS® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric add, 50 mM boric acid, 0.1 mM $CaCl_2$, pH adjusted to the value of interest with NaOH). The test is performed in a water bath at the temperature of interest. The α-amylase to be tested is diluted in x ml of 50 mM Britton-Robinson buffer. 1 ml of this α-amylase solution is added to the 5 ml 50 mM Britton-Robinson buffer. The starch is hydrolyzed by the α-amylase giving soluble blue fragments. The absorbance of the resulting blue solution, measured spectrophotometrically at 620 nm, is a function of the α-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given α-amylase will hydrolyze a certain amount of substrate and a blue color will be produced. The color intensity is measured at 620 nm. The measured absorbance is directly proportional to the specific activity (activity/mg of pure α-amylase protein) of the α-amylase in question under the given set of conditions.

5.11.2 Alternative Method

α-amylase activity is determined by a method employing the PNP-$G_7$ substrate. PNP-$G_7$ which is a abbreviation for p-nitrophenyl-α-D-maltoheptaoside is a blocked oligosaccharide which can be cleaved by an endo-amylase. Following the cleavage, the α-glucosidase included in the kit digest the substrate to liberate a free PNP molecule which has a yellow color and thus can be measured by visible spectophometry at λ=405 nm (400-420 nm). Kits containing PNP-$G_7$ substrate and α-glucosidase are manufactured by Boehringer-Mannheim (cat. No. 1054635).

To prepare the reagent solution 10 ml of substrate/buffer solution is added to 50 ml enzyme/buffer solution as recommended by the manufacturer. The assay is performed by transferring a 20 µL sample to a 96 well microtitre plate and incubating at 25° C. 200 µL reagent solution pre-equilibrated to 25° C. is added. The solution is mixed and pre-incubated 1 minute and absorption is measured every 30 seconds over 4 minutes at OD 405 nm in an ELISA reader.

The slope of the time dependent absorption-curve is directly proportional to the activity of the α-amylase in question under the given set of conditions.

5.12 Determination of Enzyme Performance in Detergent Compositions 5.12.1 US Conditions Use of Terg-o-tometer, United States Testing, Hoboken, N.J.—To simulate washing test under US washing conditions, a dose efficiency curve (DEC) of the mutant enzyme of interest was conducted at 20° C. using standard detergents such as Liquid AATCC 2003 Without Optical Brightener and/or Powder AATCC 1993 (American Association of Textile Chemists and Colorists). A corresponding DEC of a comparative α-amylase was then conducted to compare the stain removal performance of the inventive mutant enzyme. This process was repeated at 40° C. Typically, 4 swatches of CS-28 Rice Starch stain (CFT of Holland) were placed in a steel container of the Terg-o-tometer, which was filled with 1 Liter of DI water and 1.5 g of Liquid AATCC. When Powder AATCC was used, 1.5 g of the detergent powder was weighed out on an analytical balance (Model PM4800, Mettler Instrument Corp., Highstown, N.J. 08520 and added to the Terg-o-tometer. Two replicates were run at the same time. Unless otherwise stated, the tests were carried out for 12 minutes and rinsed for 3 minutes. After washing, the swatches were air-dried and the reflectance of the test swatches was measured with a Chroma Meter Model CR-410 manufactured by Konica Minolta. The data collected were treated with appropriate statistical analysis.

5.12.2 European Conditions

Use of Launder-O-meter, manufactured by Atlas Company, Atlanta, Ga.—To simulate the washing test under European washing conditions, a dose efficiency curve (DEC) of the mutant enzyme of interest was conducted at 40° C. using standard European testing detergents, IEC A and IEC A with Bleach (TAED-Tetra-Acetyl-ethylene-diamine acetate) and Sodium Perborate. A corresponding DEC curve of a comparative mutant enzyme was then conducted to compare the stain removal performance of the inventive mutant enzyme. This process was repeated at higher wash temperature if desirable. Typically, 4 swatches of EMPA 161, Maize starch (EMPA, Switzerland) were placed in a steel container with 250 ml of DI water containing 6.8 g/L of the IEC A detergent or 8.0 g/L of the IEC A with Bleach detergent. Two replicates were run at the same time. Unless otherwise stated the tests were carried out for 45 minutes and rinsed for 5 minutes. After washing, the swatches were air-dried and the reflectance of the test swatches was measured with a Chroma Meter Model CR-410. The data collected were treated with appropriate statistical analysis.

5.12.3 Microswatch Method of Assessing Detergent Compositions

Numerous α-amylase cleaning assays exist. Exemplary description of testing cleaning includes the following.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" is a section of the swatch that has been cut with a single-hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The "smaller swatch" can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of either metal, plastic, glass, ceramic, or other suitable material that is coated with the soil substrate for use in testing cleaning compositions for materials other than textiles. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis. A further microscreening assay can be to deliver and secure a swatch, for example an indigo dyed denim, to a well of a multi-well plate, and add particles such as sand or larger particles such as for example garnet sieved to include particle 6 to 8, or 9 gauge, and agitate the plate so as to cause abrasion of the swatch by the added particles. This assay has found use in the assessment of cellulases in stone washing applications. The effectiveness of the enzyme can be judged by either color release (e.g., released indigo is dissolved in dimethylsulfoxide and absorbance at $A_{600}$ nm is measured) to the reaction buffer or by reflectance measurements of the abraded swatch.

When, for example, untreated BMI (blood/milk/ink) swatches are washed in detergent without bleach, a large portion of the ink is released even without the help of a protease. Adding a protease leads to a small increase in ink release, which can be hard to quantify over the large background. One aspect provides a treatment protocol that allows one to control the degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, Textile Research Journal 52(4): 280 286 (1982)). Other test swatches include but are not limited to blood/milk/ink (BMI) stain(s) on a cotton-containing fabric, a spinach stain on a cotton-containing fabric, or grass on a cotton-containing fabric, and chocolate/milk/soot on a cotton-containing fabric.

A BMI stain can be fixed to cotton with 0.0003% to 0.3% hydrogen peroxide. Other combinations include grass or spinach fixed with 0.001% to 1% glutaraldehyde, gelatin and Coomassie Brilliant Blue stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see e.g., Cayot and Tainturier, Anal. Biochem. 249: 184-200 (1997)). However, if a detergent or an enzyme sample leads to the formation of unusually small peptide fragments (for example, from the presence of peptidases in the sample), then one will obtain a larger TNBS signal, i.e., more "noise".

Another means of measuring wash performance of blood/milk/ink or other stain that is based on ink release. Proteolysis of protein on the swatches leads to the release of ink particles that can be quantified by measuring the absorbance of the wash liquor. The absorbance can be measured at any wavelength between 350 and 800 nm. The wavelength is measured at 410 nm or 620 nm. The wash liquor can also be examined to determine the wash performance on stains containing grass, spinach, gelatin or Coomassie Brilliant Blue stain. Exemplary wavelengths for these stains include and 670 nm for spinach or grass and 620 nm for gelatin or Coomassie Brilliant Blue. For example, an aliquot of the wash liquor (typically 100 to 150 µL from a 96-well microplate, for example) is removed and placed in a cuvette or multiwell microplate. This is then placed in a spectrophotometer and the absorbance is read at an appropriate wavelength.

The system can also be used to determine an enhanced enzyme and/or detergent composition for dishwashing, for example, using a blood/milk/ink stain on a suitable substrate such as cloth, plastic or ceramic.

In one aspect, the a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme such as a variant protein is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tested with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains. Additional blood/milk/ink assays and conditions are provided in U.S. Pat. No. 7,122,334 (Genencor International, Inc.).

5.13 Determination of LAS Sensitivity

The variant is incubated with different concentrations of LAS (linear alkyl benzene sulphonate; Nansa 1169/P) for 10 minutes at 40° C.

The residual activity is determined using the Phadebas® assay method or the alternative method employing the PNP-$G_7$ substrate.

LAS is diluted in 0.1 M phosphate buffer pH 7.5.

The following concentrations are used:

500 ppm, 250 ppm, 100 ppm, 50 ppm, 25 ppm, and 10 ppm or no LAS.

The variant is diluted in the different LAS buffers to concentration of 0.01-5 mg/l in a total volume of 10 ml and incubated for 10 minutes in a temperature controlled water bath. The incubation is stopped by transferring a small aliquot into cold assay buffer. It is important that during activity measurement the LAS concentration is below 1 ppm, in order not to affect the activity measurement.

Then the residual activity is determined in duplicate using the above mentioned PHADEBAS® assay or alternative method.

The activity is measured after subtraction of the blank.

The activity with no LAS is 100%.

The present application is organized into a number of sections for ease of reading; however, the reader will appreciate that statements made in one section may apply to other sections. In this manner, the headings used for different sections of the disclosure should not be construed as limiting.

In order to further illustrate the present compositions and methods and advantages thereof, the following specific examples are given with the understanding that they are being offered to illustrate the present compositions and methods and should not be construed in any way as limiting its scope.

EXAMPLES

The following abbreviations apply throughout the disclosure: wt % (weight percent); ° C. (degrees Centigrade); $H_2O$ (water); $dH_2O$ or DI (deionized water); $dIH_2O$ (deionized water, Milli-Q filtration); g or gm (grams); µg (micrograms); mg (milligrams); kg (kilograms); µL and µl (microliters); mL and nil (milliliters); mm (millimeters); µm (micrometer); M (molar); mM (millimolar); µM (micromolar); U (units); MW (molecular weight); sec (seconds); min(s) (minute/minutes); hr(s) (hour/hours); DO (dissolved oxygen); W/V (weight to volume); W/W (weight to weight); V/V (volume to volume); Genencor (Danisco US Inc, Genencor Division, Palo Alto, Calif.); Ncm (Newton centimeter) and ETOH (ethanol). eq (equivalents); N (Normal); ds or DS (dry solids content).

Example 1

Expression of AmyTS23 in *B. subtilis*

To test expression of AmyTS23 full length, the synthetic DNA sequence depicted in FIG. 3 (made by Geneart, Regensburg, Germany) was cloned behind the LAT (licheniformis amylase) promoter and fused in frame to a sequence encoding the LAT signal peptide (FIG. 5) into vector pHPLT (see e.g. WO2005111203 and [Solingen et al. (2001) Extremophiles 5:333-341]) and transformed into a 9 protease deleted *B. subtilis* strain (degU$^{Hy}$32, oppΔ, ΔspoII3501, amyE::xylR-PxylAcomK-ermC, ΔaprE, ΔnprE, Δepr, ΔispA, Δbpr, Δvpr, ΔwprA, Δmpr-ybfJ, ΔnprB) (see, e.g., U.S. Pub No. 20050202535A1). Neomycin (10 µg/ml) resistant transformants secrete AmyTS23 amylase as judged by halo formation on starch plates after iodine staining (see WO2005111203). One of these amylase positive transformants was selected and designated BG6006 (pHPLT-AmyTS23). Cultures of this strain were typically grown at 37 deg for 60 to 72 hours at 250 rpm in the following medium (per liter): 10 g Soytone, 75 g glucose, 7.2 g urea, 40 mM MOPS, 4 mM Tricine, 3 mM dibasic potassium phosphate, 21.4 mM KOH, 50 mM NaCl, 276 µM potassium sulfate, 528 µM magnesium chloride, 50 µM trisodium citrate dihydrate, 100 µM calcium chloride dihydrate, 14 µM ferrous sulfate heptahydrate, 5.9 µM manganese sulfate dihydrate, 5.7 µM zinc sulfate monohydrate, 2.9 µM cupric chloride dihydrate, 4.2 µM cobalt chloride hexahydrate, 4.5 µM sodium molybdate dihydrate. For a 1 L volume, all components except for Soytone were mixed in 500 mL, sterile filtered, and added to an equal part of 2× Soytone, which had been sterilized by autoclaving. Trace metals and citrate can be made up as a 100× or 1000× stock solutions. Buffers, potassium hydroxide, sodium chloride, potassium sulfate, and magnesium chloride and trace metals can be made up as a 10× stock solutions. After all components were mixed, the pH was adjusted to 7.3. Prior to use this medium was supplemented with 20 mM calcium chloride.

The culture expressed the amylase in two major forms. A high molecular weight form was observed at the 66 kDa marker on a 10% SDS-PAGE gel. A shorter form was observed at 55 kDa.

The high molecular weight component was isolated from the culture broth by treating 500 mL of the broth with 10 mL settled volume of β-cyclodextrin-sepharose affinity matrix resin, synthesized in-house by standard protocol from β-cyclodextrin (Sigma Aldrich Cat. No. c4767) and epoxy-activated-sepharose-6B (GE Healthcare, N.J. Cat. No. 17-0480-01), over night at 4° C. with gentle agitation, collecting the resin, and washing with 25 mM bis-Tris propane buffer (pH 8.5) containing 2 mM calcium chloride ($CaCl_2$) The high molecular weight enzyme was eluted by washing the resin with the same buffer supplemented with 50 mM O-cyclodextrin. Fractions were analyzed by SDS-PAGE and those containing enzyme were pooled and dialyzed to remove β-cyclodextrin. Enzyme protein concentration was estimated by gel densitometry with OxAm amylase (Genencor) serving as the protein standard.

Example 2

Expression of AmyTS23t in *B. subtilis*

To test expression of genetically truncated AmyTS23 (AmyTS23t) the synthetic DNA fragment depicted in FIG. 4 was cloned into pHPLT and transformed into the 9 protease deleted *B. subtilis* strain as described in Example 1. Neomycin resistant transformants secrete AmyTS23t amylase as judged by halo formation on starch plates after iodine staining. One of these amylase positive transformants was selected and designated BG6006(pME622.1). This strain was cultured to produce AmyTS23t amylase as described in example 1. Culture supernatant was examined by SDS-PAGE and shown to produce a product of the expected size of 55 kDa.

The amylase protein was partially purified by the addition of $NH_4SO_4$ to 500 mL of culture to a final concentration of 1M. Next, 10 mL settled volume of Phenyl-sepharose resin was added and the mixture was gently agitated overnight at 4° C. The resin was collected and washed with 25 mM bis-Tris propane buffer (pH 8.5) containing 1M $NH_4SO_4$ and 2 mM calcium chloride ($CaCl_2$). Enzyme activity was eluted in the same buffer without $NH_4SO_4$. Fractions were analyzed by SDS-PAGE and those containing enzyme were pooled and dialyzed to remove residual $NH_4SO_4$. Enzyme protein concentration was estimated by gel densitometry with OxAm amylase (Genencor International, Inc.) serving as the protein standard.

Example 3

AmyTS23 in Cleaning Screening Assay

Partially purified AmyTS23 full length described in Example 1 was analyzed in the 96-well CS28 orange dyed rice starch soil fabric swatch micro applications cleaning assay. To conduct this assay a 96-well plate is loaded with ¼ inch fabric swatches that are cut from fabric prewashed in room temperature water for 1 hour and air dried. This rinse removes a significant amount of loosely bound soil. Alternatively, the swatches have also been pre-washed after they were loaded into the plate. Both procedures give similar results. Buffer of choice is added to the wells of the plate and the plate is temperature equilibrated to a preferred temperature. In the present example the assay was carried out in the 25 mM HEPES (pH 8.0) and in 25 mM CAPS (pH 10.3) buffers and incubation was at 20° C. or 40° C. After the equilibration period enzyme is added to the desired concentration and incubation is continued for 30 minutes to 1 hour with shaking at 750 rpm in an Eppendorf Thermomix controlled temperature block. Performance was judged by the amount of enzyme dependent color released into the solution. Color release is quantified spectrophotometrically at 488 nm. For additional information on the assay, see U.S. Pat. No. 7,122,334.

Figure 6:
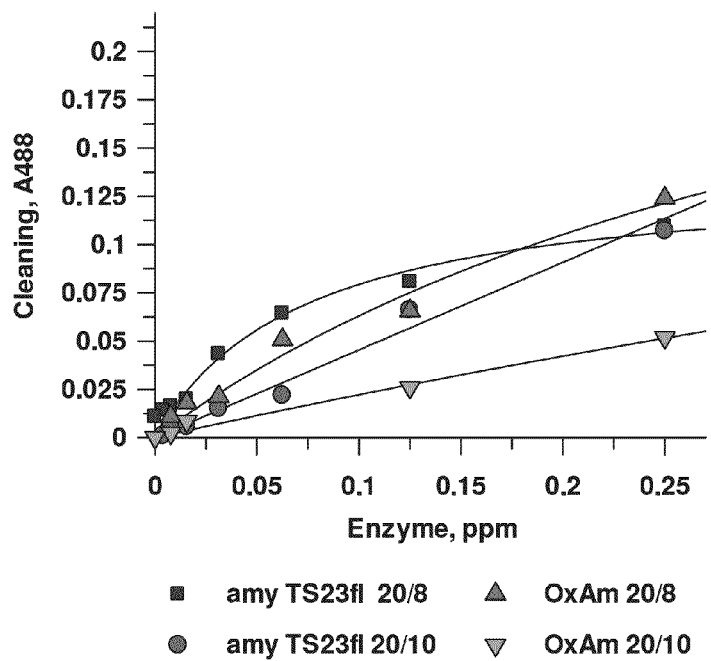
FIG. 6 is a graph showing the results of a swatch cleaning assay with the full length AmyTS23 amylase (AmyTS23fl) and OxAm control.
Figure 7:
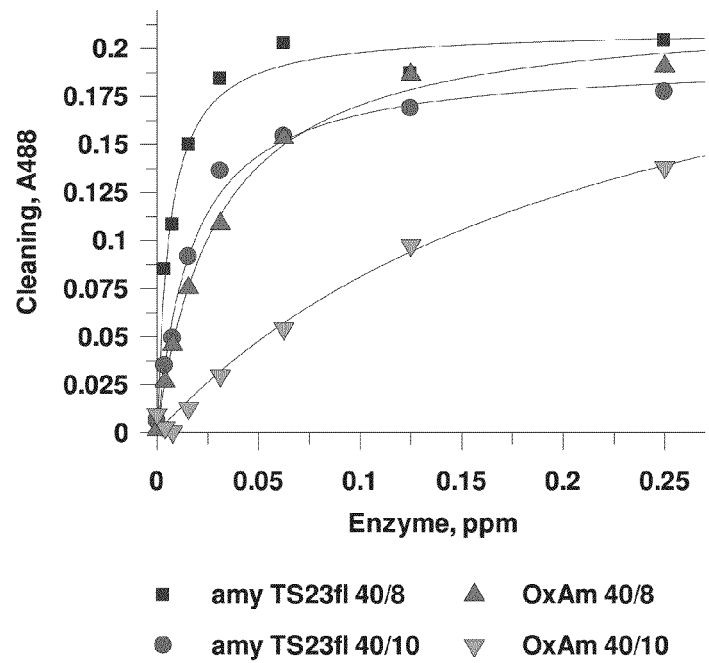
FIG. 7 is a graph showing the results of a swatch cleaning assay with amylase AmyTS23fl and OxAm control.

Cleaning data for this enzyme in this assay are shown in FIG. 6 (20° C.) and FIG. 7 (40° C.). Full length AmyTS23 (AmyTS23fl) was highly efficient in stain removal at pH 8.0, but also showed surprising stain removal at pH 10.3.

The data indicates that AmyTS23fl performs better than the control (OxAm) at both pH values.

This swatch assay can be modified in several ways for different purposes. The 96-well assay is highly suitable as a high-throughput cleaning assay by measuring absorbance spectroscopically after incubation of enzyme with swatches, while for example, a 24-well plate with swatches, cut to fit in the wells can be used to wash larger swatches for which reflectance can be measured as known in the art. The two measurements, supernatant absorbance and swatch reflectance, showed nearly perfect correlation.

The correlation of reflectance of the washed swatch with the absorbance of supernatant was high; the coefficient of determination, $r^2$, had a value of 0.99. The assay can, in principle, be scaled to a 384-well plate. The assay can be carried out with any soiled swatch and in addition to the CS28 swatch, CS26, CS27, and CS29 swatches can be tested as well (e.g., corn starch, potato starch, tapioca starch, respectively; Testfabrics, Inc., West Pittiston, Pa.) to demonstrate the efficacy of the measurement as described in Example 3. The assay may also be used with detergent compositions and conducted at different temperatures and at different pH values. These assays were adapted from U.S. Pat. No. 7,122,334.

Example 4

Cleaning Screening Assay for AmyTS23t

Figure 8:
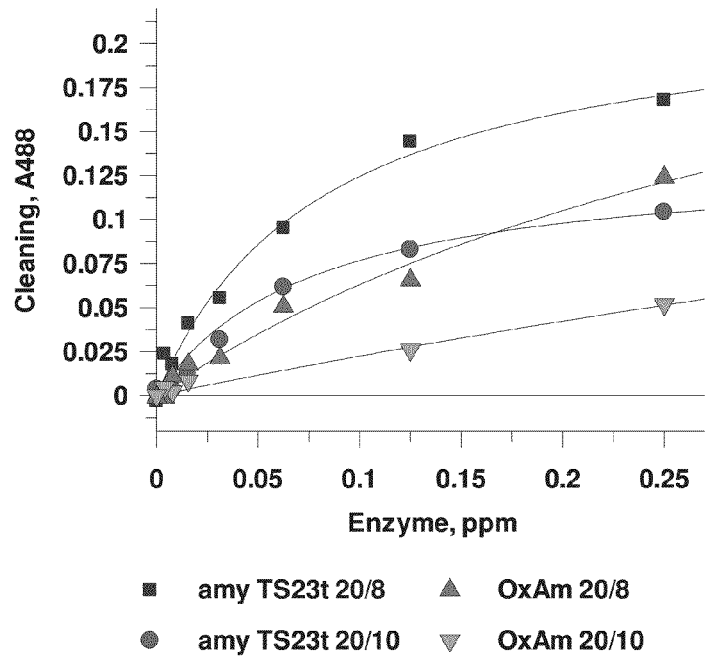
FIG. 8 is a graph showing the results of a swatch cleaning assay with amylase AmyTS23t and OxAm control.
Figure 9:
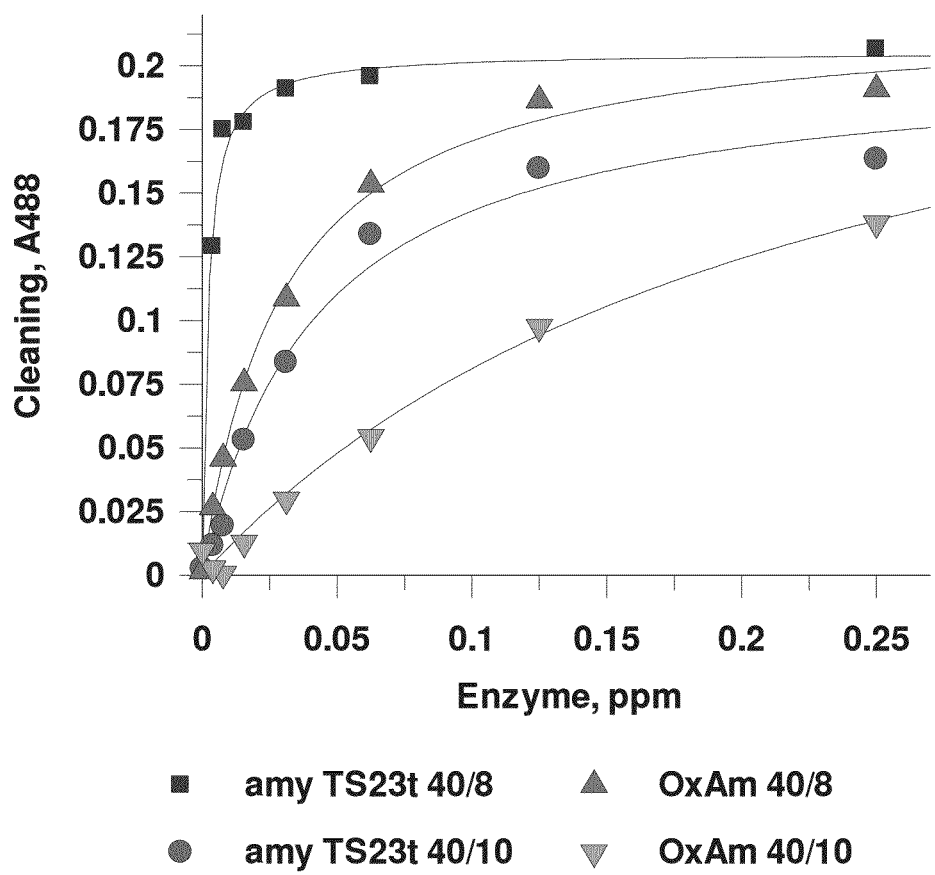
FIG. 9 is a graph showing the results of a swatch cleaning assay with AmyTS23t and OxAm control.

Partially purified truncated AmyTS23 (AmyTS23t) described in Example 2 was analyzed in the 96-well CS28 orange dyed rice starch soil fabric swatch micro applications cleaning assay as described in Example 3. Cleaning data for this enzyme in this assay are shown in FIG. 8 (20° C.) and FIG. 9 (40° C.). The data indicates that AmyTS23t performs better than the control amylase (OxAm, commercial amylase obtainable form Genencor) at both pH values. Comparison of FIGS. 6 and 8 clearly shows that the truncated AmyTS23 performs better at 20° C. than does the AmyTS23 full length molecule. The truncated molecule may thus be the better molecule for laundry applications.

Example 5

Expression of AmyTS23 Variants in *B. subtilis*

In this example, the construction of *Bacillus subtilis* strains expressing variants of AmyTS23t is described. Synthetic DNA fragment 056426 (produced by Geneart GmbH, Josef-Engert-strasse 11, D-93053 Regensburg, Germany), containing the codon optimized AmyTS23 gene (FIG. 3) served as template DNA. The pHPLT vector (Solingen et al., Extremophiles 5:333-341 [2001]) which contains the *Bacillus licheniformis* α-amylase (LAT) promoter and the LAT signal peptide (pre LAT) followed by PstI and HpaI restriction sites for cloning, was used for expression of the AmyTS23t variants.

Three DNA fragments were produced by PCR using the DNA primers listed below:
1. AmyTS23t with CGG of codon 180 and AGC of codon 181 deleted (AmyTS23tΔRS)
2. AmyTS23t with ATG of codon 201 replaced by CTG (AmyTS23t(M201L))
3. AmyTS23t with both ATG of codon 201 replaced by CTG, and CGG of codon 180 and AGC of codon 181 deleted (AmyTS23t(M201L+ΔRS)

| Primer name | DNA sequence (SEQ ID NO) |
|---|---|
| pHPLT-PstI-FW | CTCATTCTGCAGCTTCAGCAAATACGGCG (SEQ ID NO: 7) |
| pHPLT-HpaI-RV | CTCTGTTAACTCATTTGGCGACCCAGATTGAAACG (SEQ ID NO: 8) |
| TS-delRS-FW | CTATAAATTTACGGGCAAAGCATGGGATTGG (SEQ ID NO: 9) |
| TS-delRS-RV | TGCTTTGCCCGTAAATTTATAGATCCGGTTCAG (SEQ ID NO: 10) |

-continued

| Primer name | DNA sequence (SEQ ID NO) |
|---|---|
| TS-M201L-FW | CTATGACTATCTGCTGTTTGCCGATCTG (SEQ ID NO: 11) |
| TS-M201L-RV | CAGATCGGCAAACAGCAGATAGTCATAG (SEQ ID NO: 12) |
| TS-delRS/M201L-FW | GCATGGGATTGGGAAGTCGATACGGAAAACGGCAACTATGACTATCTGCTGTTTGCCG (SEQ ID NO: 13) |
| TS-delRS/M201L-RV | CGTATCGACTTCCCAATCCCATGCTTTGCCCGTAAATTTATAGATCCGGTTC (SEQ ID NO: 14) |

These DNA primers were synthesized and desalted by Sigma (Sigma-Aldrich Chemie B. V., Postbus 27, 3330 AA Zwijndrecht, The Netherlands).

For all the PCR reactions described below, a final concentration of 0.2 μM DNA primer was used (forward and reverse primer), and 0.1-10 ng of DNA template was used (DNA fragment 056426 or pDNA pHPLT). In addition, all PCR reactions were completed in a volume of 50 μl, using Finnzymes (Finnzymes OY, Keilaranta 16 A, 02150 Espoo, Finland) Phusion High-Fidelity DNA Polymerase (Cat. no. F-530L). Also, all PCR reaction mixes contained 10 μL, of 5× Phusion HF buffer, 1 μL, of 10 mM dNTP mixture, 0.75 μL, of Phusion DNA polymerase (2 units/μL), 1 μL of 100% DMSO and deionized, autoclaved water making up a final volume of 50 μl. The PCR programs, using a MJ Research PTC-200 Peltier thermal cycler (MJ Research, 590 Lincoln Street, Waltham, Mass. 02451, USA) were run as described by Finnzymes (protocol of manufacturer): 30 sec.at 98° C., 30×(10 sec.at 98° C., 20 sec.at 55° C., 22 sec./kb at 72° C.), 5 min.72° C.

1. Generation of AmyTS23tΔRS:

Two PCR reactions were performed using primers TS-delRS-FW and pHPLT-HpaI-RV on synthetic DNA fragment 056426 and primers TS-delRS-RV and pHPLT-PstI-FW on synthetic DNA fragment 056426. In order to fuse these two generated DNA fragments, 1 μl unpurified PCR mix from both reactions was added to a third PCR reaction sample in which primers pHPLT-PstI-FW and pHPLT-HpaI-RV were added.

The amplified linear 1.5 kb DNA fragment was purified (using Qiagen® QIAQUICK PCR purification kit Cat. no. 28106) and digested with PstI and HpaI restriction enzymes. Subsequently, the AmyTS23tΔRS (also referred to herein as AmyTS23tΔRS) DNA fragment and pHPLT pDNA (50 ng/μl range, digested with PstI and HpaI enzymes) were both purified (using Qiagen QIAQUICK® PCR purification kit Cat. no. 28106) and then ligated at the PstI and HpaI ends. Reaction conditions are:

4 μl of purified and, PstI and HpaI digest of the AmyTS23tΔRS DNA fragment, 2 μl of purified and, PstI and HpaI digested pHPLT DNA fragment, 8 μL T4 DNA Ligase buffer (Invitrogen Cat. no. 46300-018), 25 μl distilled, autoclaved water and 1 μL T4 DNA Ligase, 1 unit/μL (Invitrogen Cat. no. 15224-017). Ligation reaction took place for 16-20 hours at 20° C.

Subsequently, the ligation mixture was transformed into a B. subtilis strain (ΔaprE, ΔnprE, Δepr, ΔispA, Δbpr) and (degU$^{Hy}$32, oppA, ΔspoIIE3501, amyE::xylRPxylAcomK-ermC, (Δvpr, ΔwprA, Δmpr-ybfJ, ΔnprB). Transformation into B. subtilis was performed as described in WO 02/14490. The B. subtilis transformants were selected on agar plates containing Heart infusion agar (Difco, Cat. no 244400) and 10 mg/L Neomycin. Selective growth of B. subtilis transformants harboring the pHPLT-AmyTS23tΔRS vector was performed in shake flasks as described in Example 1. This growth resulted in the production of secreted AmyTS23tΔRS amylase with starch hydrolyzing activity as visualized by spotting culture supernatant on a starch agar plate followed by iodine staining.

2. Generation of AmyTS23t(M201L):

The same protocol was performed as described for the "Generation of AmyTS23tΔRS", except for the first two PCR reactions:

Two PCR reactions were performed using primers TS-M201L-FW and pHPLT-HpaI-RV on synthetic DNA fragment 056426 and primers TS-M201L-RV and pHPLT-PstI-FW on synthetic DNA fragment 056426.

3. Generation of AmyTS23t(M201L)-RSdelete:

The same protocol was performed as described for the "Generation of AmyTS23tΔRS", except for the first two PCR reactions:

Two PCR reactions were performed using primers TS-delRS/M201L-FW and pHPLT-HpaI-RV on synthetic DNA fragment 056426 and primers TS-delRS/M201L-RV and pHPLT-PstI-FW on synthetic DNA fragment 056426.

Example 6

Improved Stability of AmyTS23tΔRS in Detergent

Figure 10:
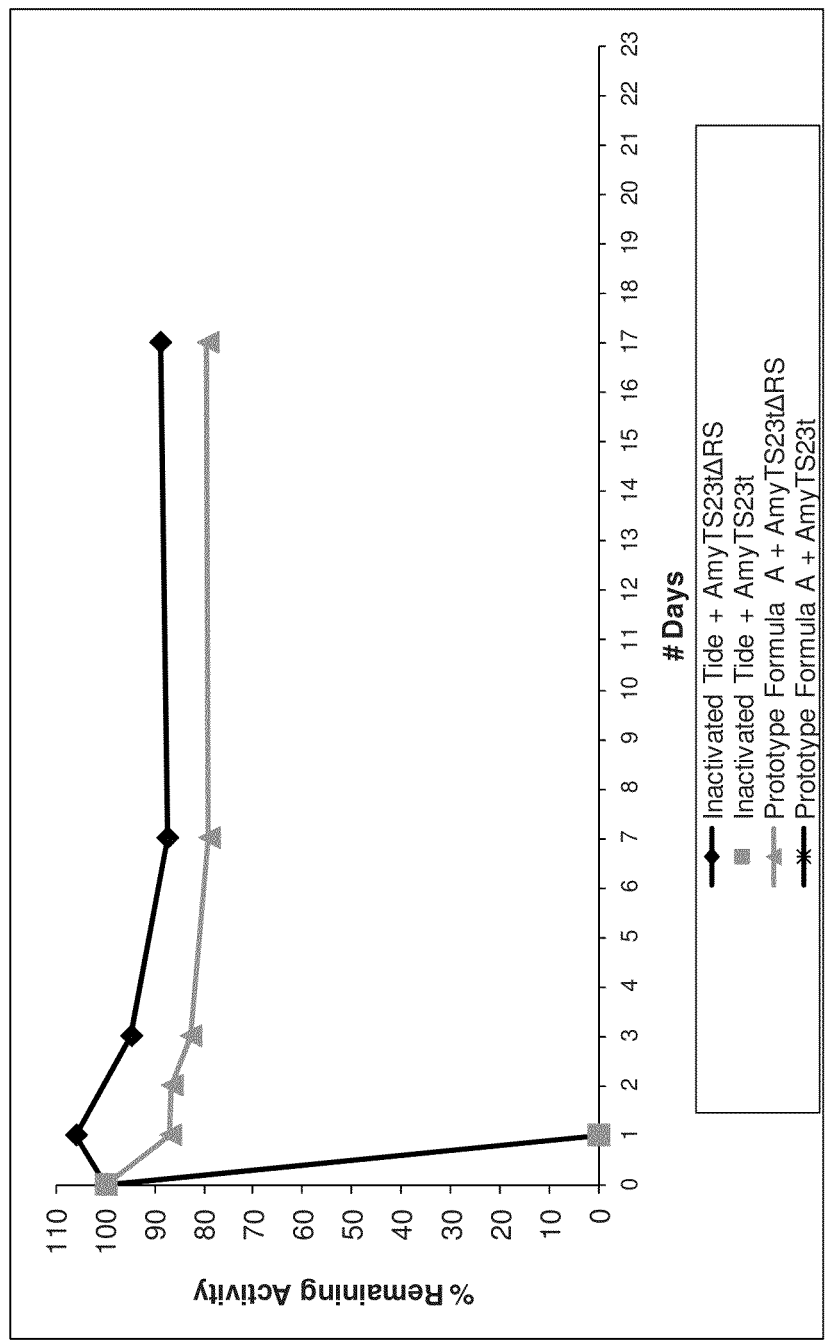
FIG. 10 is a graph showing an accelerated stability study with AmyTS23t and AmyTS23tΔRS in two different laundry detergent formulations.

Stability of AmyTS23t and AmyTS23tΔRS was tested in an accelerated stability test at 37° C. in MOPS buffer, inactivated Tide, and a prototype detergent (Prototype Formula A). Enzyme samples were incubated at 37° C. in Inactivated Liquid Tide or Prototype Formula A liquid detergents and the remaining activity was determined over time in a Megazyme assay. The results are shown in FIG. 10. In the presence of either of the two detergent bases (Inactivated Tide, and Prototype A detergent), only AmyTS23tΔRS is stable without any additional additives. As shown in FIG. 10, AmyTS23t lost the bulk of its activity after the first day and lost the activity completely after 2 days of accelerated testing at 37° C. AmyTS23tΔRS is stable under the same conditions and retained about 90% of original enzyme activity after 17 days.

TABLE 6-1

| Treatment | Percentage of Enzyme activity retained | | | | | |
|---|---|---|---|---|---|---|
| | Day 0 | Day 1 | Day 2 | Day 3 | Day 7 | Day 17 |
| Inactivated Tide + AmyTS23tΔRS | 100 | 106 | 89.5 | 94.8 | 87.5 | 88.9 |
| Inactivated Tide + AmyTS23t | 100 | 0 | | | | |
| Inactivated Tide + STZ | 100 | 100 | 99.1 | 100 | 96.5 | 88.3 |
| Prototype Formula A + AmyTS23tΔRS | 100 | 86.9 | 86.6 | 82.8 | 79.0 | 79.3 |
| Prototype Formula A + AmyTS23t | 100 | 0 | | | | |
| Prototype Formula A + STZ | 100 | 86.5 | 88.7 | 86.5 | 77.7 | 78.2 |

Example 7

Oxidative Stability of AmyTS23 and AmyTS23 Mutants

Amylases vary in their response to exposure to peracetic acid (PAA). Thus, this example was designed to determine the oxidative stability of AmyTS23 and AmyTS23 mutant amylases. The conditions are outlines, below:

| Stress Conditions | Megazyme Assay |
|---|---|
| 30 mM Enzyme | Blocked PNPG7 |
| 25 mM Borate, pH 8.65 | 25 mM BTP/CaCl2, pH 6.9 |
| 1 mM PAA, 40 C., 5 min | 40 C. 45 min kinetic |
| Quench 25 mM BTP, pH 8.5 | |

Enzyme dilutions were prepared in 25 mM Borate buffer, pH 8.64, 2 mM $Ca^{++}$ by buffer exchange on 1 mL spin desalting columns. Peracetic acid contained in 5 μL volume was added to 25 μL of enzyme solution to yield 0 to 1 mM peracetic acid and the samples were incubated for 5 minutes at 40° C. in a PCR machine (DNA Engine, BioRad). The reaction was quenched using 25 mM BTP, pH 8.5. Residual amylase activity was measured using a standard amylase assay kit from Megazyme (Wicklow, Ireland).

Figure 11:
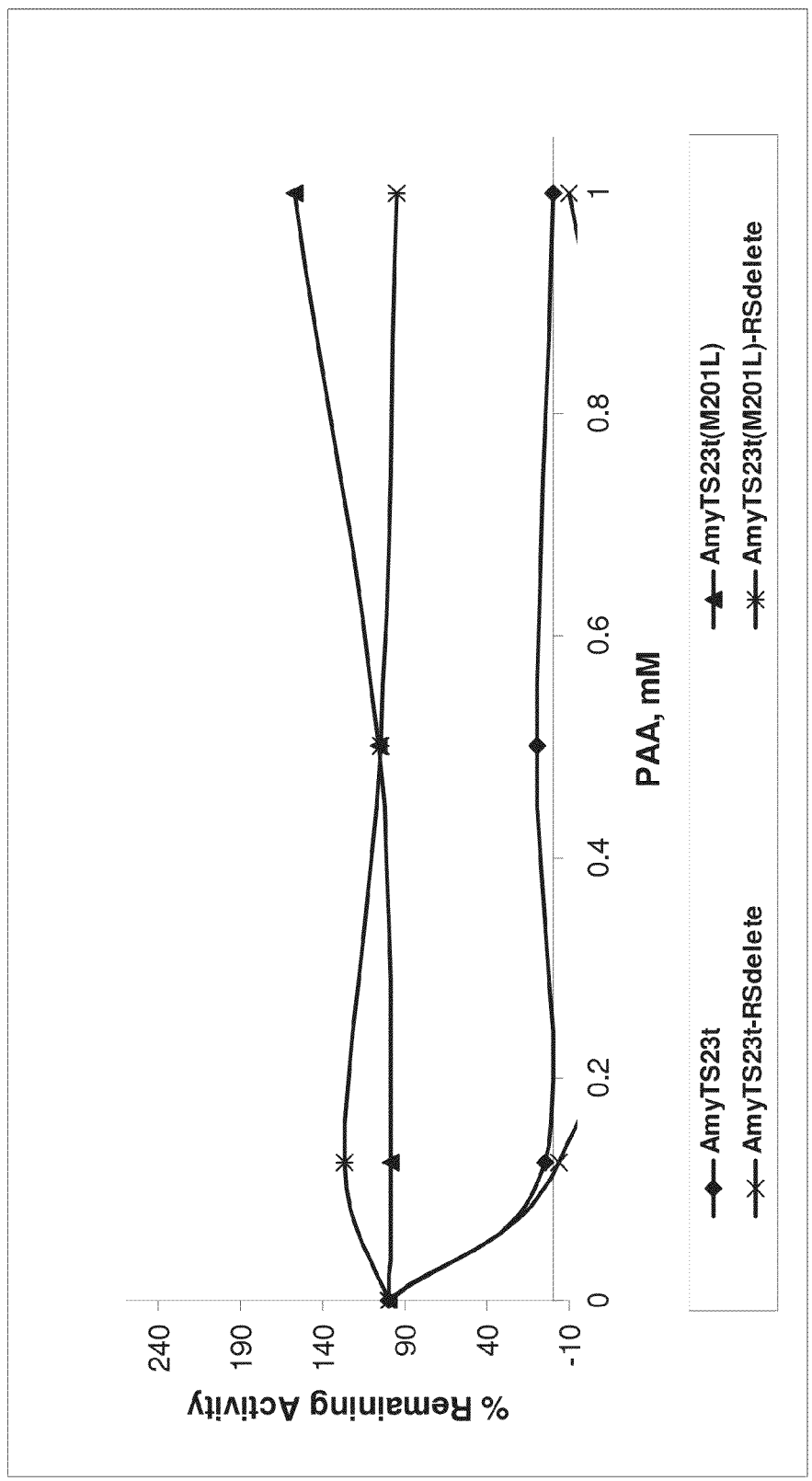
FIG. 11 is a graph showing the oxidative stability of AmyTS23t, AmyTS23tΔRS and AmyTS23t(M201L+ΔRS).

As shown in FIG. 11, TS23t(M201L) has greater than 100% stability at low PAA concentration then decreases at higher concentrations. TS23t (M201L+ΔRS) has 25% increase in stability at low PAA concentrations that dips to below 100% finally maintaining oxidative stability at higher PAA concentrations. TS23t, TS23tΔRS, and Amy 707 are unstable in the presence of PAA decreasing in stability at low concentrations to baseline.

Example 8

Cleaning Performance in Detergent

Figure 12:
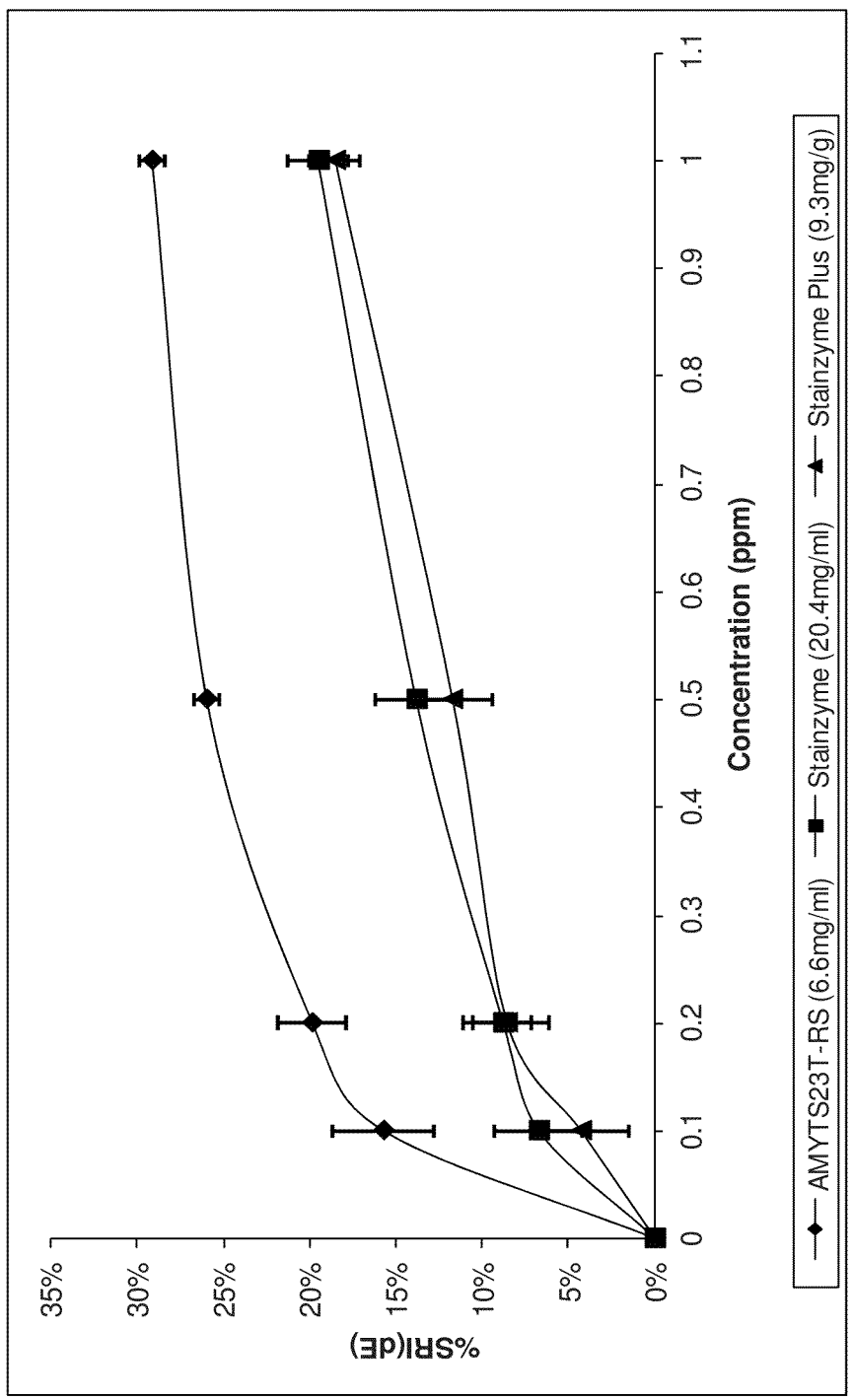
FIG. 12 is a graph showing the performance of the AmyTS23tΔRS in liquid detergent on rice starch swatches.

A dose efficiency curve of selected concentrations of AmyTS23tΔRS was generated using the procedure described in Section 5.12.1 of this patent application. The performance evaluation was conducted both at 20° C. and 40° C. using a Tergotometer. The same conditions were used to generate dose efficiency curves for Stainzyme and Stainzyme Plus. As can be seen from the data (FIG. 12), AmyTS23tΔRS is significant superior to both Stainzyme products at 20° C. and moderately better at 40° C. This data supports the unique benefit of AmyTS23tΔRS as a unique high performing cold water enzyme.

Example 9

Amylase Production in B. subtilis

In this Example, production of Bacillus sp. TS-23t and variants thereof in B. subtilis are described. Transformation was performed as known in the art (See e.g., WO 02/14490). Briefly, the gene encoding the parent amylases was cloned into the pHPLT expression vector, which contains the LAT promoter (PLAT), a sequence encoding the LAT signal peptide (preLAT), followed by PstI and HpaI restriction sites for cloning.

The coding region for the LAT signal peptide is shown below:

(SEQ ID NO: 5)
atgaaacaacaaaaacggctttacgcccgattgctgacgctgttatttgcgctcatcttcttgctgcctcattctgcagcttcagca.

The amino acid sequence of the LAT signal peptide is shown below:

MKQQKRLYARLLTLLFALIFLLPHSAASA    (SEQ ID NO: 6)

The coding region for the mature AmyTS-23t amylase is shown in FIG. 4.

The amino acid sequence of the mature AmyTS-23t amylase was used as the basis for making the variant libraries described herein is shown in FIG. 2.

The PCR products were purified using Qiaquik columns from Qiagen, and resuspended in 50 μL of deionized water. 50 μL of the purified DNA was digested with HpaI (Roche) and PstI (Roche) and the resultant DNA resuspended in 30 μL of deionized water. 10-20 ng/μL of the DNA was cloned into plasmid pHPLT using PstI and HpaI cloning sites. The ligation mixtures were directly transformed into competent B. subtilis cells (genotype: Δvpr, ΔwprA, Δmpr-ybfJ, ΔnprB). The B. subtilis cells have a competency gene (comK) which is placed under a xylose inducible promoter, so xylose was used to induce competency for DNA binding and uptake (see Hahn et al., Mol. Microbiol., 21:763-775 [1996]).

The elements of plasmid pHPLT-AmyS include: pUB 110=DNA fragment from plasmid pUB110 (McKenzie et al., Plasmid 15: 93-103 [1986]). Plasmid features include: ori-pUB110=origin of replication from pUB 110, neo=neomycin resistance gene from pUB 110, Plat=transcriptional promoter from B. licheniformis amylase, Pre LAT=signal peptide from B. licheniformis amylase, SAMY 425ss=The coding region for truncated Amy TS-23 gene sequence (replaced by the coding regions for each truncated Amy TS-23 variant expressed in this study), Terminator=transcriptional terminator from B. licheniformis amylase.

Amylase Expression—2 ml Scale

B. subtilis clones containing AmyTS23t expression vectors were replicated with a steel 96-well replicator from glycerol stocks into 96-well culture plates (BD, 353075) containing 150 μl of LB media+10 μg/ml neomycin, grown overnight at 37° C., 220 rpm in a humidified enclosure. A 100 μl aliquot from the overnight culture was used to inoculate 2000 μl defined media+10 μg/ml neomycin in 5 ml plastic culture tubes. The cultivation media was an enriched semi-defined media based on MOPs buffer, with urea as major nitrogen source, glucose as the main carbon source, and supplemented with 1% soytone and 5 mM calcium for robust cell growth. Culture tubes were incubated at 37° C., 250 rpm, for 72 hours. Following this incubation, the culture broths were centrifuged for 10 minutes at 3000×g. The supernatant solution was decanted into 15 ml polypropylene conical tubes and 80 μL of each sample were aliquoted into 96 well plates for protein quantitation.

Generation of *Bacillus* sp. AmyTS23t Combinatorial Charge Library

Multiple protein variants spanning a range of a physical properties of interest are selected from existing libraries or are generated by site-directed mutagenesis techniques as known in the art (See e.g., U.S. patent application Ser. Nos. 10/576,331, 11/581,102, and 11/583,334). This defined set of probe proteins is then assayed in a test of interest.

AmyTS23t is a truncated form of *Bacillus* sp. TS-23 α amylase (see Lin et al., 1998, Production and properties of a raw-starch-degrading amylase from the thermophilic and alkaliphilic *Bacillus* sp. TS-23, Biotechnol. Appl. Biochem. 28:61-68). Expression of AmyTS23t in a multiple-protease deleted *B. subtilis* strain (degU$^{Hy}$32, oppA, AspoII3501, amyE::xylRPxylAcomK-ermC, ΔaprE, ΔnprE, Δepr, ΔispA, Δbpr, Δvpr, ΔwprA, Δmpr-ybfJ, ΔnprB) is described, herein, (See, also, U.S. Pub. No. 20050202535A1). The AmyTS23t plasmid DNA isolated from transformed *B. subtilis* cells was sent to DNA2.0 Inc. (Menlo Park, Calif.) as the template for CCL construction. DNA 2.0 was requested to prepare a parent construct for the CCL by introducing the following seven mutations into AmyTS23t, which was consequently termed AmyTS23t-7mut: Q98R, M201L, S243Q R309A, Q320R, Q359E, and K444E. Variants were supplied as glycerol stocks in 96-well plates. Subsequently a request was made to DNA2.0 Inc. for the generation of positional libraries at each of the four sites in AmyTS23t-7mut amylase that are shown in Table 9-1.

The AmyTS23t-7mut combinatorial charge library was designed by identifying the following four residues in AmyTS23t-7mut: Gln 87, Asn 225, Asn 272, and Asn 282. A four site, 81-member CCL was created by making all combinations of three possibilities at each site: wild-type, arginine, or aspartic acid.

TABLE 9-1

AmyTS23t-7mut CCL Variants

| Variant # | Q87 | N225 | N272 | N282 | Δ Charge |
|---|---|---|---|---|---|
| Parent 1 | — | — | — | — | 0 |
| 2 | Q87E | N225E | N272E | N282E | −4 |
| 3 | Q87E | N225E | N272E | N282R | −2 |
| 4 | Q87E | N225E | N272E | — | −3 |
| 5 | Q87E | N225E | N272R | N282E | −2 |
| 6 | Q87E | N225E | N272R | N282R | 0 |
| 7 | Q87E | N225E | N272R | — | −1 |
| 8 | Q87E | N225E | — | N282E | −3 |
| 9 | Q87E | N225E | — | N282R | −1 |
| 10 | Q87E | N225E | — | — | −2 |
| 11 | Q87E | N225R | N272E | N282E | −2 |
| 12 | Q87E | N225R | N272E | N282R | 0 |
| 13 | Q87E | N225R | N272E | — | −1 |
| 14 | Q87E | N225R | N272R | N282E | 0 |
| 15 | Q87E | N225R | N272R | N282R | +2 |
| 16 | Q87E | N225R | N272R | — | +1 |
| 17 | Q87E | N225R | — | N282E | −1 |
| 18 | Q87E | N225R | — | N282R | +1 |
| 19 | Q87E | N225R | — | — | 0 |
| 20 | Q87E | — | N272E | N282E | −3 |
| 21 | Q87E | — | N272E | N282R | −1 |
| 22 | Q87E | — | N272E | — | −2 |
| 23 | Q87E | — | N272R | N282E | −1 |
| 24 | Q87E | — | N272R | N282R | +1 |
| 25 | Q87E | — | N272R | — | 0 |
| 26 | Q87E | — | — | N282E | −2 |
| 27 | Q87E | — | — | N282R | 0 |
| 28 | Q87E | — | — | — | −1 |

TABLE 9-1-continued

AmyTS23t-7mut CCL Variants

| Variant # | Q87 | N225 | N272 | N282 | Δ Charge |
|---|---|---|---|---|---|
| 29 | Q87R | N225E | N272E | N282E | −2 |
| 30 | Q87R | N225E | N272E | N282R | 0 |
| 31 | Q87R | N225E | N272E | — | −1 |
| 32 | Q87R | N225E | N272R | N282E | 0 |
| 33 | Q87R | N225E | N272R | N282R | +2 |
| 34 | Q87R | N225E | N272R | — | +1 |
| 35 | Q87R | N225E | — | N282E | −1 |
| 36 | Q87R | N225E | — | N282R | +1 |
| 37 | Q87R | N225E | — | — | 0 |
| 38 | Q87R | N225R | N272E | N282E | 0 |
| 39 | Q87R | N225R | N272E | N282R | +2 |
| 40 | Q87R | N225R | N272E | — | +1 |
| 41 | Q87R | N225R | N272R | N282E | +2 |
| 42 | Q87R | N225R | N272R | N282R | +4 |
| 43 | Q87R | N225R | N272R | — | +3 |
| 44 | Q87R | N225R | — | N282E | +1 |
| 45 | Q87R | N225R | — | N282R | +3 |
| 46 | Q87R | N225R | — | — | +2 |
| 47 | Q87R | — | N272E | N282E | −1 |
| 48 | Q87R | — | N272E | N282R | +1 |
| 49 | Q87R | — | N272E | — | 0 |
| 50 | Q87R | — | N272R | N282E | +1 |
| 51 | Q87R | — | N272R | N282R | +3 |
| 52 | Q87R | — | N272R | — | +2 |
| 53 | Q87R | — | — | N282E | 0 |
| 54 | Q87R | — | — | N282R | +2 |
| 55 | Q87R | — | — | — | +1 |
| 56 | — | N225E | N272E | N282E | −3 |
| 57 | — | N225E | N272E | N282R | −1 |
| 58 | — | N225E | N272E | — | −2 |
| 59 | — | N225E | N272R | N282E | −1 |
| 60 | — | N225E | N272R | N282R | +1 |
| 61 | — | N225E | N272R | — | 0 |
| 62 | — | N225E | — | N282E | −2 |
| 63 | — | N225E | — | N282R | 0 |
| 64 | — | N225E | — | — | −1 |
| 65 | — | N225R | N272E | N282E | −1 |
| 66 | — | N225R | N272E | N282R | +1 |
| 67 | — | N225R | N272E | — | 0 |
| 68 | — | N225R | N272R | N282E | +1 |
| 69 | — | N225R | N272R | N282R | +3 |
| 70 | — | N225R | N272R | — | +2 |
| 71 | — | N225R | — | N282E | 0 |
| 72 | — | N225R | — | N282R | +2 |
| 73 | — | N225R | — | — | +1 |
| 74 | — | — | N272E | N282E | −2 |
| 75 | — | — | N272E | N282R | 0 |
| 76 | — | — | N272E | — | −1 |
| 77 | — | — | N272R | N282E | 0 |
| 78 | — | — | N272R | N282R | +2 |
| 79 | — | — | N272R | — | +1 |
| 80 | — | — | — | N282E | −1 |
| 81 | — | — | — | N282R | +1 |

Example 10

Performance Index

Rice Microswatch Assay

Test detergents were prepared as described elsewhere in this document. The equipment used included a New Brunswick Innova 4230 shaker/incubator and a SpectraMAX (type 340) MTP reader. The MTPs were obtained from Corning (type 3641). Aged rice starch with orange pigment swatches (CS-28) were obtained from Center for Test Materials (Vlaardingen, Netherlands). Before cutting 0.25-inch circular microswatches, the fabric was washed with water. Two microswatches were placed in each well of a 96-well microtiter plate. The test detergent was equilibrated at 20° C. (North America) or 40° C. (Western Europe). 190 μl of detergent solution was added to each well of the MTP, containing micro swatches. To this mixture, 10 μl of the diluted enzyme solution was added. The MTP was sealed with adhesive foil and placed in the incubator for 1 hour with agitation at 750 rpm at the desired test temperature (typically 20° C. or 40° C.). Following incubation, 150 μl of the solution from each well was transferred into a fresh MTP. This MTP was read at 488 nm using a SpectraMax MTP reader to quantify cleaning. Blank controls, as well as controls containing microswatches and detergent but no enzyme were also included.

Detergent Heat Inactivation

Heat inactivation of commercial detergent formulas serves to destroy the enzymatic activity of any protein components while retaining the properties of non-enzymatic components. Thus this method was suitable for preparing commercially purchased detergents for use in testing the enzyme variants of the present compositions and methods. For North American (NA) and Western European (WE) heavy duty liquid laundry (HDL) detergents, heat inactivation was performed by placing pre-weighed liquid detergent (in a glass bottle) in a water bath at 95° C. for 2 hours. The incubation time for heat inactivation of North American (NA) and Japanese (JPN) heavy duty granular laundry (HDG) detergent was 8 hours and that for Western European (WE) HDG detergent was 5 hours. The incubation time for heat inactivation of NA and WE auto dishwashing (ADW) detergents was 8 hours. The detergents were purchased from local supermarket stores. Both un-heated and heated detergents were assayed within 5 minutes of dissolving the detergent to accurately determine percentage deactivated. Enzyme activity was tested by AAPF assay using 1 mg/ml AAPF.

For testing of enzyme activity in heat-inactivated detergents, working solutions of detergents were made from the heat inactivated stocks. Appropriate amounts of water hardness (6 gpg or 12 gpg) and buffer were added to the detergent solutions to match the desired conditions (Table 10-1). The solutions were mixed by vortexing or inverting the bottles.

TABLE 10-1

Laundry and Dishwashing Conditions

| Region | Form | Dose | Detergent* | Buffer | Gpg | pH | T (° C.) |
|---|---|---|---|---|---|---|---|
| Laundry (heavy duty liquid and granular) | | | | | | | |
| NA | HDL | 0.78 g/l | P&G TIDE ® 2X | 5 mM HEPES | 6 | 8.0 | 20 |
| WE | HDL | 5.0 g/L | Henkel Persil | 5 mM HEPES | 12 | 8.2 | 40 |
| WE | HDG | 8.0 g/L | P&G Ariel | 2 mM $Na_2CO_3$ | 12 | 10.5 | 40 |
| JPN | HDG | 0.7 g/L | P&G TIDE ® | 2 mM $Na_2CO_3$ | 6 | 10.0 | 20 |
| NA | HDG | 1.0 g/L | P&G TIDE ® | 2 mM $Na_2CO_3$ | 6 | 10.0 | 20 |
| Automatic Dishwashing | | | | | | | |
| WE | ADW | 3.0 g/L | RB Calgonit | 2 mM $Na_2CO_3$ | 21 | 10.0 | 40 |
| NA | ADW | 3.0 g/L | P&G Cascade | 2 mM $Na_2CO_3$ | 9 | 10.0 | 40 |

*Abbreviations: Proctor & Gamble (P&G); and Reckitt Benckiser (RB).

Calculation of Enzyme Performance

The obtained absorbance value was corrected for the blank value (i.e., obtained after incubation of microswatches in the absence of enzyme). The resulting absorbance was a measure for the hydrolytic activity. The results are shown in Tables 10-2 and 10-3. Enzyme performance was assessed using heat inactivated detergents as described above. Winners are defined as those having Performance Index (PI) a greater than 1. PI is the ratio of mutant residual activity to WT residual activity.

TABLE 10-2

TS23t-7mut CCL - CS-28 rice starch microswatch winners, Tide 2x

| Variant # | 87 | 225 | 272 | 282 | rel charge | PI |
|---|---|---|---|---|---|---|
| 11 | Q87E | N225R | N272E | N282E | −2 | 1.24 |
| 12 | Q87E | N225R | N272E | N282R | 0 | 1.20 |
| 13 | Q87E | N225R | N272E | | −1 | 1.16 |
| 14 | Q87E | N225R | N272R | N282E | 0 | 1.15 |
| 17 | Q87E | N225R | | N282E | −1 | 1.34 |
| 18 | Q87E | N225R | | N282R | 1 | 1.26 |
| 19 | Q87E | N225R | | | 0 | 1.34 |
| 20 | Q87E | | N272E | N282E | −3 | 1.17 |
| 21 | Q87E | | N272E | N282R | −1 | 1.34 |
| 22 | Q87E | | N272E | | −2 | 1.13 |
| 27 | Q87E | | | N282R | 0 | 1.22 |
| 28 | Q87E | | | | −1 | 1.22 |
| 29 | Q87R | N225E | N272E | N282E | −2 | 1.44 |
| 30 | Q87R | N225E | N272E | N282R | 0 | 1.15 |
| 31 | Q87R | N225E | N272E | | −1 | 1.36 |
| 35 | Q87R | N225E | | N282E | −1 | 1.15 |
| 40 | Q87R | N225E | N272E | | 1 | 1.27 |
| 44 | Q87R | N225R | | N282E | 1 | 1.38 |
| 45 | Q87R | N225R | | N282R | 3 | 1.21 |
| 47 | Q87R | | N272E | N282E | −1 | 1.65 |
| 48 | Q87R | | N272E | N282R | 1 | 1.52 |
| 49 | Q87R | | N272E | | 0 | 1.28 |
| 50 | Q87R | | N272R | N282E | 1 | 1.10 |
| 53 | Q87R | | | N282E | 0 | 1.47 |
| 54 | Q87R | | | N282R | 2 | 1.25 |
| 55 | Q87R | | | | 1 | 1.51 |
| 64 | | N225E | | | −1 | 1.15 |
| 65 | | N225R | N272E | N282E | −1 | 1.26 |
| 66 | | N225R | N272E | N282R | 1 | 1.22 |
| 67 | | N225R | N272E | | 0 | 1.19 |
| 74 | | | N272E | N282E | −2 | 1.21 |
| 76 | | | N272E | | −1 | 1.13 |
| 80 | | | | N282E | −1 | 1.27 |
| 81 | | | | N282R | 1 | 1.49 |

TABLE 10-3

TS-23t-7mut CCL CS-28 rice starch microswatch winners, Persil

| Variant # | 87 | 225 | 272 | 282 | rel charge | PI |
|---|---|---|---|---|---|---|
| 4 | Q87E | N225E | N272E | 0 | −3 | 1.13 |
| 6 | Q87E | N225E | N272R | N282R | 0 | 1.11 |
| 9 | Q87E | N225E | | N282R | −1 | 1.20 |
| 10 | Q87E | N225E | | 0 | −2 | 1.17 |
| 11 | Q87E | N225R | N272E | N282E | −2 | 1.41 |
| 13 | Q87E | N225R | N272E | 0 | −1 | 1.40 |

TABLE 10-3-continued

TS-23t-7mut CCL CS-28 rice starch microswatch winners, Persil

| Variant # | 87 | 225 | 272 | 282 | rel charge | PI |
|---|---|---|---|---|---|---|
| 14 | Q87E | N225R | N272R | N282E | 0 | 1.28 |
| 15 | Q87E | N225R | N272R | N282R | 2 | 1.13 |
| 16 | Q87E | N225R | N272R | 0 | 1 | 1.17 |
| 17 | Q87E | N225R |  | N282E | −1 | 1.51 |
| 18 | Q87E | N225R |  | N282R | 1 | 1.47 |
| 19 | Q87E | N225R |  | 0 | 0 | 1.48 |
| 20 | Q87E |  | N272E | N282E | −3 | 1.46 |
| 21 | Q87E |  | N272E | N282R | −1 | 1.40 |
| 22 | Q87E |  | N272E | 0 | −2 | 1.42 |
| 25 | Q87E |  | N272R | 0 | 0 | 1.18 |
| 26 | Q87E |  |  | N282E | −2 | 1.54 |
| 27 | Q87E |  |  | N282R | 0 | 1.47 |
| 28 | Q87E |  |  | 0 | −1 | 1.40 |
| 29 | Q87R | N225E | N272E | N282E | −2 | 1.46 |
| 30 | Q87R | N225E | N272E | N282R | 0 | 1.59 |
| 31 | Q87R | N225E | N272E | 0 | −1 | 1.14 |
| 34 | Q87R | N225E | N272R | 0 | 1 | 1.29 |
| 35 | Q87R | N225E |  | N282E | −1 | 1.47 |
| 36 | Q87R | N225E |  | N282R | 1 | 1.62 |
| 37 | Q87R | N225E |  | 0 | 0 | 1.53 |
| 38 | Q87R | N225R | N272E | N282E | 0 | 1.13 |
| 39 | Q87R | N225R | N272E | N282R | 2 | 1.13 |
| 40 | Q87R | N225R | N272E | 0 | 1 | 1.17 |
| 41 | Q87R | N225R | N272R | N282E | 2 | 1.31 |
| 44 | Q87R | N225R |  | N282E | 1 | 1.26 |
| 47 | Q87R |  | N272E | N282E | −1 | 1.45 |
| 48 | Q87R |  | N272E | N282R | 1 | 1.50 |
| 49 | Q87R |  | N272E | 0 | 0 | 1.17 |
| 50 | Q87R |  | N272R | N282E | 1 | 1.16 |
| 53 | Q87R |  |  | N282E | 0 | 1.21 |
| 54 | Q87R |  |  | N282R | 2 | 1.30 |
| 55 | Q87R |  |  | 0 | 1 | 1.33 |
| 56 |  | N225E | N272E | N282E | −3 | 1.29 |
| 57 |  | N225E | N272E | N282R | −1 | 1.12 |
| 58 |  | N225E | N272E | 0 | −2 | 1.41 |
| 59 |  | N225E | N272R | N282E | −1 | 1.16 |
| 61 |  | N225E | N272R | 0 | 0 | 1.20 |
| 66 |  | N225R | N272E | N282E | 1 | 1.27 |
| 67 |  | N225R | N272E | 0 | 0 | 1.34 |
| 71 |  | N225R |  | N282E | 0 | 1.17 |
| 73 |  | N225R |  | 0 | 1 | 1.12 |
| 74 |  |  | N272E | N282E | −2 | 1.29 |
| 75 |  |  | N272E | N282R | 0 | 1.24 |
| 76 |  |  | N272E | 0 | −1 | 1.20 |
| 78 |  |  | N272R | N282E | 2 | 1.18 |
| 79 |  |  | N272R | 0 | 1 | 1.11 |
| 80 |  |  |  | N282E | −1 | 1.11 |
| 81 |  |  |  | N282R | 1 | 1.33 |

Example 11

Combined LAS/Chelant Stability

This example describes determining the relationship between protein charge and stability in a reaction medium containing an anionic surfactant and a chelant. LAS stability was measured after incubation of the test amylases in the presence of 0.1% LAS (dodecylbenzenesulfonate sodium) and 10 mM EDTA, by measuring the residual activity in a BODIPY assay according to the methods described above. For determination of the α-amylase activity of the stressed and unstressed samples, the BODIPY-starch assay was used. Residual LAS and EDTA from the stress plates do not affect the BODIPY-starch assays.

Reagents used included: control buffer: 50 mM HEPES, 0.005% Tween-80, pH 8.0; and stress buffer 50 mM HEPES, 0.1% (w/v) LAS (dodecylbenzene-sulfonate, sodium salt, Sigma D-2525), 10 mM EDTA, pH 8.0. Enzyme variants (20 ppm) were diluted 1:20 into 96-well non-binding flat-bottom plate containing either control or stress buffer and mixed. The control plate was incubated at room temperature while the stress plate was immediately placed at 37° C. for 30-60 min (depending on the stability of the enzyme being tested). Following incubation, enzyme activity was measured using the BODIPY-starch assay for amylases. The fraction of remaining or residual activity is equal to the reaction rate of the stressed sample divided by the reaction rate of the control sample. The parent enzymes and variants are stable for 60 min in the control buffer.

Table 11-1 shows data for those variants having enhanced LAS/EDTA stability as a function of net charge change relative to wild type TS-23t-7mut, for a library containing 80 variants. This library was designed and constructed according to the methods described in example 2 to span several net charges relative to the parent TS-23t-7mut molecule. A Performance Index (PI) greater than 1 indicates the variant has higher specific activity than the S242Q parent on this starch substrate (a corn starch).

TABLE 11-1

TS23t-7mut CCL - LAS/EDTA stability winners

| Variant # | 87 | 225 | 272 | 282 | Charge | Mut residual act./WT residual act. (PI) |
|---|---|---|---|---|---|---|
| 2 | Q87E | N225E | N272E | N282E | −4 | 1.39 |
| 5 | Q87E | N225E | N272R | N282E | −2 | 1.51 |
| 8 | Q87E | N225E |  | N282E | −3 | 1.29 |
| 11 | Q87E | N225R | N272E | N282E | −2 | 1.38 |
| 14 | Q87E | N225R | N272R | N282E | 0 | 1.64 |
| 17 | Q87E | N225R |  | N282E | −1 | 1.39 |
| 20 | Q87E |  | N272E | N282E | −3 | 1.39 |
| 23 | Q87E |  | N272R | N282E | −1 | 1.65 |
| 26 | Q87E |  |  | N282E | −2 | 1.41 |
| 29 | Q87R | N225E | N272E | N282E | −2 | 2.02 |
| 31 | Q87R | N225E | N272E | 0 | −1 | 1.39 |
| 32 | Q87R | N225E | N272E | N282E | 0 | 2.21 |
| 33 | Q87R | N225E | N272E | N282R | 2 | 1.29 |
| 34 | Q87R | N225E | N272R | 0 | 1 | 1.47 |
| 35 | Q87R | N225E |  | N282E | −1 | 2.08 |
| 37 | Q87R | N225E |  | 0 | 0 | 1.41 |
| 38 | Q87R | N225R | N272E | N282E | 0 | 1.85 |
| 40 | Q87R | N225R | N272E | 0 | 1 | 1.38 |
| 41 | Q87R | N225R | N272R | N282E | 2 | 2.15 |
| 43 | Q87R | N225R | N272R | 0 | 3 | 1.63 |
| 44 | Q87R | N225R |  | N282E | 1 | 2.33 |
| 46 | Q87R | N225R |  | 0 | 2 | 1.62 |
| 47 | Q87R |  | N272E | N282E | −1 | 2.38 |
| 48 | Q87R |  | N272E | N282R | 1 | 1.24 |
| 49 | Q87R |  | N272E | 0 | 0 | 1.53 |
| 50 | Q87R |  | N272R | N282E | 1 | 2.14 |
| 51 | Q87R |  | N272R | N282R | 3 | 1.25 |
| 52 | Q87R |  | N272R | 0 | 2 | 1.60 |
| 53 | Q87R |  |  | N282E | 0 | 2.27 |
| 54 | Q87R |  |  | N282R | 2 | 1.34 |
| 55 | Q87R |  |  | 0 | 1 | 1.62 |
| 56 | 0 | N225E | N272E | N282E | −3 | 1.69 |
| 59 | 0 | N225E | N272R | N282E | −1 | 1.77 |
| 62 | 0 | N225E |  | N282E | −2 | 1.50 |
| 65 | 0 | N225R | N272E | N282E | −1 | 1.66 |
| 67 | 0 | N225R | N272E | 0 | 0 | 1.24 |
| 68 | 0 | N225R | N272E | N282E | 1 | 1.80 |
| 70 | 0 | N225R | N272R | 0 | 2 | 1.25 |
| 71 | 0 | N225R |  | N282E | 0 | 1.48 |
| 73 | 0 | N225R |  | 0 | 1 | 1.29 |
| 74 | 0 |  | N272E | N282E | −2 | 1.54 |
| 77 | 0 |  | N272R | N282E | 0 | 1.78 |
| 80 | 0 |  |  | N282E | −1 | 1.52 |

Figure 13:
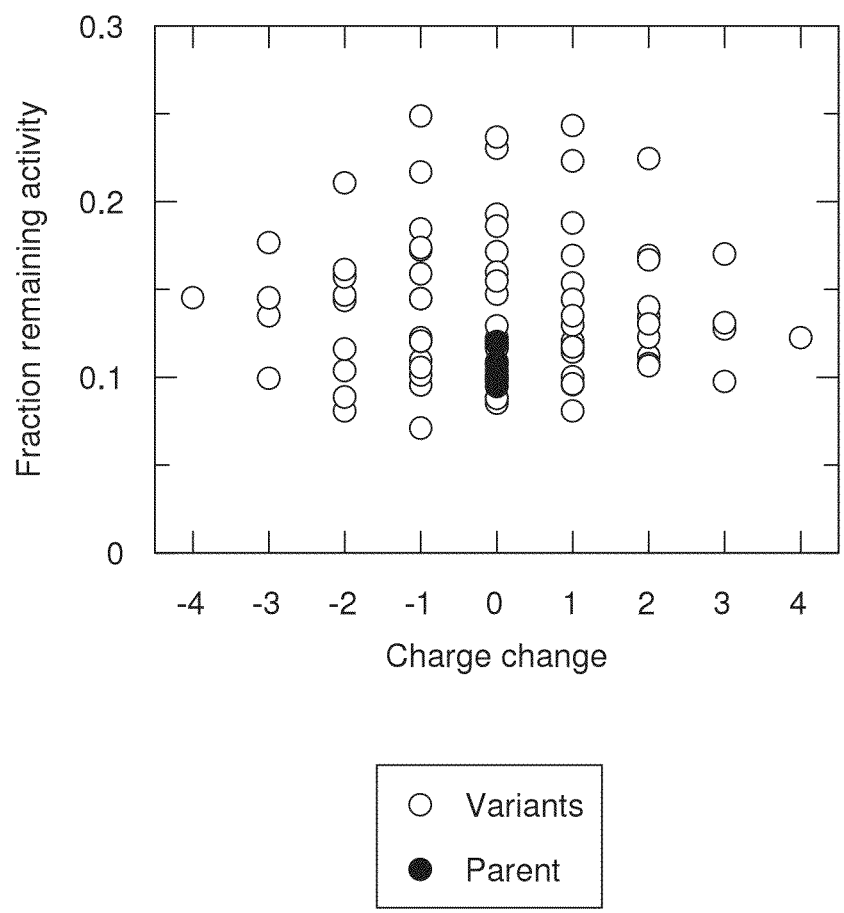
FIG. 13 is a graph depicting residual activity as a function of charge change.

For ASP and FNA there is a charge dependence for LAS/EDTA stability. (See WO/2008/153925, filed Jun. 6, 2008. Adding negative charge increases stability. But, even when going one or two charges more positive than the parent, it is possible to find, by our method, an arrangement of charge mutations which confer equal or greater stability than the parent. This approach is also effective in larger enzymes, such as TS23t' shown in FIG. 13 where the detrimental effect of adding positive charges on stability can be compensated by an optimal charge arrangement that increases stability.

All publications and patents mentioned in the above specification are herein incorporated by reference. Various modifications and variations will be apparent to those skilled in the art without departing from the scope and spirit of the invention. Although the present compositions and methods has been described in connection with specific preferred embodiments, it should be understood that they should not be unduly limited to such specific embodiments. Indeed, various modifications of the described modes for carrying out the present compositions and methods will be apparent to those skilled in the art, and are intended to be within the scope of the following claims.

What is claimed is:

1. A variant of a parent AmyTS23 alpha-amylase, wherein the variant has alpha-amylase activity, an amino acid sequence which has at least 90% identity to SEQ ID NO: 2, and comprises a deletion of residues R180 and S181.

2. The variant of claim 1, wherein the variant has at least 90% identity to SEQ ID NO: 2.

3. The variant of claim 2, wherein the variant has at least 95% identity to SEQ ID NO: 2.

4. The variant of claim 1, wherein the variant has increased cleaning activity against starch stains in cold water compared to the alpha-amylase having the amino acid sequence of SEQ ID NO: 1.

5. The variant of claim 1, wherein the variant has increased detergent stability compared to the alpha-amylase having the amino acid sequence of SEQ ID NO: 1.

6. The variant of claim 1, further comprising a substitution of the residue at position 201.

7. The variant of claim 6, wherein the variant has increased oxidative stability compared to the alpha-amylase having the amino acid sequence of SEQ ID NO: 1.

8. The variant of claim 6, wherein the substitution is M201L.

9. The variant of claim 1, further comprising a substitution at one or more residues selected from the group consisting of residue 87, residue 225, residue 243, residue 272, and residue 282.

10. A manual or automatic dishwashing composition comprising the variant of claim 1, and one or more of: a surfactant, detergent builder, a complexing agent, a polymer, a bleaching system, a stabilizer, a foam booster, a suds suppressor, an anti-corrosion agent, a soil-suspending agent, an anti-soil redeposition agent, a dye, a bactericide, a hydrotope, a tarnish inhibitor, and a perfume.

11. A laundry detergent additive comprising the variant of claim 1, and one or more of: a surfactant, detergent builder, a complexing agent, a polymer, a bleaching system, a stabilizer, a foam booster, a suds suppressor, an anti-corrosion agent, a soil-suspending agent, an anti-soil redeposition agent, a dye, a bactericide, a hydrotope, an optical brightener, a fabric conditioner, and a perfume.

12. A method for removing starch from a textile comprising, incubating the textile in the presence of the variant of claim 1; and
wherein said incubating removes the starch from the textile.

13. A method for processing starch comprising, incubating the starch in the presence of the variant of claim 1.

* * * * *